US008383656B2

(12) United States Patent
Chen et al.

(10) Patent No.: US 8,383,656 B2
(45) Date of Patent: Feb. 26, 2013

(54) THIAZOLIDINEDIONE ENERGY RESTRICTION-MIMETIC AGENTS

(75) Inventors: Ching-Shih Chen, Upper Arlington, OH (US); Jih-Hwa Guh, Taipei (TW)

(73) Assignee: The Ohio State University Research Foundation, Columbus, OH (US)

( * ) Notice: Subject to any disclaimer, the term of this patent is extended or adjusted under 35 U.S.C. 154(b) by 124 days.

(21) Appl. No.: 12/901,782

(22) Filed: Oct. 11, 2010

(65) Prior Publication Data
US 2011/0086895 A1 Apr. 14, 2011

Related U.S. Application Data

(60) Provisional application No. 61/250,045, filed on Oct. 9, 2009, provisional application No. 61/304,881, filed on Feb. 16, 2010.

(51) Int. Cl.
*A61K 31/426* (2006.01)
*C07D 277/04* (2006.01)

(52) U.S. Cl. ......... 514/369; 548/146; 548/183; 514/365

(58) Field of Classification Search .................. 548/146, 548/183; 514/365, 369
See application file for complete search history.

(56) References Cited

U.S. PATENT DOCUMENTS

| | | | |
|---|---|---|---|
| 4,376,777 A | 3/1983 | Kawamatsu et al. | |
| 5,387,596 A | 2/1995 | Takebayashi et al. | |
| 5,801,173 A | 9/1998 | Lohray et al. | |
| 6,046,222 A | 4/2000 | Antonucci et al. | |
| 6,765,013 B2 | 7/2004 | Pfahl et al. | |
| 7,566,787 B2 | 7/2009 | Chen | |
| 7,714,005 B2 * | 5/2010 | Chen et al. | 514/369 |
| 7,714,044 B2 | 5/2010 | Schambony et al. | |
| 7,973,062 B2 * | 7/2011 | Chen et al. | 514/369 |
| 2006/0252801 A1 | 11/2006 | Chen | |
| 2007/0117887 A1 | 5/2007 | Naik et al. | |

FOREIGN PATENT DOCUMENTS

| | | |
|---|---|---|
| EP | 0 263 705 | 4/1988 |
| EP | 0 335 595 | 10/1989 |
| EP | 454501 | 4/1991 |
| EP | 0 682 145 | 11/1995 |
| FR | 1344883 | 10/1963 |
| GB | 1 003 083 | 9/1965 |
| JP | 39-009280 | 6/1964 |
| JP | 39-0011770 | 6/1964 |
| JP | 49-057048 | 6/1974 |
| JP | 64-24852 | 1/1989 |
| JP | 3-020353 | 1/1991 |
| JP | 7247978 | 9/1995 |
| JP | 7-310095 | 11/1995 |
| JP | 9-318983 | 12/1997 |
| WO | 2006/069186 | 6/2006 |
| WO | 2006/069217 | 6/2006 |

OTHER PUBLICATIONS

Jedlinski, Z.J. et al., "New Poly bis (benzirnidazobenzisoquinolinoes)", Macromolecules, vol. 16, No. 4, pp. 552-526, 1983.
Yamazaki et al., "Syntheses of polymers using 1, 4, 5-naphthalenetricarboxylic anhydride. V. Synthesis of polyamide-imides from 1, 4, 5-naphthalenetricarboxylic anhydrive 3." Nippon Kagaku Kaishi, vol. 12, pp. 2401-2405, 1973.
"1H-Benz[de]ilsoquioline-6-carboxamide, 2, 3-dihydro-2-(4-methoxyphenly)-N, N-dimethyl-3, 3-dioxo-", Interbioscreen Compound Library, XP002320325, 2003.
1-HBenz[de]isoquinoline-6-carboxamide,2,3-dihydro-N-methyl-3, 3-dioxo-N-(phenylmehyl)-2-[2-(trifluoromethyl) phenyl]-(9C1) (CA Index Name), XP002320326, 2001.
Yang et al , "Pharmacological Exploitation of the Peroxisome Proliferator-Activated Receptor γ Agonist Ciglitazone to develop a novel class of Androgen Receptor-Ablative agents", J. Med Chem, 51, pp. 2100-2107 (2008).
Palakurthia, Sangeetha S., Anticancer Effects of Thiazolidinediones are Independent of Peroxisome Proliferator-activated Receptor γ and Mediated by Inhibition of Translation, Cancer Research 61, 6213-6218, Aug. 15, 2001.
Qin, Chunhua, et al., "Peroxisome Proliferator-activated Receptor γ Agonists Induce Proteasome-dependent Degradation of Cyclin D1 and Estrogen Receptor a in MCF-7 Breast Cancer Cells", Cancer Research 63, 958-964, Mar. 1, 2003.
Kwon, Younggil, Handbook of Essential Pharmacokinetics, Phamacodynamics and Drug Metabolism for Industrial Scientists, Jun. 24, 2001, Chapter 12, pp. 207-228.
Metabolomics [online], Retrieved from the Internet Apr. 24, 2008, www.en.wikipedia.org/wiki/Metabolomics.
Cancer Topics [online], Retrieved from the Internet Apr. 24, 2008. www.nci.gov/cancertopics/druginfo/alphalist/print?page=&keyword.
Heinlein et al., "Androgen Receptor in Prostate Cancer", Endocrine reviews 2004, 25(2), 276-308.
Schafer et al., "Failure is an option: Learning from unsuccessful proof-of-concept trials", Drug Discovery Today 2008, 13 (21/22), 913-916.
Horig et al., "From bench to clinic and back: Perspective on the 1st IQPC Translational Research Conference", Journal of Translational Medicine 2004, 2(44).
Huang et al.,Development of Small-Molecule Cyclin D1-Oblative Agents J. Med. Chem, 2006, pp. 49, 4684-4689.
International Search Report and Written Opinion from PCT/US05/46454, mailed Jul. 14, 2006.
International Search Report and Written Opinion for PCT/US05/46534, mailed Mar. 14, 2008.

(Continued)

*Primary Examiner* — Golam M M Shameem
(74) *Attorney, Agent, or Firm* — Tarolli, Sundheim, Covell & Tummino LLP

(57) ABSTRACT

A method of inhibiting glycolysis in a subject by administering a pharmaceutical composition including a thiazolidinedione derivative to the subject is described. The thiazolidinedione derivatives are effective energy restriction mimetic agents, and can therefore be used to treat or prevent cancer in a subject, treat metabolic disorder, or increase the longevity of a subject. Various thiazolidinedione derivatives are also suitable for activating adenosine phosphate-activated protein kinase or inhibiting IL-6 expression.

2 Claims, 19 Drawing Sheets

OTHER PUBLICATIONS

International Search Report and Written Opinion from PCT/US09/34650 dated Jul. 16, 2009.

Iyang et al., "Peroxisome proliferator-activated receptor γ-Independent suppression of androgen receptor expression by troglitazone mechanism and pharmacologic exploitation", Cancer Res. 67(7), pp. 3229-3238 (2007).

Yu et al., (2001) Specific protection against breast cancers by cyclin D1 ablation. Nature 411:1017-21.

Altiok, et al., PPARgamma induces cell cycle withdrawal: inhibition of E2F/DP DNA-binding activity via down-regulation of PP2A. Genes Dev, 11: 1987-1998, 1997.

Clark et al., "Substituted dihydrobenzopyran and Dihydrobenzofuran Thiazolidine-2,4-diones as Hypoglycemic Agents", J Med Chem vol. 34, pp. 319-325, chart 1, 1991.

Golub et al., "Molecular Classification of Cancer: Class Discovery and Class Prediction by Gene Expression Monitoring", Science, vol. 236, pp. 531-537, Oct. 15, 1999.

Gupta, et al., Target genes of peroxisome proliferator-activated receptor gamma in colorectal cancer cells. J Biol Chem, 276: 29681-29687, 2001.

Huang, et al (Jan 13, 2005), Peroxisome Proliferator-Activated Receptor γ-Independent Ablation of Cyclin D1 by Thiazolidinediones and Their Derivatives in Breast Cancer Cells, Mol Pharmacol 67: 1342-1348.

Orlinskii, "Preparative synthesis method for thiazolidine-2, 4-dione and its N-derivatives", Pharmaceutical Chemical Journal, vol. 29, No. 2, pp. 144, 1995.

Reddy et al. (1999), Novel Antidiabetic and Hypolipedemic Agents. 5. Hydroxyl versus Benzyloxy Containing Chroman Derivatives, Journal of Med Chem 42: 3265-3278.

Shiau et al. (Feb. 15, 2005), "Thiazolidenediones Mediate Apoptosis in Prostate Cancer Cells in Part through Inhibition of Bcl-xL/Bcl-2 Functions Independently of PPARy", Cancer Research 2005; 65:(4) Feb. 15, 2005, pp. 1561-1569.

Tontonoz, et al., Terminal differentiation of human liposarcoma cells induced by induced by ligands for peroxisome proliferator-activated receptor gamma and the retinoid X receptor. Proc Natl Acad Sci U S A, 94: 237-241, 1997.

\* cited by examiner

Fig. 2B. Schematic representation of a combinatorial strategy to prepare a focused compound library of OSU-CG12. $R_1$ and $R_2$ represent substituents to be incorporated into the pharmacophore in the first round of lead optimization.

THIAZOLIDINEDIONE ENERGY RESTRICTION-MIMETIC AGENTS

CROSS REFERENCE TO RELATED APPLICATIONS

This application claims priority to U.S. Provisional Patent Application No. 61/250,045, filed Oct. 9, 2009 and U.S. Provisional Patent Application No. 61/304,881, filed Feb. 16, 2010, both of which are hereby incorporated by reference in their entirety.

GOVERNMENT FUNDING

The present invention was supported, at least in part, by government support by the Nation Institutes of Health under Grant No. CA112250. The Government may have certain rights in this invention.

BACKGROUND

Thiazolidinediones (TZDs), including rosiglitazone, pioglitazone, troglitazone, and ciglitazone, are selective ligands for the nuclear transcription factor peroxisome proliferator-activated receptor (PPAR)γ. These TZDs improve insulin sensitivity by regulating many aspects of adipose tissue function through the transcriptional activation of insulin-sensitive genes involved in glucose homeostasis, fatty acid metabolism, and triacylglycerol storage in adipocytes. Moreover, TZD-mediated PPARγ activation has been shown to promote the differentiation of pre-adipocytes by mimicking the genomic effects of insulin on adipocytes, and to modulate the expression of adiponectin, pro-inflammatory cytokines like IL-6 and TNFα, and a host of endocrine regulators in adipocytes and macrophages. Through these beneficial effects, TZDs offer a new type of oral therapy for type II diabetes by reducing insulin resistance and assisting glycemic control.

Like adipocytes, many human cancer cell lines have been reported to exhibit high levels of PPARγ expression. In vitro exposure of these tumor cells to high doses ($\geqq 50$ μM) of TZDs, especially troglitazone and ciglitazone, led to cell cycle arrest, apoptosis and/or redifferentiation, suggesting a putative link between PPARγ signaling and the antitumor activities of TZDs. Grommes et al., Lancet Oncol., 5, p. 419-429 (2004). Furthermore, the in vivo anticancer efficacy of troglitazone was demonstrated in a few clinical cases that involved patients with liposarcomas or prostate cancer. Demetri et al. Proc Natl Acad Sci USA. 96, p. 3951-3956 (1999) and Hisatake et al., Cancer Res., 60, p. 5494-5498 (2000). Accumulating evidence indicates that troglitazone and ciglitazone mediate PPARγ-independent antitumor effects by targeting diverse signaling pathways governing cell cycle progression and survival of cancer cells. Wei et al., Cancer Lett., 276, p. 119-124 (2009).

Of the various "off-target" mechanisms identified, the effects of TZDs on the expression of a broad range of cell cycle- and apoptosis-regulatory proteins, including β-catenin, cyclin D1, Sp1, androgen receptor (AR), and epidermal growth factor receptor (EGFR), through proteasomal degradation or transcriptional repression, are especially noteworthy. Researchers have obtained evidence that this effect is attributable to the ability of TZDs to activate β-transducin repeat-containing protein (β-TrCP)-mediated proteasomal degradation of target proteins, such as β-catenin, cyclin D1, and Sp1, by increasing the expression level of this E3 ubiquitin ligase. Wei et al., Mol. Pharmacol.; 72, p. 725-733 (2007) and Wei et al., J Biol. Chem., 283, p. 26759-26770 (2008). In the course of the investigation of the mechanism underlying TZD-induced β-TrCP-mediated proteolysis of cyclin D1 and Sp1, it was observed that β-TrCP-dependent degradation also occurs under conditions of glucose deprivation.

In contrast to cancer cells, nonmalignant cells are resistant to these PPARγ-independent antitumor effects, which underscores the potential of TZDs as scaffolds to develop novel antitumor agents. This premise was demonstrated to be true for two PPARγ-inactive derivatives, STG28 and OSU-CG12, which exhibit multifold higher antitumor potencies than the respective parent compounds, troglitazone and ciglitazone. Huang et al., J. Med. Chem., 49, p. 4684-4689 (2006) and Yang et al., J. Med. Chem., 51, p. 2100-2107 (2008).

Another possible target for thiazolidinediones is adenosine monophosphate-activated protein kinase (AMPK). The functional role of AMPK in regulating energy homeostasis and insulin sensitivity at both cellular and whole body levels is known. In response to stimuli such as exercise, cellular stress, and adipokines, this cellular fuel-sensing enzyme induces a series of metabolic changes to balance energy consumption, including stimulation of glucose and fatty acid uptake, fatty acid oxidation, and mitochondrial biogenesis, and inhibition of glycogen synthesis, via multiple downstream signaling pathways controlling nutrient uptake and energy metabolism. More recently, accumulating evidence suggests a link between AMPK and cancer cell growth and survival in light of its ability to activate tuberous sclerosis complex 2, a tumor suppressor that negatively regulates protein synthesis by inhibiting mammalian homolog of target of rapamycin (mTOR). Inoki et al., Cell, 115, 577-590 (2003). From a mechanistic perspective, AMPK integrates growth factor signaling with cellular metabolism through the negative regulation of mTOR. In addition, AMPK has been reported to suppress inflammatory responses by inhibiting the production of inflammatory cytokines, especially interleukin (IL)-6, in macrophages. Lihn et al., Mol Cell Endocrinol., 292, 36-41 (2008) Together, these findings suggest that AMPK represents a therapeutically relevant target for the treatment of Type II diabetes, metabolic syndrome, and cancer.

Cancer cells gain growth advantages by shifting cellular metabolism to aerobic glycolysis in their microenvironment, providing the so-called Warburg effect. Samudio et al., Cancer Res. 69, p. 2163-2166 (2009). The Warburg effect is the observation that most cancer cells predominantly produce energy by glycolysis followed by lactic acid fermentation in the cytosol, rather than by oxidation of pyruvate in mitochondria like most normal cells. This occurs even if oxygen is plentiful. The Warburg effect may be a consequence of damage to the mitochondria in cancer, an adaptation to low-oxygen environments within tumors, or a result of cancer genes shutting down the mitochondria because they are involved in the cell's apoptosis program.

Targeting aerobic glycolysis to exploit the differential susceptibility of malignant versus normal cells to glycolytic inhibition is therefore a useful approach for cancer therapy. Targeting aerobic glycolysis can also be used for other purposes, such as the treatment of diabetes or to increase lifespan. An example of the use of aerobic glycolysis for cancer therapy is the in vivo efficacy of dietary caloric restriction in suppressing carcinogenesis in various spontaneous or chemical-induced tumor animal models. See Jiang et al., Cancer Res 68, p. 5492-5499 (2008); Hursting et al., Annu Rev Med 54, p. 131-152 (2003); Thompson et al., J. Mammary Gland Biol Neoplasia 8, p. 133-142 (2003); and Berrigan et al., Carcinogenesis 23, p. 817-822 (2002).

Information on suppressing carcinogenesis using various compounds such as resveratrol (Baur et al., Nat Rev Drug Discov. 5, p. 493-506 (2006) and Cucciolla et al., Cell Cycle 6, p. 2495-2510 (2007)) or 2-deoxyglucose (Zhu et al., Cancer Res. 65, p. 7023 (2005)) is also available. The energy restriction mimetic agents 2-deoxyglucose and resveratrol have received wide attention because of their abilities to mimic the beneficial effects of energy restriction by inhibiting glucose metabolism and uptake, respectively. However, the therapeutic applications of these agents were restricted by their relatively weak in vitro potencies. There remains a need for new energy restriction mimetic agents, particularly those exhibiting increased potencies, for use in treating cancer, metabolic disorder, or other conditions involving aberrant glycolysis.

SUMMARY OF THE INVENTION

The invention provides a method of inhibiting glycolysis in a subject that includes administering to the subject a pharmaceutical composition including a thiazolidinedione derivative. Thiazolidinedione derivatives represent a novel class of energy restriction mimetic agents as a result of their ability to inhibit glycolysis, which represents a form of energy restriction similar to that resulting from glucose starvation. The method of inhibiting glycolysis in a subject using thiazolidinedione derivatives can be used to inhibit tumor glycolytic metabolism and thereby treat or prevent cancer in a subject, and can also be used to increase the longevity of a subject, including subjects that have not been diagnosed with cancer. The thiazolidinedione derivatives useful for this method are further defined by Formula's I, II, III, and IV provided herein.

The invention also provides a method for activating adenosine monophosphate-activated protein kinase by providing an effective amount of a thiazolidinedione derivative. Furthermore, because activation of AMPK leads to an inhibition of IL-6 expression, the invention also provides a method of inhibiting IL-6 expression in a subject by administering to the subject a pharmaceutical composition including a thiazolidinedione derivative. Suitable thiazolidinedione derivatives for activating AMPK and inhibiting IL-6 expression include those defined by particular embodiments of Formula's I, III, and IV.

BRIEF DESCRIPTION OF THE FIGURES

The present invention may be more readily understood by reference to the following drawings, wherein.

Figure 17:
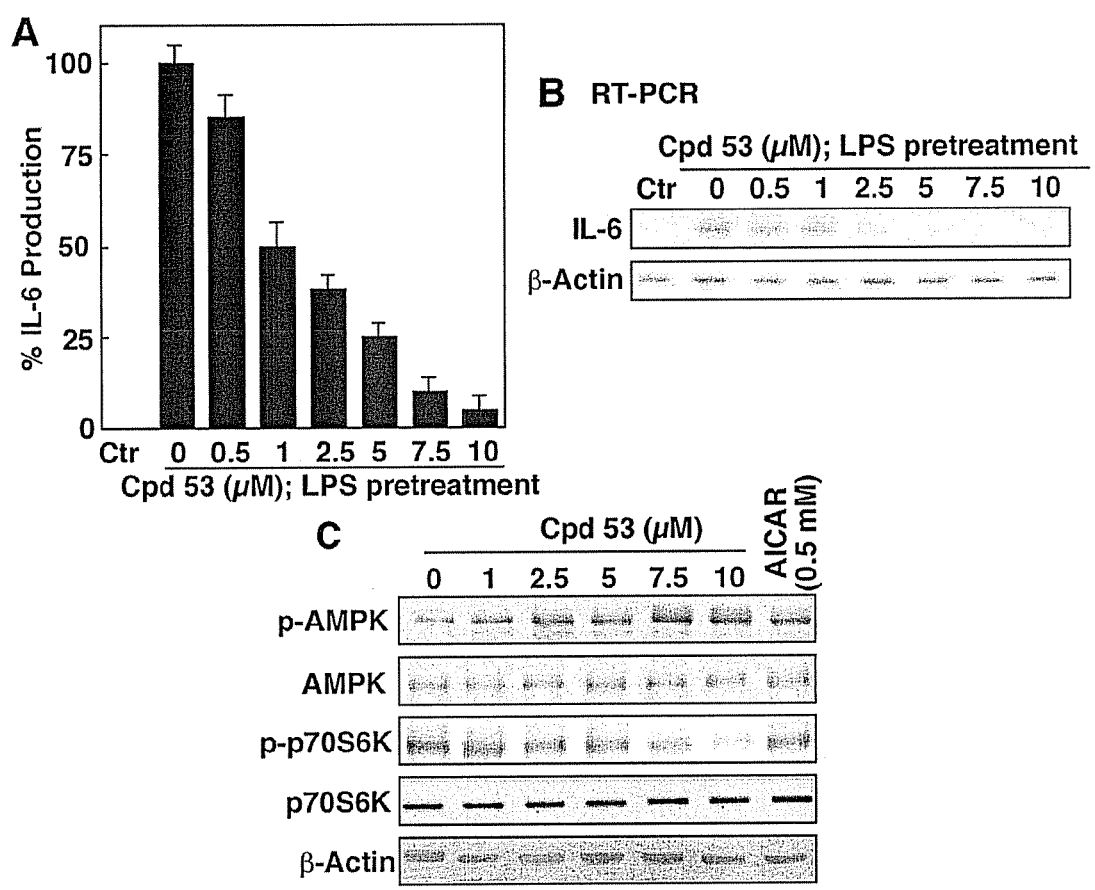

FIG. 17; section (A) provides the ELISA analysis of the dose-dependent effect of compound 53 on LPS-stimulated IL-6 production in THP-1 macrophages in 10% FBS-containing medium after 6 h of treatment. Columns, mean; bars, SD (N=3). Section (B) shows the results of RT-PCR analysis of the dose-dependent suppressive effect of compound 53 on the mRNA levels of IL-6 in LPS-treated THP-1 macrophages in 10% FBS-containing medium after 6 h of treatment. Columns, mean; bars, SD (N=3). Section (C) shows the Western blot analysis of the dose-dependent effect of compound 53 relative to 0.5 mM AICAR on the phosphorylation levels of AMPK and p70S6K in LPS-treated THP-1 macrophages in 10% FBS-containing medium after 6 h of treatment.

Figure 18:
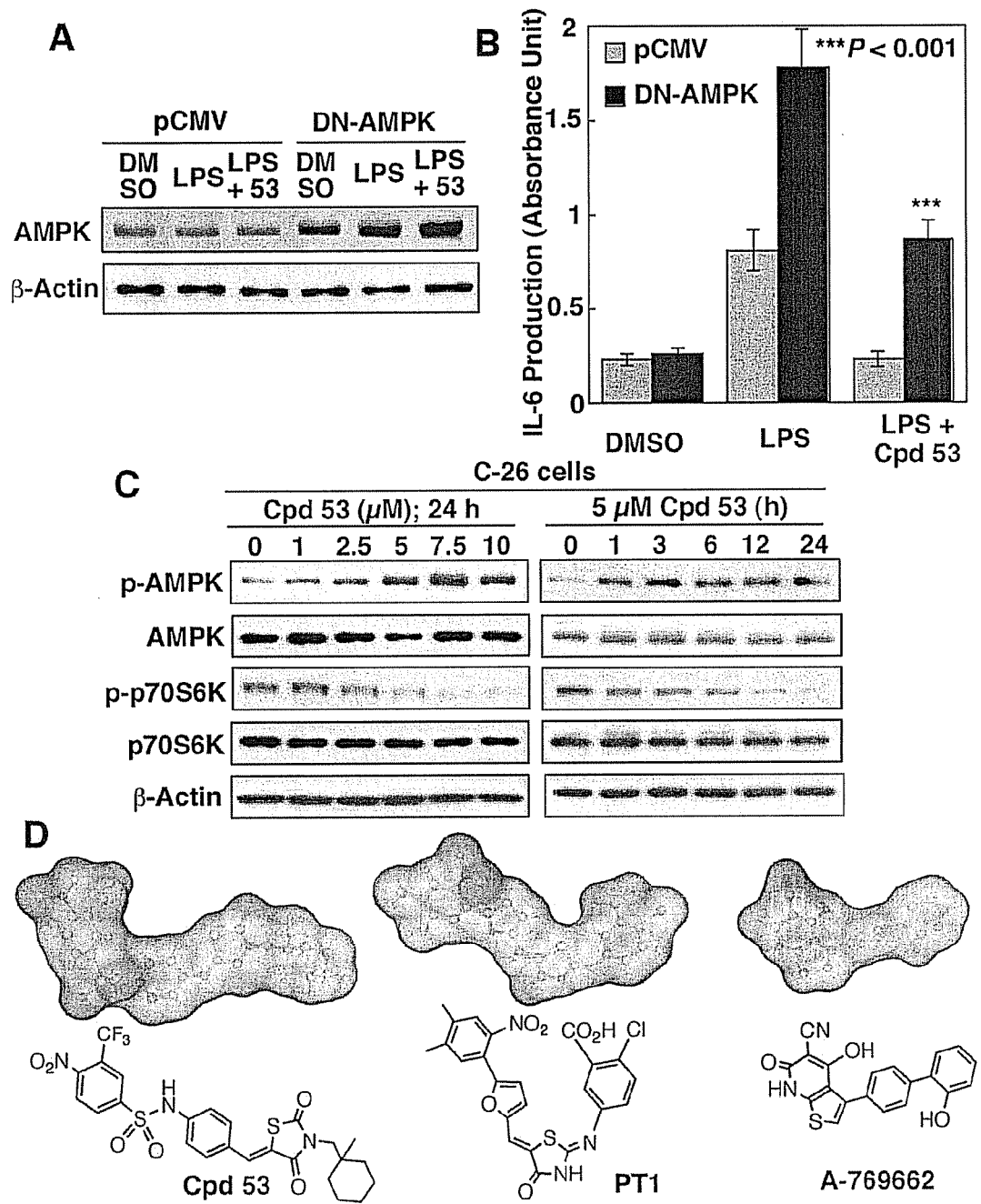

FIG. 18; section (A) provides a Western blot analysis of the expression levels of AMPK in THP-1 macrophages transiently transfected with the dominant negative (DN)-AMPK plasmid or pCMV empty vector. Section (B) shows the protective effect of ectopic expression of DN-AMPK on LPS-stimulated IL-6 production in THP-1 macrophages with or without co-treatment with 10 μM compound 53. Columns, mean; bars, SD (N=3). Section (C) shows the Western blot analysis of the dose- and time-dependent effects of compound 53 on the phosphorylation levels of AMPK and p70S6K in C-26 adenocarcinoma cells in 10% FBS-containing medium. Section (D) shows the surface electrostatic potentials and structures of compound 53 versus PT1 and A-769662.

Figure 19:
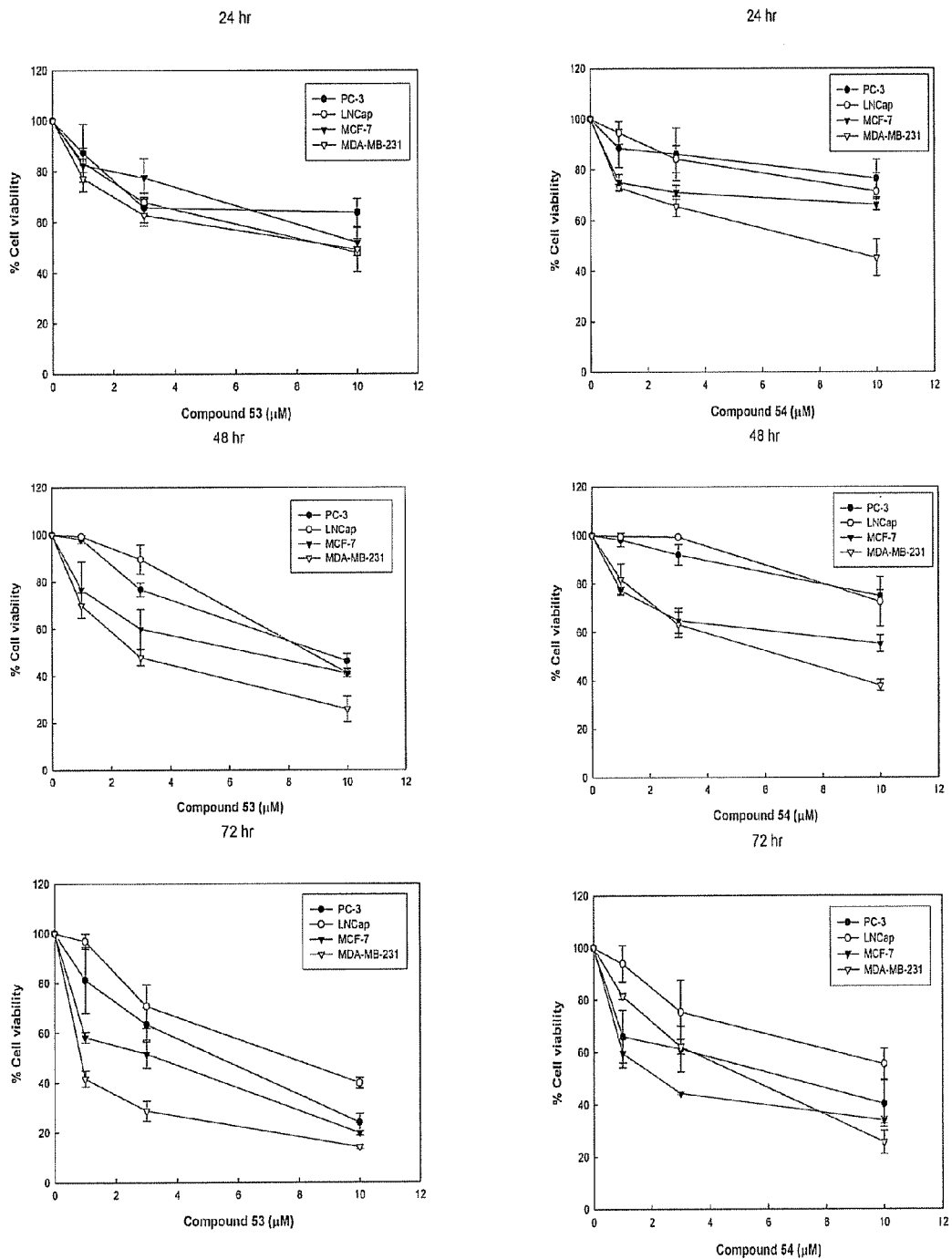

FIG. 19 provides graphs showing the cell viability of compounds 53 and 54 in different cancer cell lines.

DETAILED DESCRIPTION OF THE INVENTION

The present invention provides a method of restricting energy metabolism in a subject that includes administering to the subject a pharmaceutical composition including a thiazolidinedione derivative. In particular, the present invention provides a method of inhibiting glycolysis in a subject that includes administering to the subject a pharmaceutical composition including a thiazolidinedione derivative according to formula I, formula II, formula III, or formula IV. The invention provides a number of thiazolidinedione derivatives that have not previously been used to restrict energy metabolism, many of which exhibit higher potency than prior art energy restriction mimetic agents.

In another aspect, the present invention provides a method of activating adenosine monophosphate-activated protein kinase (AMPK) by delivering an effective amount of a thiazolidinedione derivative. In particular, the present invention provides a method of activating AMPK by providing an effective amount of a thiazolidinedione derivative according to formula I, formula III, or formula IV. Because activation of AMPK results in the inhibition of IL-6, these thiazolidinedione derivatives can also be used in a method of inhibiting IL-6 expression in a subject by administering to the subject a pharmaceutical composition including a thiazolidinedione derivative according to formula I, III, or IV.

Definitions

The terminology as set forth herein is for description of the embodiments only and should not be construed as limiting of the invention as a whole. As used in the description of the invention and the appended claims, the singular forms "a", "an", and "the" are inclusive of their plural forms, unless contraindicated by the context surrounding such.

As used herein, the term "organic group" is used to mean a hydrocarbon group that is classified as an aliphatic group, cyclic group, or combination of aliphatic and cyclic groups (e.g., alkaryl and aralkyl groups). In the context of the present invention, suitable organic groups for thiazolidinediones of this invention are those that do not interfere with the energy restriction activity of the thiazolidinediones. In the context of the present invention, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Alkyl groups including 4 or fewer carbon atoms can also be referred to as lower alkyl groups. Alkyl groups can also be referred to by the number of carbon atoms that they include (i.e., $C_1$-$C_4$ alkyl groups are alky groups including 1-4 carbon atoms).

Cycloalkyl, as used herein, refers to an alkyl group (i.e., an alkyl, alkenyl, or alkynyl group) that forms a ring structure. Cyclic groups can be monocyclic or polycyclic and preferably have from 3 to 10 ring carbon atoms. A cycloalkyl group can be attached to the main structure via an alkyl group including 4 or less carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like. Halo moieties include chlorine, bromine, fluorine, and iodine.

The term "aryl" as used herein includes carbocyclic aromatic rings or ring systems. Examples of aryl groups include phenyl, naphthyl, biphenyl, fluorenyl and indenyl. Aryl groups may be substituted or unsubstituted.

Unless otherwise indicated, the term "heteroatom" refers to the atoms O, S, or N. The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The terms "arylene" and "heteroarylene" are the divalent forms of the "aryl" and "heteroaryl" groups defined above. The terms "arylenyl" and "heteroarylenyl" are used when "arylene" and "heteroarylene", respectively, are substituted. For example, an alkylarylenyl group comprises an arylene moiety to which an alkyl group is attached.

When a group is present more than once in any formula or scheme described herein, each group (or substituent) is independently selected, whether explicitly stated or not. For example, for the formula —C(O)—NR$_2$ each R group is independently selected.

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, cyanoalkyls, etc. On the other hand, the phrase "alkyl moiety" is limited to the inclusion of only pure open chain saturated hydrocarbon alkyl substituents, such as methyl, ethyl, propyl, tert-butyl, and the like.

The invention is inclusive of the compounds described herein in any of their pharmaceutically acceptable forms, including isomers (e.g., diastereomers and enantiomers), tautomers, salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

The term thiazolidinedione derivatives, as used herein, is a shorthand for the thiazolidinedione compounds of the invention, as described by the formulas provided herein; and is not meant to encompass all possible compounds that might be characterized as a thiazolidinedione by one skilled in the art.

"Treat", "treating", and "treatment", etc., as used herein, refer to any action providing a benefit to a subject at risk for or afflicted with a condition or disease such as cancer, including improvement in the condition through lessening or suppression of at least one symptom, delay in progression of the disease, prevention or delay in the onset of the disease, etc. The subject may be at risk due to exposure to carcinogenic agents, being genetically predisposed to disorders involving glycolysis, and so on.

"Pharmaceutically acceptable" as used herein means that the compound or composition is suitable for administration to a subject for the methods described herein, without unduly deleterious side effects in light of the severity of the disease and necessity of the treatment.

The terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses. An effective amount, on the other hand, is an amount sufficient to provide a significant chemical effect, such as the activation of AMPK by a detectable amount.

Restricting Energy Metabolism Using Thiazolidinedione Derivatives

The invention provides a method of restricting energy metabolism in a subject by administering to the subject one or more thiazolidinedione derivatives of the invention. In particular, the invention provides a method of inhibiting glycolysis in a subject by administering to the subject a pharmaceutical composition including one or more thiazolidinedione derivatives.

A subject, as defined herein, is an animal, preferably a mammal such as a domesticated farm animal (e.g., cow, horse, pig) or pet (e.g., dog, cat). More preferably, the subject is a human. The subject may also be a subject in need of energy restriction. A subject in need of energy restriction is a subject that would benefit from energy restriction due to the various biochemical effects caused by energy restriction. For example, a subject needing decreased metabolic stress can be a subject in need of energy restriction. Additional effects caused by energy restriction are described herein. A subject in need of energy restriction can also be a subject that has an elevated risk for or has been diagnosed as having cancer, a subject that has not been diagnosed with cancer, a subject with diabetes, a subject with metabolic disorder, or a subject desiring an increased lifespan and/or a lower metabolic level.

The restriction of energy metabolism refers to an effect that can be produced, for example, by dietary energy restriction, such as limited calorie intake (i.e., caloric restriction). Dietary energy restriction results in reduced glucose availability, resulting in a decrease in glucose metabolism and glycolysis. Glycolysis is a series of metabolic processes by which one molecule of glucose is catabolized to two molecules of pyruvate to provide a net gain of two ATP molecules. In normal cells, glycolysis provides the initial step of cellular energy production and is a precursor to the tricarboxylic acid cycle, which is carried out in the mitochondria and generates a substantially larger amount of ATP per glucose molecule.

Restriction of energy metabolism can also be mimicked by administering suitable compounds, referred to as energy restriction mimetic agents. For example, 2-deoxyglucose can restrict energy metabolism as a result of being phosphorylated by hexokinase, which is then trapped in the phosphorylated state which accumulates and prevents further glucose metabolism. The experiments carried out by the inventors and described herein demonstrate that thiazolidinedione derivatives of the invention are able to elicit starvation-associated cellular responses such as silent information regulator 1 (Sirt1) gene induction, AMPK activation, and endoplasmic reticulum stress. Because the thiazolidinedione derivatives are able to elicit starvation-associated cellular responses, and for other reasons provided herein, the thiazolidinedione derivatives are effective energy restriction mimetic agents (ERMs).

Inhibition of glycolysis results in the restriction of energy metabolism. Glycolysis is the metabolic pathway that converts glucose into pyruvate, resulting in the release of the high energy compounds, ATP and NADH. Any amount of decrease in the normal level of glycolysis represents a restriction of energy metabolism with respect to the invention described herein. However, different embodiments of the invention may result in varying levels of inhibition. For example, administering a thiazolidinedione derivative can result in a 10%, 20%, 30%, 40%, 50%, 60%, 70%, 80%, 90%, or complete inhibition of glycolysis, or any other significant level of inhibition within this range of numbers. The level of inhibition achieved can vary with the dose of thiazolidinedione derivative used, and is therefore dose dependent. While high levels of glycolysis inhibition can be achieved, it should be noted that more moderate levels, i.e., 50% inhibition or less, is generally more clinically useful as this avoids the potential toxicity of high levels of glycolysis inhibition.

Figure 1:
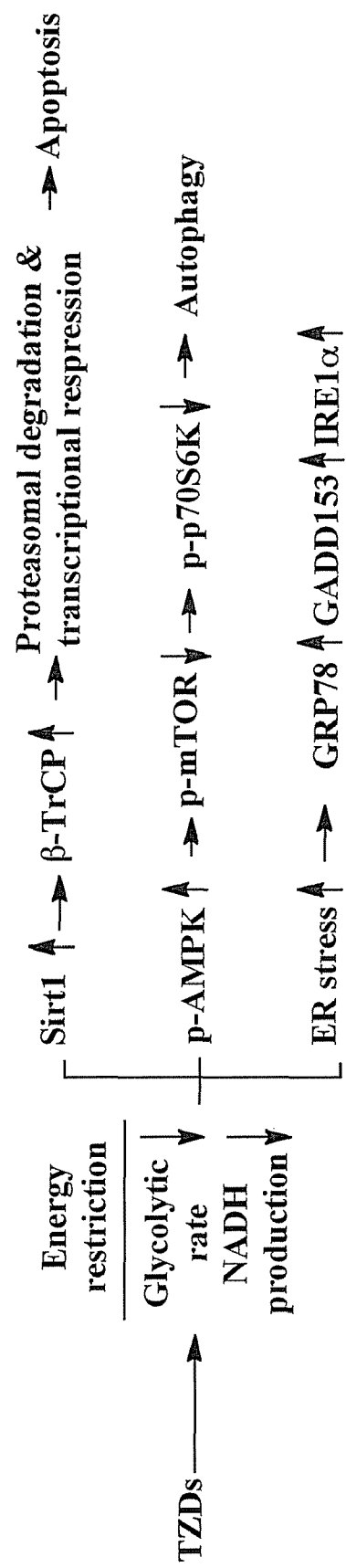
FIG. 1 provides a schematic diagram depicting the various factors affected by thiazolidinediones (TZDs) that result in their ability to act as energy restriction-mimetic agents.

While the inhibition of glycolysis can be measured using a variety of different compounds and effects known to those skilled in the art, examples of markers that are commonly used to measure decreases in glycolysis are the decreased rate of glucose uptake by cells, decreases in the formation of NADH and lactate, and an increase in autophagy, which can be identified by a corresponding increase in autophagosome formation. These and other effects of the thiazolidinedione derivatives of the invention are represented schematically in FIG. 1.

The thiazolidinedione derivatives of the present invention disrupt glucose homeostasis, resulting in the hallmark cellular responses, including transient Sirt1 induction, AMPK activation, and ER stress. Each of these responses plays a role in mediating the antitumor effects of the TZDs. The inventor's data indicate a mechanistic link between Sirt1 induction and β-TrCP protein accumulation, culminating in apoptosis through the proteasomal degradation and transcriptional repression of a series of apoptosis-regulatory proteins. The AMPK activation results in autophagy via the conventional AMPK-TSC2-mTOR-p70S6K pathway. The ER stress signal triggers the up-regulation of sensor proteins, such as GRP78, GADD153 and IRE1α, which, may also play a role in apoptosis induction.

The inhibition of glycolysis in a subject can have one or more beneficial effects. For example, inhibition of glycolysis in a subject can provide a method of treating cancer. Inhibition of glycolysis can also be used in subjects to increase longevity (i.e., provide a prolongevity effect), including subjects that have not been diagnosed as having cancer. The inhibition of glycolysis can also be carried out to provide any of the other effects known to those skilled in the art, such as reducing insulin levels, treating metabolic disorder, or stimulating autophagy.

The ability of various thiazolidinedione derivatives to inhibit cancer growth is demonstrated in table I below. The compounds were tested for their ability to decrease LNCaP prostate cancer cell viability as measured by the 3-(4,5-dimethylthiazol-2-yl)-2,5-diphenyltetrazolium bromide) (MTT) assay. The compounds tested showed significantly higher activity (i.e., a lower $IC_{50}$) than known energy restriction mimetic agents such as 2-DG or resveratrol. The $IC_{50}$ values of many thiazolidinedione derivatives for inhibiting cancer cell proliferation were in the low-μM range, which are at least one- to three orders of magnitude more potent than resveratrol and 2-deoxyglucose, respectively.

TABLE I

Antitumor potency of Thiazolidinedione derivatives

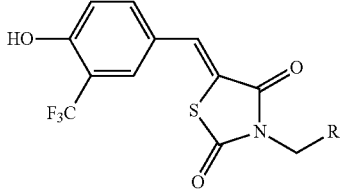

R group and respective $IC_{50}$ in inhibiting LNCaP cell viability (μM)

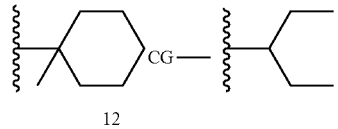

| 5.6 | 3.7 | 4.2 | 4.0 | 4.5 | 4.5 |

As noted herein, malignant cells exhibit significantly elevated glycolytic activity relative to normal cells, an effect referred to as the Warburg effect. Several mechanisms have been suggested to contribute to this effect, including mitochondrial defects, adaptation to the hypoxic environment in cancer tissues, oncogenic signals, and the abnormal expression of certain metabolic enzymes. Because the ability of cancer cells to use the mitochondrial respiratory machinery to generate ATP is reduced, cancer cells are forced to increase their glycolytic activity to maintain sufficient ATP generation for continued growth. This metabolic adaptation renders the cancer cells dependent on the glycolytic pathway and vulnerable to its inhibition. Furthermore, since this metabolic alternation is nearly ubiquitous in cancer cells, targeting the glycolytic pathway represents a useful method for treating a wide variety of different types of cancer. For further discussion of the use of glycolysis inhibition for anticancer treatment, see Pelicano et al., Oncogene, 25, p. 4633-4646 (2006).

When glycolysis is inhibited, the intact mitochondria in normal cells enable them to use alternative energy sources such as fatty acids and amino acids to produce metabolic intermediates which are channeled to the tricarboxylic acid cycle for ATP production through respiration. As a result, cells with normal mitochondria are less sensitive to agents that inhibit glycolysis, relative to cancer cells, providing therapeutic selectivity. Accordingly, the invention provides a method of treating cancer using thiazolidinedione derivatives as a result of their ability to selectively inhibit glycolysis in cancer cells.

The effectiveness of cancer treatment may be measured by evaluating a reduction in tumor load or decrease in tumor growth in a subject in response to the administration of the thiazolidinedione derivative. The reduction in tumor load may be represent a direct decrease in mass, or it may be measured in terms of tumor growth delay, which is calculated by subtracting the average time for control tumors to grow over to a certain volume from the time required for treated tumors to grow to the same volume.

Thiazolidinedione derivatives can be used to both treat and prevent cancer. As used herein, the term "prevention" includes either preventing the onset of a clinically evident unwanted cell proliferation altogether or preventing the onset of a preclinically evident stage of unwanted rapid cell proliferation in individuals at risk. Also intended to be encompassed by this definition is the prevention of metastasis of malignant cells or to arrest or reverse the progression of malignant cells. This includes prophylactic treatment of those having an enhanced risk of developing precancers and cancers. An elevated risk represents an above-average risk that a subject will develop cancer, which can be determined, for example, through family history or the detection of genes causing a predisposition to developing cancer.

Cancer cells contain genetic damage that has resulted in the relatively unrestrained growth of the cells. The genetic damage present in a cancer cell is maintained as a heritable trait in subsequent generations of the cancer cell line. The cancer treated by the method of the invention may be any of the forms of cancer known to those skilled in the art or described herein. Cancer that manifests as both solid tumors and cancer that instead forms non-solid tumors as typically seen in leukemia can be treated. Based on the prevalence of an increase in aerobic glycolysis in all types of cancer, the present invention provide methods for treating a subject that is afflicted with various different types of cancers, including carcinoma, sarcoma, and lymphoma.

The inventors have demonstrated that thiazolidinedione derivatives can be used to inhibit the growth of a variety of different types of cancer cells. For example, experiments have been carried out demonstrating the effectiveness of thiazolidinedione derivatives for inhibiting the growth of prostate cancer, breast cancer, leukemia, non-small cell lung cancer, colon cancer, CNS cancer, melanoma, ovarian cancer, and renal cancer cells. These experiments are described in Example 2, provided later herein.

Inhibition of glycolysis by thiazolidinedione derivatives can also be used to treat type II diabetes or metabolic syndrome. Metabolic syndrome, as defined herein, is a combination of disorders that can lead to an increased risk of developing heart disease or diabetes, and is characterized by a plurality of symptoms selected from fasting hyperglycemia, as seen in diabetes mellitus type 2 or impaired fasting glucose, impaired glucose tolerance, or insulin resistance; high blood pressure; central obesity with fat deposits mainly around the waist; decreased HDL cholesterol; and elevated triglycerides. Thiazolidinedione derivatives can be used to treat or prevent type II diabetes or metabolic syndrome by delivering a therapeutically effective amount of a thiazolidinedione derivative in a pharmaceutical composition to a subject in need thereof. Thiazolidinedione derivatives are effective as a result of their affect on glycolysis, as described herein, and also as a result of their effect on AMPK. The AMPK system is known to act, as a sensor of cellular energy status in eukaryotic cells, and has an important effect on metabolic control and insulin signaling. Towler et al., Circ Res, 100, 328-341 (2007).

Another potential benefit to providing energy metabolism restriction in a subject by administering thiazolidinedione derivatives is that it can extend the lifespan of a subject so treated, thereby providing a prolongevity effect. Reproducible longevity studies in laboratory rats and mice have demonstrated that energy restriction can significantly increase the life span and delay the onset of age-related disease. A similar effect has been seen in numerous invertebrate species, and recent studies in primates have shown that energy restriction produces physiological effects that parallel those observed in rodents. Research has also been carried out to evaluate the effect of energy restriction mimetic agents on lifespan. See Ingram et al., Ann N Y Acad. Sci., 1019 p. 412-23 (2004).

Several mechanisms have been proposed for the prolongevity effect of energy restriction mimetics, including reduced oxidative stress, control of inflammation, and protection against the glycation of macromolecules. In particular, it has been noted that in inhibition of glycolysis can stimulate autophagy which can result in the scavenging of organelles releasing significant amounts of reactive oxygen species. It has further been hypothesized that the prolongevity effect of energy restriction may be an evolutionarily conserved stress response that redirects an organism's energy towards survival rather than reproduction during times of low energy availability.

A prolongevity effect is one that increases the average lifespan of subjects treated with a therapeutically effective dose of the energy restriction mimetic agent when compared with untreated subjects. While a prolongevity effect can also be achieved in subjects diagnosed with a disease such as cancer, a prolongevity effect can be obtained in healthy subjects because the effect is not dependent on the removal of disease. Because the prolongevity effect is seen as the result of preventing chronic problems such as oxidative stress or inflammation, subjects must be treated for an extended period in order for significant prolongevity effects to be seen. Based on the results seen in mice, the prolongevity effect may provide a 10%, 20%, 30%, or 40% increase in lifespan. Mattson, M. P., Annu. Rev. Nutr. 25: p. 237-60 (2005).

A prolongevity effect can be provided in subjects that have been diagnosed to be healthy, or subjects that have not been diagnosed as having a disease or disorder. For example, a prolongevity effect can be provided in subjects that have been diagnosed as being free of cancer, or subjects that have not been diagnosed with cancer. Methods for diagnosing cancer are well known by those skilled in the art.

As part of their effort to investigate the activity of numerous thiazolidinedione derivatives, the inventors conducted a screening of an in-house, thiazolidinedione-based focused compound library to identify compounds with the ability to mediate peroxisome proliferator-activated receptor (PPAR)γ-independent activation of adenosine monophosphate-activated protein kinase (AMPK) and suppression of interleukin (IL)-6 production. Cell-based assays pertinent to the activation status of AMPK and mammalian homolog of target of rapamycin (i.e., phosphorylation of AMPK and p70 ribosomal protein S6 kinase, respectively), and IL-6/IL-6 receptor signaling (i.e., IL-6 production and signal transducer and activator of transcription 3 phosphorylation, respectively) in lipopolysaccharide (LPS)-stimulated THP-1 human macrophages were used to screen this compound library, which led to the identification of various active thiazolidinedione derivatives, with compound 53 (N-{4-[3-(1-Methyl-cyclohexylmethyl)-2,4-dioxo-thiazolidin-5-ylidene-methyl]phenyl}-4-nitro-3-trifluoro-methyl-benzenesulfonamide) being identified as the lead agent. Evidence described in the examples herein indicates that the suppression IL-6 production was attributable to AMPK activation. Thiazolidinedione derivative-mediated AMPK activation was also demonstrated in C-26 colon adenocarcinoma cells, indicating that the effect is not cell line-specific. AMPK represents a therapeutically relevant target for the treatment of Type II diabetes, the metabolic syndrome, and cancer, further supporting the use of thiazolidinedione derivatives as energy restriction mimetic agents.

Accordingly, a further aspect of the invention provides a method of activating adenosine monophosphate-activated protein kinase by providing an effective amount of a thiazolidinedione derivative. In addition, another aspect of the invention provides a method of inhibiting IL-6 expression in a subject by administering to the subject a pharmaceutical composition including a one of the thiazolidinedione derivatives described herein as being effective as an AMPK activator.

Thiazolidinedione Derivatives

The thiazolidinedione derivatives of the present invention include the compounds of Formula's I, II, III, and IV. For instance, the thiazolidinedione derivatives can be compounds having formula I:

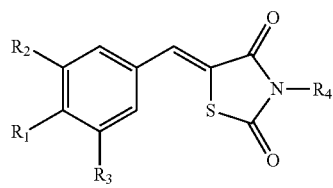

I wherein $R_1$ is hydrogen or hydroxyl; wherein $R_2$ and $R_3$ are selected from hydrogen, hydroxyl, halo, amino, methyl, methoxy, ethyl, ethoxy, nitro, aminosulfonyl, trifluoromethylsulfonyl, and haloalkyl moieties; and wherein $R_4$ is selected from alkyl, alkenyl, cycloalkyl, and aryl groups. In particular embodiments of the invention, $R_1$ is hydroxyl. In further embodiments, $R_2$ is trifluoromethyl, while in yet further embodiments $R_3$ is hydrogen.

In further embodiments, the thiazolidinedione derivative of formula I can be any of the compounds shown below. For example, the thiazolidinedione derivative can be any of the following compounds:

(Z)-5-(4-Hydroxy-3-trifluoromethyl-benzylidene)-3-(1-methyl-cyclohexylmethy)-thiazolidine-2-4-dione (OSU-CG12):

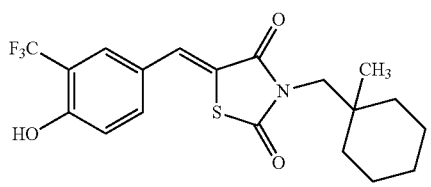 [SMILES: CC1(CN2C(=O)S/C(=C\c3ccc(O)c(C(F)(F)F)c3)C2=O)CCCCC1]

(Z)-3-(2-Ethyl-butyl)-5-(4-hydroxy-3-trifluoromethyl-benzylidene)-thiazolidine-2-4-dione (OSU-CG5):

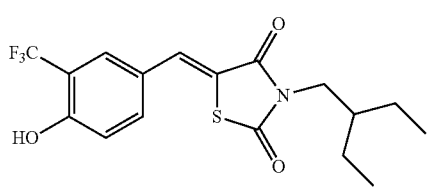 [SMILES: CCC(CC)CN1C(=O)S/C(=C\c2ccc(O)c(C(F)(F)F)c2)C1=O]

(Z)-3-(2-Ethyl-pentyl)-5-(4-hydroxy-3-trifluoromethyl-benzylidene)-thiazolidine-2-4-dione:

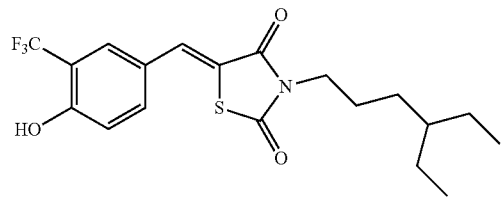 [SMILES: CCC(CC)CCCN1C(=O)S/C(=C\c2ccc(O)c(C(F)(F)F)c2)C1=O]

(Z)-5-(4-Hydroxy-3-trifluoromethyl-benzylidene)-3-(4-isopropyl-benzyl)-thiazolidine-2-4-dione:

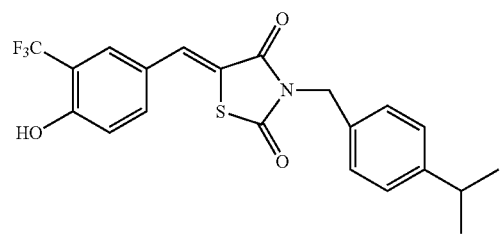 [SMILES: CC(C)c1ccc(CN2C(=O)S/C(=C\c3ccc(O)c(C(F)(F)F)c3)C2=O)cc1]

(Z)-3-(4-tert-Butyl-benzyl)-5-(4-hydroxy-3-trifluoromethyl-benzylidene)-thiazolidine-2-4-dione:

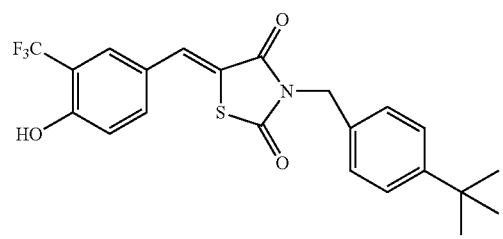 [SMILES: CC(C)(C)c1ccc(CN2C(=O)S/C(=C\c3ccc(O)c(C(F)(F)F)c3)C2=O)cc1]

(Z)-5-(4-Hydroxy-3-trifluoromethyl-benzylidene)-3-(2-trifluoromethyl-benzyl)-thiazolidine-2-4-dione:

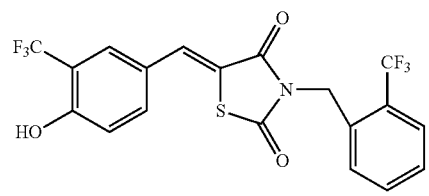 [SMILES: O=C1S/C(=C\c2ccc(O)c(C(F)(F)F)c2)C(=O)N1Cc1ccccc1C(F)(F)F]

(Z)-3-Cyclohexylmethyl-5-(4-hydroxy-3-trifluoromethyl-benzylidene)-thiazolidine-2-4-dione:

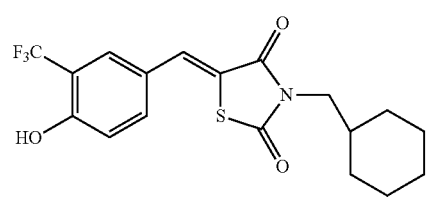 [SMILES: O=C1S/C(=C\c2ccc(O)c(C(F)(F)F)c2)C(=O)N1CC1CCCCC1]

(Z)-3-Benzyl-5-(4-hydroxy-3-trifluoromethyl-benzylidene)-thiazolidine-2-4-dione:

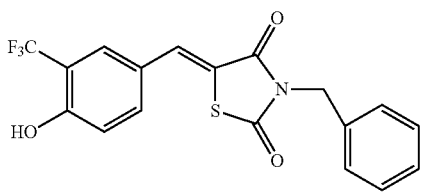 [SMILES: O=C1S/C(=C\c2ccc(O)c(C(F)(F)F)c2)C(=O)N1Cc1ccccc1]

(Z)-3-Cycloheptylmethyl-5-(4-hydroxy-3-trifluoromethyl-benzylidene)-thiazolidine-2-4-dione:

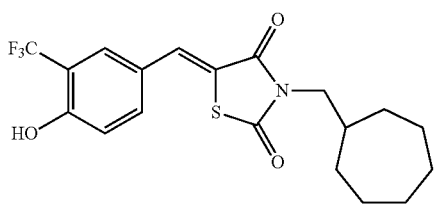 [SMILES: O=C1S/C(=C\c2ccc(O)c(C(F)(F)F)c2)C(=O)N1CC1CCCCCC1]

(Z)-5-(4-Hydroxy-3-trifluoromethyl-benzylidene)-3-isobutyl-thiazolidine-2-4-dione:

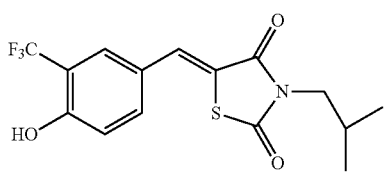 [SMILES: CC(C)CN1C(=O)S/C(=C\c2ccc(O)c(C(F)(F)F)c2)C1=O]

In other embodiments of the invention, the thiazolidinedione derivatives of formula I are defined such that $R_1$ is hydroxyl, $R_2$ is trifluoromethyl, and $R_3$ is hydroxyl. By varying $R_4$ of formula I, the thiazolidinedione derivatives shown below are provided.

(Z)-5-(3,4-Dihydroxy-5-trifluoromethyl-benzylidene)-3-(1-methyl-cyclohexylmethy)-thiazolidine-2-4-dione:

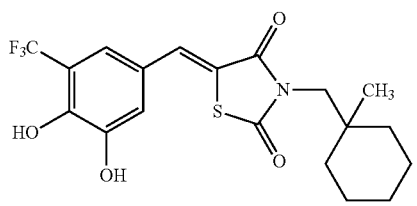 [SMILES: CC1(CN2C(=O)S/C(=C\c3cc(O)c(O)c(C(F)(F)F)c3)C2=O)CCCCC1]

(Z)-5-(3,4-Dihydroxy-5-trifluoromethyl-benzylidene)-3-(2-ethyl-butyl)-thiazolidine-2-4-dione:

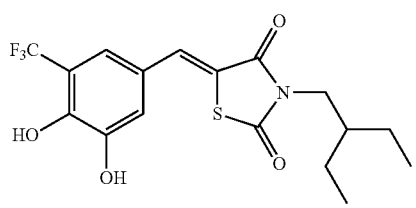 [SMILES: CCC(CC)CN1C(=O)S/C(=C\c2cc(O)c(O)c(C(F)(F)F)c2)C1=O]

(Z)-5-(3,4-Dihydroxy-5-trifluoromethyl-benzylidene)-3-(2-ethyl-pentyl)-thiazolidine-2-4-dione:

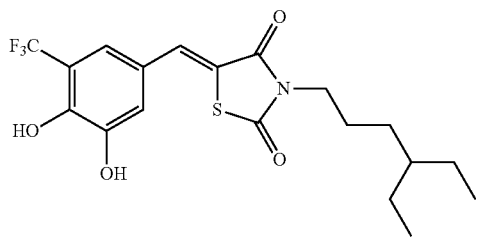 [SMILES: CCC(CC)CCCN1C(=O)S/C(=C\c2cc(O)c(O)c(C(F)(F)F)c2)C1=O]

(Z)-5-(3,4-Dihydroxy-5-trifluoromethyl-benzylidene)-3-(4-isopropyl-benzyl)-thiazolidine-2-4-dione:

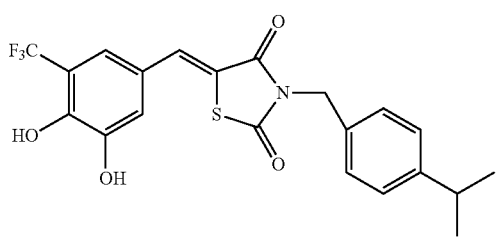 [SMILES: CC(C)c1ccc(CN2C(=O)S/C(=C\c3cc(O)c(O)c(C(F)(F)F)c3)C2=O)cc1]

(Z)-3-(4-tert-Butyl-benzyl)-5-(3,4-dihydroxy-5-trifluoromethyl-benzylidene)-thiazolidine-2-4-dione:

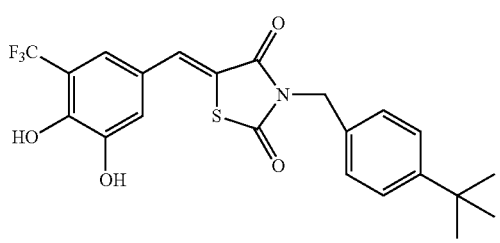 [SMILES: CC(C)(C)c1ccc(CN2C(=O)S/C(=C\c3cc(O)c(O)c(C(F)(F)F)c3)C2=O)cc1]

(Z)-5-(3,4-Dihydroxy-5-trifluoromethyl-benzylidene)-3-(2-trifluoromethyl-benzyl)-thiazolidine-2-4-dione:

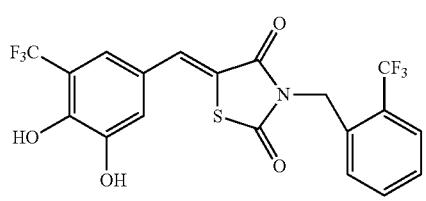 [SMILES: O=C1S/C(=C\c2cc(O)c(O)c(C(F)(F)F)c2)C(=O)N1Cc1ccccc1C(F)(F)F]

(Z)-3-Cyclohexylmethyl-5-(3,4-dihydroxy-5-trifluoromethyl-benzylidene)-thiazolidine-2-4-dione:

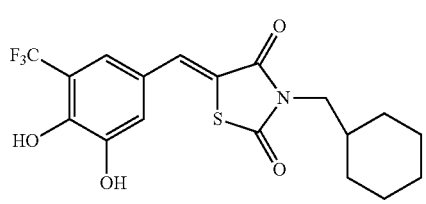 [SMILES: O=C1S/C(=C\c2cc(O)c(O)c(C(F)(F)F)c2)C(=O)N1CC1CCCCC1]

(Z)-3-Benzyl-5-(3,4-dihydroxy-5-trifluoromethyl-benzylidene)-thiazolidine-2-4-dione:

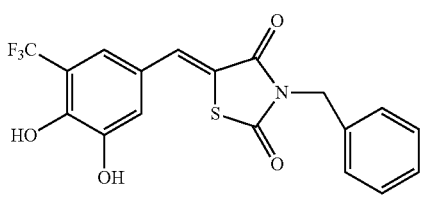 [SMILES: O=C1S/C(=C\c2cc(O)c(O)c(C(F)(F)F)c2)C(=O)N1Cc1ccccc1]

(Z)-3-Cycloheptylmethyl-5-(3,4-dihydroxy-5-trifluoromethyl-benzylidene)-thiazolidine-2-4-dione:

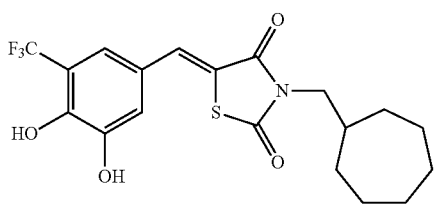 [SMILES: O=C1S/C(=C\c2cc(O)c(O)c(C(F)(F)F)c2)C(=O)N1CC1CCCCCC1]

(Z)-5-(3,4-Dihydroxy-5-trifluoromethyl-benzylidene)-3-isobutyl-thiazolidine-2-4-dione:

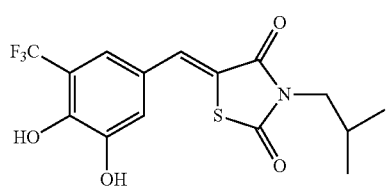 [SMILES: CC(C)CN1C(=O)S/C(=C\c2cc(O)c(O)c(C(F)(F)F)c2)C1=O]

In other embodiments of the invention, the thiazolidinedione derivatives of formula I are defined such that $R_1$ is hydrogen and $R_2$ and $R_3$ are halo moieties. In a further embodiment, $R_2$ and $R_3$ are both bromo moieties. By varying $R_4$ of formula I for this embodiment, the thiazolidinedione derivatives shown below are provided.

(Z)-5-(3,5-Dibromo-benzylidene)-3-(1-methyl-cyclohexylmethy)-thiazolidine-2-4-dione:

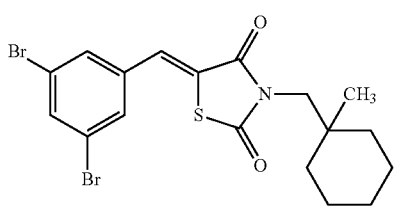 [SMILES: CC1(CN2C(=O)S/C(=C\c3cc(Br)cc(Br)c3)C2=O)CCCCC1]

(Z)-5-(3,5-Dibromo-benzylidene)-3-(2-ethyl-butyl)-thiazolidine-2-4-dione:

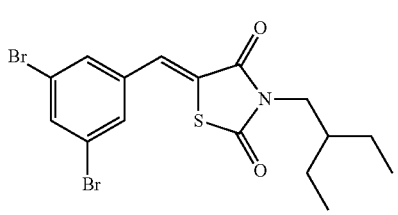 [SMILES: CCC(CC)CN1C(=O)S/C(=C\c2cc(Br)cc(Br)c2)C1=O]

(Z)-5-(3,5-Dibromo-benzylidene)-3-(2-ethyl-pentyl)-thiazolidine-2-4-dione:

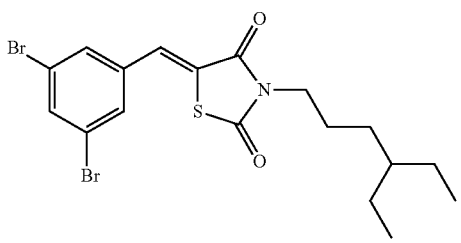 [SMILES: CCC(CC)CCCN1C(=O)S/C(=C\c2cc(Br)cc(Br)c2)C1=O]

(Z)-5-(3,5-Dibromo-benzylidene)-3-(4-isopropyl-benzyl)-thiazolidine-2-4-dione:

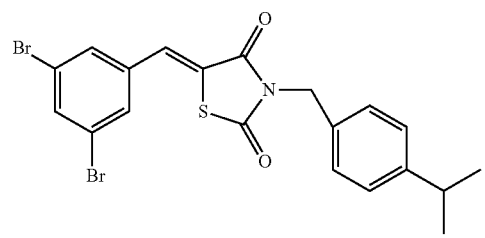 [SMILES: CC(C)c1ccc(CN2C(=O)S/C(=C\c3cc(Br)cc(Br)c3)C2=O)cc1]

(Z)-3-(4-tert-Butyl-benzyl)-5-(3,5-dibromo-benzylidene)-thiazolidine-2-4-dione:

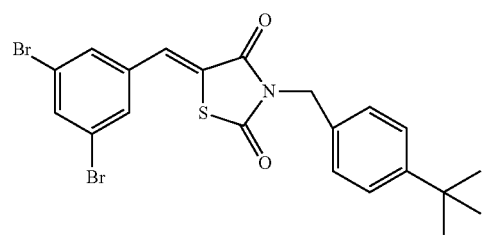 [SMILES: CC(C)(C)c1ccc(CN2C(=O)S/C(=C\c3cc(Br)cc(Br)c3)C2=O)cc1]

(Z)-5-(3,5-Dibromo-benzylidene)-3-(2-trifluoromethyl-benzyl)-thiazolidine-2-4-dione:

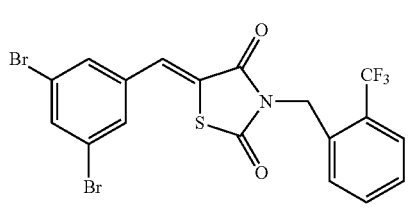 [SMILES: O=C1S/C(=C\c2cc(Br)cc(Br)c2)C(=O)N1Cc1ccccc1C(F)(F)F]

(Z)-3-Cyclohexylmethyl-5-(3,5-dibromo-benzylidene)-thiazolidine-2-4-dione:

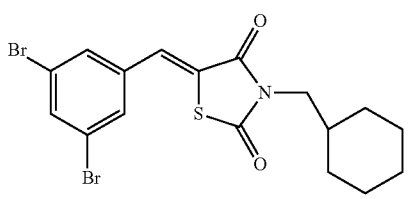 [SMILES: O=C1S/C(=C\c2cc(Br)cc(Br)c2)C(=O)N1CC1CCCCC1]

(Z)-3-Benzyl-5-(3,5-dibromo-benzylidene)-thiazolidine-2-4-dione:

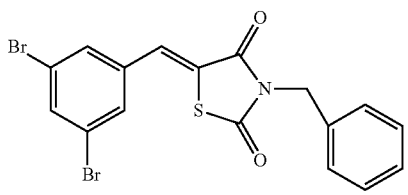 [SMILES: O=C1S/C(=C\c2cc(Br)cc(Br)c2)C(=O)N1Cc1ccccc1]

(Z)-3-Cycloheptylmethyl-5-(3,5-dibromo-benzylidene)-thiazolidine-2-4-dione:

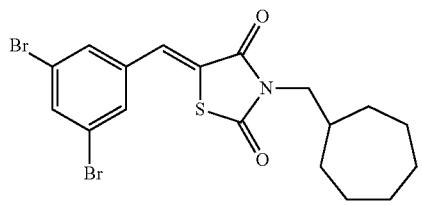 [SMILES: O=C1S/C(=C\c2cc(Br)cc(Br)c2)C(=O)N1CC1CCCCCC1]

(Z)-5-(3,5-dibromo-benzylidene)-3-isobutyl-thiazolidine-2-4-dione:

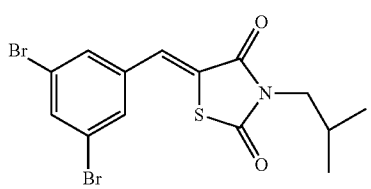 [SMILES: CC(C)CN1C(=O)S/C(=C\c2cc(Br)cc(Br)c2)C1=O]

In another aspect of the invention, the thiazolidinedione derivatives can be compounds having formula II:

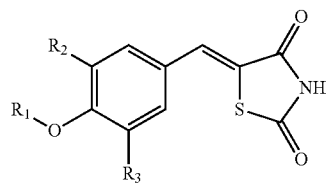

II wherein $R_1$ is selected from aryl, alkyl, heteroaryl, cycloalkyl, and heterocycloalkyl groups; wherein $R_2$ is selected from hydrogen, halo, and nitro moieties and alkyl, alkoxy, and haloalkyl groups; and wherein $R_3$ is selected from hydrogen and halo moieties and alkyl, alkoxy, and haloalkyl groups.

The thiazolidinedione derivatives of formula II can also, in some embodiments, have $R_1$ selected from

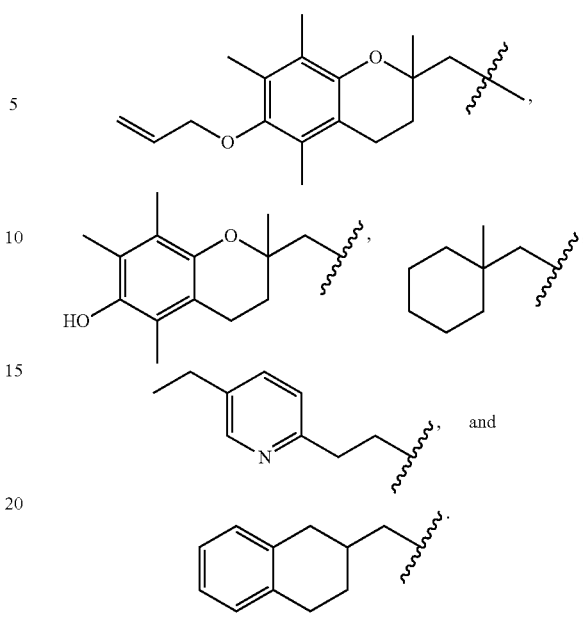

In additional embodiments, the thiazolidinedione derivatives of formula II are defined such that $R_2$ is selected from hydrogen, bromo, chloro, methyl, methoxy, ethoxy, and nitro; and $R_3$ is selected from hydrogen, methyl, methoxy, and bromo.

The thiazolidinedione derivative can also be compound STG28, which has the following structure:

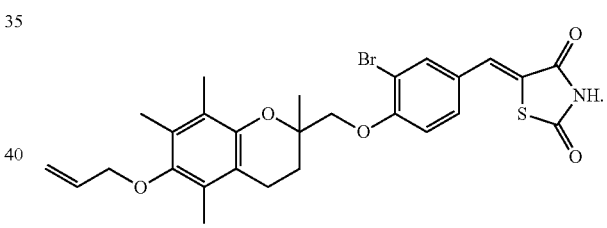

In further embodiments of the invention, the thiazolidinedione derivatives can be compounds having formula III:

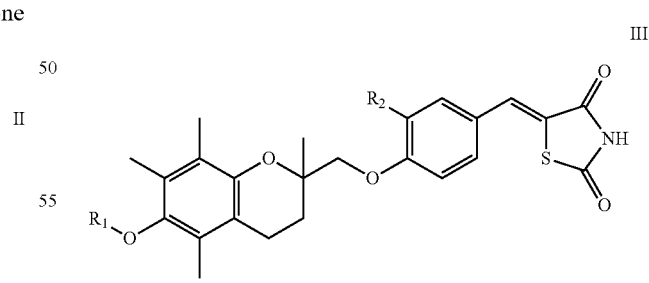

III wherein $R_1$ is lower alkyl group and $R_2$ is selected from halo, methyl, methoxy, ethyl moieties.

Examples of compounds according to formula III can be selected from the group consisting of 5-[3-Bromo-4-(6-ethoxy-2,5,7,8-tetramethyl-chroman-2-ylmethoxy)-benzylidene]-thiazolidine-2,4-dione, 5-[4-(6-Butoxy-2,5,7,8-tetramethyl-chroman-2-ylmethoxy)-3-methoxy-benzylidene]-thiazolidine-2,4-dione, and 4-{2-[2-Bromo-4-

(2,4-dioxo-thiazolidin-5-ylidenemethyl)-phenoxymethyl]-2,5,7,8-tetramethyl-chroman-6-yloxy}-butyronitrile.

In further embodiments of the invention, the thiazolidinedione derivatives can be compounds having formula IV:

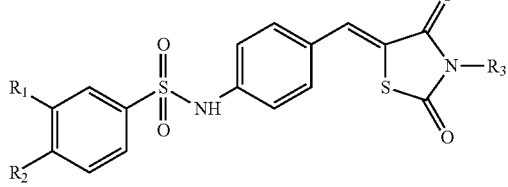

IV wherein $R_1$ is a hydrogen, methyl, or trifluormethyl moiety; $R_2$ is a methoxy or nitro moiety, and $R_3$ is an alkyl or cycloalkyl group.

Examples of compounds according to formula IV can be selected from the group consisting of 4-Methoxy-N-{4-[3-(1-methyl-cyclohexylmethyl)-2,4-dioxo-thiazolidin-5-ylidenemethyl]-phenyl}-benzenesulfonamide, N-{4-[3-(1-Methyl-cyclohexylmethyl)-2,4-dioxo-thiazolidin-5-ylidenemethyl]-phenyl}-4-nitro-3-trifluoromethyl-benzene sulfonamide, and N-{4-[3-(1-Methyl-cyclohexylmethyl)-2,4-dioxo-thiazolidin-5-ylidenemethyl]-phenyl}-4-nitro-benzenesulfonamide.

A number of the thiazolidinedione derivatives of the present invention exhibit the capability of activating AMPK. In particular, compounds of formulas I, III, and IV have been shown to be capable of activating AMPK. While these compounds have many of the same overall formulas used to describe compounds useful as energy restriction mimetic agents, the substituents for the compounds of these formulas may differ. Accordingly, thiazolidinedione derivative can be compounds according to formula III:

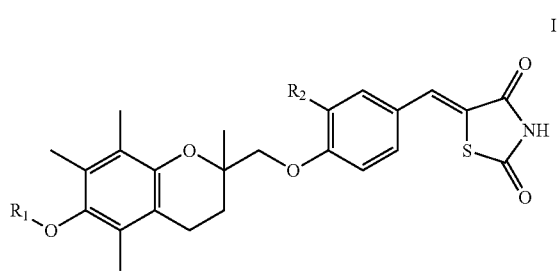

III wherein $R_1$ is lower alkyl group and $R_2$ is selected from halo, methyl, methoxy, ethyl moieties; compounds of formula I:

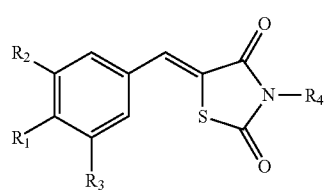

I wherein $R_1$ is hydroxyl; wherein $R_2$ is trifluoromethyl; wherein $R_3$ is hydrogen; and wherein $R_4$ is an alkyl or cycloalkyl groups; and compounds of formula IV:

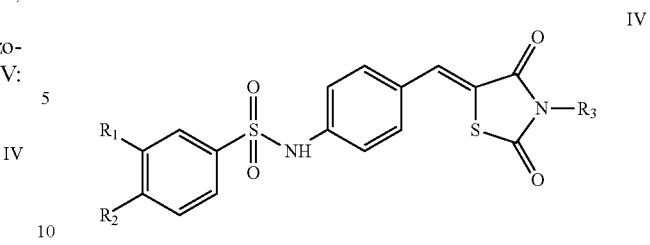

IV wherein $R_1$ is a hydrogen, methyl, or trifluormethyl moiety; $R_2$ is a methoxy or nitro moiety, and $R_3$ is an alkyl or cycloalkyl group.

A particularly preferred compound for activating AMPK is compound 53, which has the following structure:

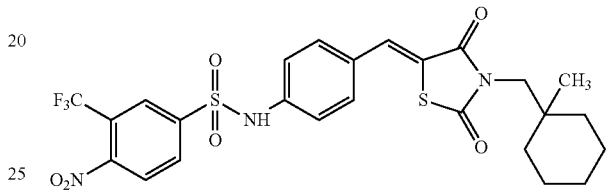

Identification of Thiazolidinedione Derivatives

An additional aspect of the invention includes methods for identifying thiazolidinedione derivatives that may be used to restrict energy metabolism in a subject. Potential agents suitable for testing are referred to herein as "candidate agents." A variety of different assays can be used to identify the ability of an agent to restrict energy metabolism. For example, the ability of the compound to reduce glucose uptake, the glycolytic rate, or the production of NADH and lactate can be measured. Alternately, or in addition, the ability of the compounds to elicit glucose starvation-like responses such as Sirt1 induction, AMPK activation, ER stress, or β-TrCP-mediated protein degradation can be measured. Procedures for carrying out these analysis are known to those skilled in the art, and many are described in Example 1 provided herein. Sources for candidate agents include, for instance, chemical compound libraries such as that shown in FIG. 2, or natural sources.

Candidate agents may also be tested in animal models. For example, the ability thiazolidinedione derivatives to inhibit cancer as a result of energy restriction can be evaluated in the C4-2 xenograft tumor model. The study of various cancers in animal models (for instance, mice) is a commonly accepted practice for the study of human cancers. However, candidate agents can also be evaluated in animal models for their pro-longevity effects. For example, body temperature and plasma insulin levels are both indicators for an energy restriction effect, and of course the lifespan of the animal models can be measured. Results are typically compared between control animals treated with candidate agents and the control littermates that did not receive treatment.

For example, C4-2 prostate cancer xenograft tumors can be established in castrated male NCr athymic nude mice (5-7 weeks old) by subcutaneous injection of $C_{4\text{-}2}$ cells suspended in equal volumes of serum-free medium and Matrigel ($2 \times 10^6$ cells/0.1 ml/mouse). When tumor volumes reach approximately 100 mm$^3$, mice are randomly assigned to experimental groups (10 mice/group). Thiazolidinedione derivatives are prepared for oral administration and administered once daily at 100%, 50%, 25% and 10% of their respective maximum tolerated dose by gavage for the duration of the study. As a control, resveratrol can be administered at 100 mg/kg once daily. Body weights and tumor sizes are measured weekly. When control tumors reach 1000 mm$^3$, the mice are sacrificed and tissues harvested for biomarker assessment. The ability of thiazolidinedione derivatives to block glucose uptake can also be evaluated in test mice using [$^{18}$F]-fluorodeoxyglucose uptake by positron emission tomography.

Immunohistochemistry and Western blotting can be used to characterize in vivo intratumoral biomarkers of thiazolidinedione activity in test animals as shown in Table II. These biomarkers can be classified into three categories: β-TrCP signaling (as a surrogate markers for the transient Sirt1 induction), AMPK activation, and ER stress response. Markers of tumor angiogenesis can also be examined as these can be modulated by energy restriction.

TABLE II

| Intratumoral biomarkers | |
| --- | --- |
| Proliferation index | PCNA (proliferating cell nuclear antigen), Ki67 |
| Apoptosis index | The ApopTag in situ detection kit will be used to identify apoptotic cells, which uses the terminal deoxynucleotidyltransferase (TdT)-mediated TUNEL procedure. |
| AR function | AR, PSA, and human kallikrein-2 |
| β-TrCP signaling | β-TrCP, β-catenin, cyclin D1, Sp1, and other Sp1 target proteins |
| AMPK activation | Phosphorylation of AMPK, mTOR, p70S6K, and Akt |
| ER stress | GADD153, GRP78, and IRE1α |
| Angiogenesis | Microvessel density (CD31 and Factor VIII-related antigen); VEGF |

Formulation and Administration of Thiazolidinedione Derivatives

The present invention provides a method for administering one or more thiazolidinedione derivatives in a pharmaceutical composition. Examples of pharmaceutical compositions include those for oral, intravenous, intramuscular, subcutaneous, or intraperitoneal administration, or any other route known to those skilled in the art, and generally involves providing the thiazolidinedione derivative formulated together with a pharmaceutically acceptable carrier.

When preparing the compounds described herein for oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable carrier.

For intravenous, intramuscular, subcutaneous, or intraperitoneal administration, the compound may be combined with a sterile aqueous solution which is preferably isotonic with the blood of the recipient. Such formulations may be prepared by dissolving solid active ingredient in water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

Formulations suitable for parenteral administration conveniently comprise a sterile aqueous preparation of the active compound which is preferably made isotonic. Preparations for injections may also be formulated by suspending or emulsifying the compounds in non-aqueous solvent, such as vegetable oil, synthetic aliphatic acid glycerides, esters of higher aliphatic acids or propylene glycol.

The dosage form and amount can be readily established by reference to known treatment or prophylactic regiments. The amount of therapeutically active compound that is administered and the dosage regimen for treating a disease condition with the compounds and/or compositions of this invention depends on a variety of factors, including the age, weight, sex, and medical condition of the subject, the severity of the disease, the route and frequency of administration, and the particular compound employed, the location of the unwanted proliferating cells, as well as the pharmacokinetic properties of the individual treated, and thus may vary widely. The dosage will generally be lower if the compounds are administered locally rather than systemically, and for prevention rather than for treatment. Such treatments may be administered as often as necessary and for the period of time judged necessary by the treating physician. One of skill in the art will appreciate that the dosage regime or therapeutically effective amount of the inhibitor to be administrated may need to be optimized for each individual. The pharmaceutical compositions may contain active ingredient in the range of about 0.1 to 2000 mg, preferably in the range of about 0.5 to 500 mg and most preferably between about 1 and 200 mg. A daily dose of about 0.01 to 100 mg/kg body weight, preferably between about 0.1 and about 50 mg/kg body weight, may be appropriate. The daily dose can be administered in one to four doses per day.

For example, the maximum tolerated dose (MTD) for thiazolidinedione derivatives can be determined in tumor-free athymic nude mice. Agents are prepared as suspensions in sterile water containing 0.5% methylcellulose (w/v) and 0.1% Tween 80 (v/v) and administered to mice (7 animals/group) by oral gavage at doses of 0, 25, 50, 100 and 200 mg/kg once daily for 14 days. Body weights, measured twice weekly, and direct daily observations of general health and behavior will serve as primary indicators of drug tolerance. MTD is defined as the highest dose that causes no more than 10% weight loss over the 14-day treatment period.

The thiazolidinedione derivatives can also be provided as pharmaceutically acceptable salts. The phrase "pharmaceutically acceptable salts" connotes salts commonly used to form alkali metal salts and to form addition salts of free acids or free bases. The nature of the salt is not critical, provided that it is pharmaceutically acceptable. Suitable pharmaceutically acceptable acid addition salts of compounds of formulas I, II, III, and IV may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic, and sulfonic classes of organic acids, examples of which include formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, ambonic, pamoic, methanesulfonic, ethanesulfonic, benzenesulfonic, pantothenic, 2-hydroxyethanesulfonic, toluenesulfonic, sulfanilic, cyclohexylaminosulfonic, stearic, algenic, γ-hydroxybutyric, galactaric, and galacturonic acids. Suitable pharmaceutically acceptable base addition salts of the compounds described herein include metallic salts made from aluminum, calcium, lithium, magnesium, potassium, sodium, and zinc. Alternatively, organic salts made from N,N'-dibenzylethylenediamine, chloroprocaine, choline, diethanolamine, ethylenediamine, meglumine (N-methylglucamine) and procaine may be used form base addition salts of the compounds described herein. All of these salts may be prepared by conventional means from the corresponding compounds described herein by reacting, for example, the appropriate acid or base with the compound.

Preparation of Thiazolidinedione Derivatives

Compounds of the invention may be synthesized by synthetic routes that include processes analogous to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, Reagents for Organic Synthesis, v. 1-19, Wiley, New York, (1967-1999 ed.) and similar texts known to those skilled in the art. The preparation of various thiazolidinedione derivatives is described in earlier filed patent applications by the inventors. See U.S. Pat. No. 7,566,787 and U.S. patent application Ser. No. 12/389,759, both by Chen et al., the disclosures of which are incorporated herein by reference in their entirety. The preparation of a number of specific thiazolidinedione derivatives is described in the Examples herein.

Figure 2:
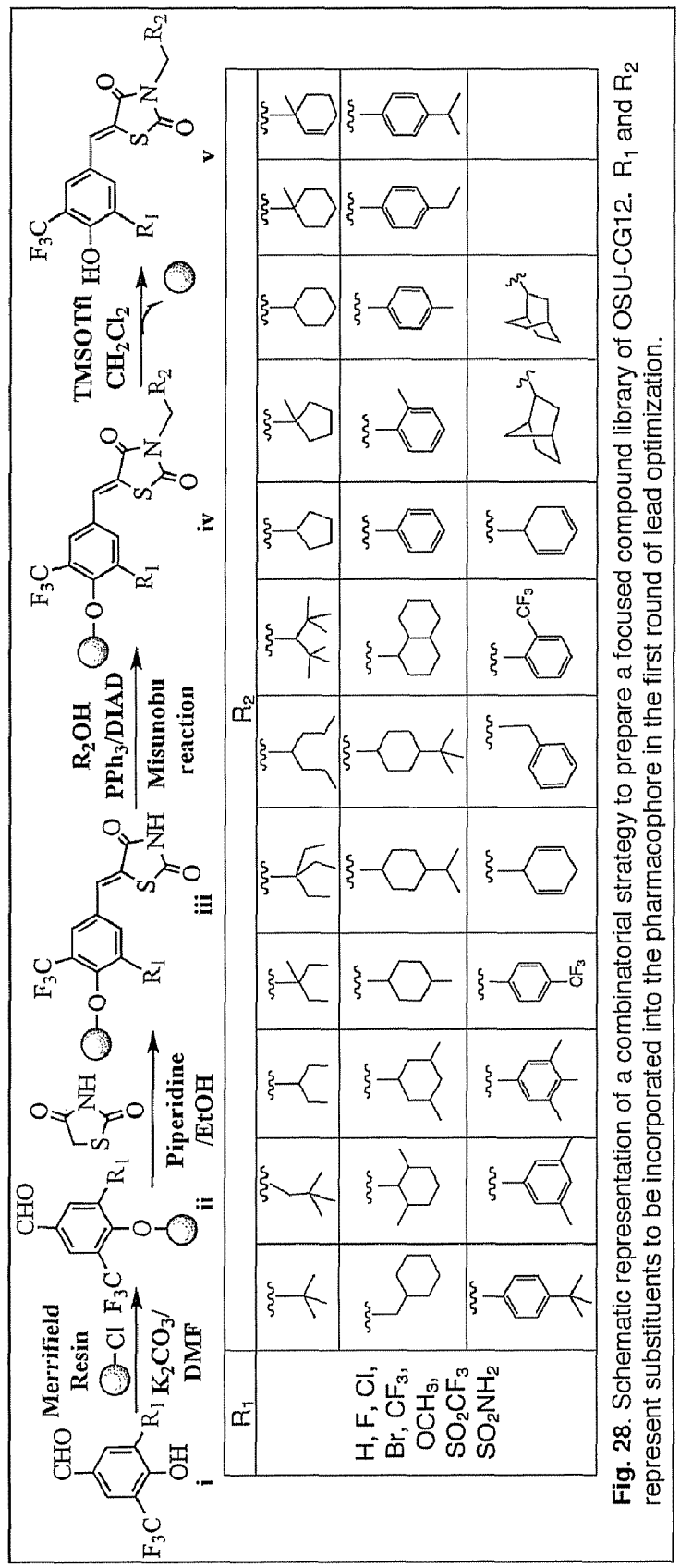
FIG. 2 provides a schematic diagram and chart showing a solid phase method for preparing a library of numerous thiazolidinedione compounds. The upper portion of the figure shows the putative synthetic scheme, while the lower portion of the figure shows the $R_1$ and $R_2$ substituents present on the compounds making up the library.

A variety of thiazolidinedione derivatives can also be prepared using solid-phase combinatorial chemistry, as shown in FIG. 2. A focused compound library can be prepared by varying the substituents on the phenolic ring ($R_1$) and the terminal hydrophobic moiety ($R_2$), as depicted in FIG. 2.

Figure 12:
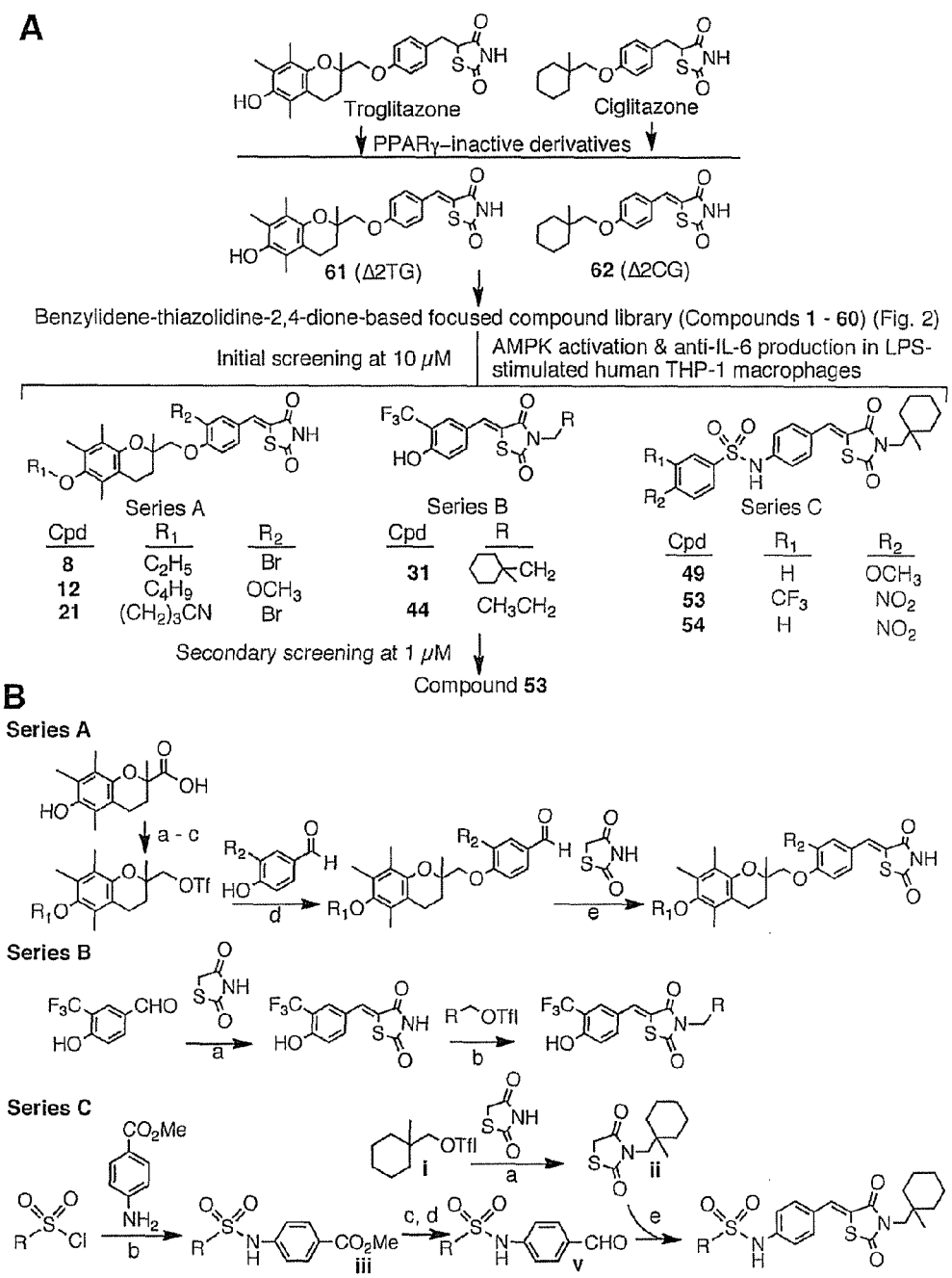
FIG. 12; section (A) provides a schematic representation of the two-tiered screening of the benzylidene-thiazolidinedione-based focused compound library to identify lead AMPK activators. Section (B) provides a general synthetic procedure for Series A-C compounds. Reaction conditions: Series A: a, $K_2CO_3$/R1-Br; b, LAH, THF; c, $(CF_3SO_2)_2O$, pyridine, $CH_2Cl_2$; d, $K_2CO_3$, DMF; e, AcOH, piperidine, ethanol/reflux. Series B: a, AcOH, piperidine, ethanol/reflux; b, $K_2CO_3$, DMF. Series C: a, $K_2CO_3$, DMF; b, pyridine, $CH_2Cl_2$; c, LAH, dry THF, 0° C.; d, $MnO_2$, $CH_2Cl_2$, reflux; d, piperidine, EtOH, reflux; e, AcOH, piperidine, ethanol/reflux.
Figure 13:
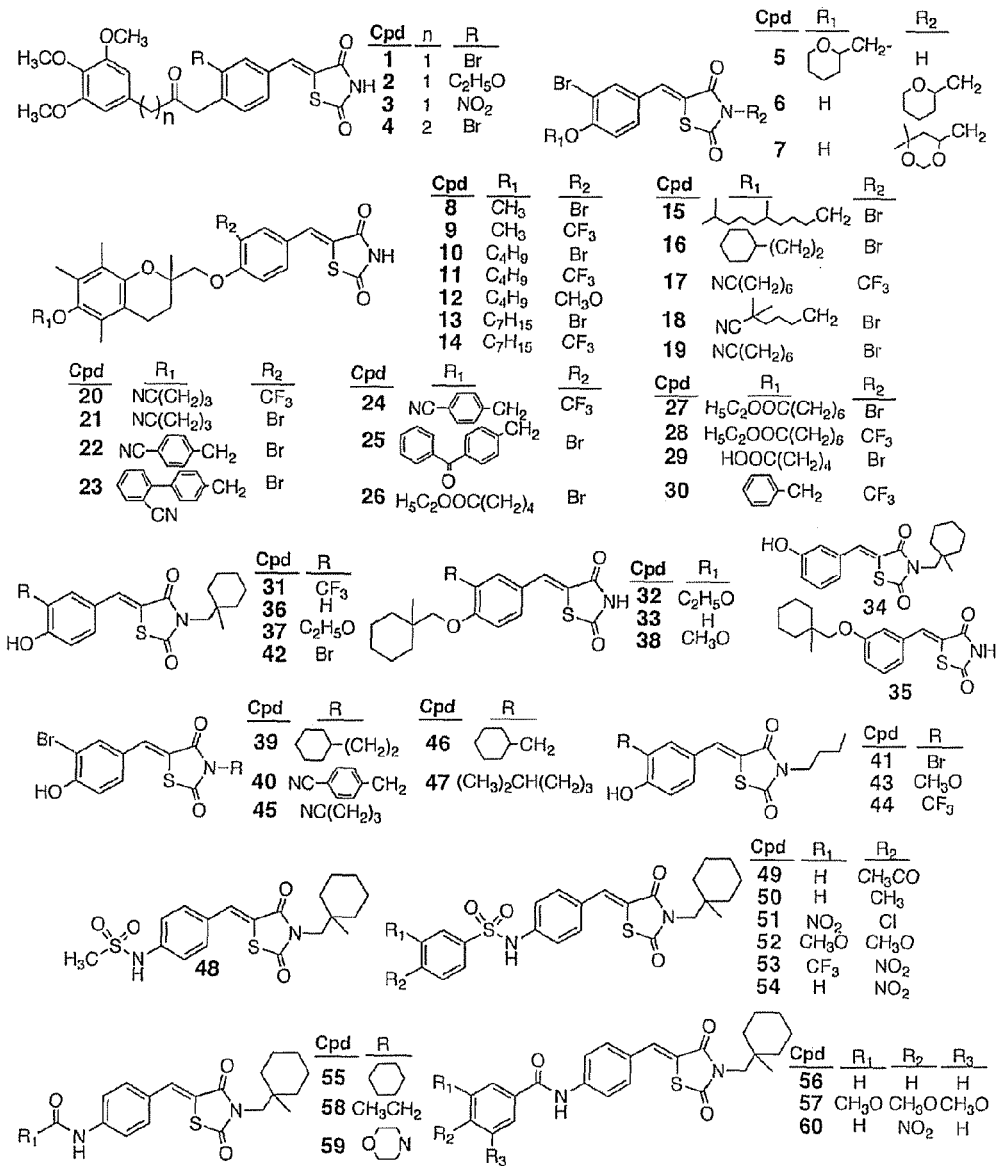
FIG. 13 provides chemical structures of compounds 1-60 in the thiazolidinedione-based focused compound library.

As illustrated in the synthetic scheme of FIG. 2, the —OH function on the substituted benzaldehyde (i) allows the tethering of the pharmacophore to the Merrifield resin via nucleophilic substitution to faun conjugate (ii), followed by the addition of the thiazolidinedione ring to yield conjugate (iii). Different hydrophobic appendages ($R_2OH$) can be introduced to the thiazolidinedione ring via the Mitsunobu Reaction (iv), which provides the final products (v) in high yield and purity upon uncoupling from the resin. As this combinatorial synthesis is conducted in a 24-well format, each cycle generates 24 derivatives in multi-mg quantities in about 10 days. Based on the substituents shown in the figure, a total of 272 derivatives (8 $R_1$×34 $R_2$) can be synthesized. The preparation of additional thiazolidinedione derivatives is shown in FIGS. 12 and 13.

The present invention is illustrated by the following examples. It is to be understood that the particular examples, materials, amounts, and procedures are to be interpreted broadly in accordance with the scope and spirit of the invention as set forth herein.

EXAMPLES

Example I

Effect of Thiazolidinedione Compounds on Energy Restriction in Cancer Cells

In this example, the inventors demonstrate that troglitazone, ciglitazone, STG28, and OSU-CG12 were able to elicit hallmark cellular responses characteristic of energy restriction in LNCaP prostate cancer and MCF-7 breast cancer cells. These energy restriction-associated changes include reduced glycolytic rate and NADH and lactate production, transient induction of silent information regulator 1 (Sirt1) gene expression, and activation of the intracellular fuel sensor AMP-activated protein kinase (AMPK) and endoplasmic reticulum (ER) stress, the interplay among which culminates in autophagy and apoptosis. The implications of this finding are multifold. First, it provides a molecular basis to use TZDs as a scaffold to develop potent energy restriction-mimetic agents, as demonstrated by the identification of OSU-CG12 as a potent energy restriction mimetic agent. OSU-CG12 exhibits potency in mediating starvation-associated cellular responses and suppressing cancer cell growth that is an-order-of-magnitude greater than resveratrol ($IC_{50}$, 5 μM versus 60-110 μM). Second, from a mechanistic perspective, this study provides the first evidence that β-transducin repeats containing protein (β-TrCP)-dependent proteasomal degradation of cell cycle- and apoptosis-regulatory proteins represents a downstream cellular event of transient Sirt1 transcriptional activation. The activation of β-TrCP signaling underlies the effect of glucose starvation and energy restriction-mimetic agents on apoptosis induction.

Methods

Cell Culture and Reagents

LNCaP hormone-responsive prostate cancer cells and MCF-7 ERα-positive breast cancer cells were obtained from the American Type Culture Collection (Manassas, Va.) and maintained with 10% fetal bovine serum (FBS)-supplemented RPMI 1640 medium and F12/DMEM medium, respectively. Nonmalignant prostate epithelial cells (PrEC) were maintained in prostate epithelial growth medium (PrEGM) (Lonza Inc., Walkersville, Md.). All cells were cultured at 37° C. in a humidified incubator containing 5% $CO_2$. Troglitazone and ciglitazone and their PPARγ-inactive derivatives STG28 and OSU-CG12 were synthesized according to published procedures. Yang et al., J Med. Chem. 51, p. 2100-2107 (2008) and Zhu et al., Cancer Res. 65, p. 7023-7030 (2005). Glucose-free RPMI 1640 medium was purchased from Invitrogen (Carlsbad, Calif.). 2-DG, resveratrol, 3-methyladenine (3-MA), nicotinamide and splitomicin were purchased from Sigma-Aldrich (St. Louis, Mo.). The AMPK inhibitor Compound C and cycloheximide were obtained from Calbiochem (San Diego, Calif.). These agents were added to medium with a final DMSO concentration of 0.1%. Antibodies against various proteins were obtained from the following sources. Mouse monoclonal antibodies: β-catenin, cyclin D1, Wee1, p53 and GFP, Santa Cruz Biotechnology (Santa Cruz, Calif.); β-TrCP, Invitrogen; β-actin, MP Biomedicals (Irvine, Calif.). Rabbit antibodies: Myc, PARP, NFκB/p105, AR, ERα, p-Ser9-GSK3β, GSK3β, p-Ser473-Akt, Akt, p-Thr202/Tyr204-ERK, ERK, p-Thr180/Tyr182-p38, p38, p-Ser176/180-IκB kinase α (IKKα), IKKα, p-Thr172-AMPK, AMPK, GRP78, Sirt1, AcK382-p53, IRE1α, pSer2448-mTOR, mTOR, p-Thr389-p70S6K, p70S6K and TSC2, Cell Signaling Technology (Beverly, Mass.); EGFR, Sp1 and GADD153, Santa Cruz. Human DDIT3 SMARTpool siRNA was obtained from Dharmacon (Lafayette, Colo.). The Flag-tagged Sirt1 (wild-type [WT] and H363Y dominant negative), HA-tagged Sirt1, Myc-tagged AMPK (WT and K45R kinase-dead) and TSC2 shRNA plasmids were purchased from Addgene (Cambridge, Mass.). WT- and αF-β-TrCP-Myc plasmids were prepared as described (Wei et al., Mol Pharmacol. 76 p. 47-57 (2009)). The GFP-LC3 plasmid was kindly provided by a colleague (Kabeya et al. LC3, EMBO J. 19 p. 5720-5728 (2000)).

RNA Isolation and Semiquantitative PCR Analysis

Total RNA was isolated from drug-treated LNCaP cells using the RNeasy mini kit (Qiagen, Valencia, Calif.), and then reverse-transcribed to cDNA using the Omniscript RT Kit (Qiagen) according to manufacturer's instructions. PCR products were separated electrophoretically in 1% agarose gels and visualized by ethidium bromide staining.

Transient Transfection, Immunoblotting and Fluorescent Microscopic Analysis

Transfections were performed by electroporation using Nucleofector kit R of the Amaxa Nucleofector system (Amaxa Biosystems, Cologne, Germany). LNCaP cells were transfected with the following plasmids or siRNA: WT- and H363Y-Flag-Sirt1 (DN-Sirt1), WT- and K45R-Myc-AMPK (DN-AMPK), GFP-LC3, TSC2 shRNA, and DDIT3 siRNA (GADD153). Immunoblotting for various target proteins was performed on cell lysates harvested with M-PER lysis buffer (Pierce, Rockford, Ill.) as previously described (Wei et al., Mol. Pharmacol. 76 p. 47-57 (2009)). For the fluorescent microscopic analysis, LNCaP cells transfected with the GFP-LC3 expression plasmid or with scrambled or TSC2 shRNA were treated as indicated for 36 h. After cells were fixed with 3.7% formaldehyde at room temperature for 20 min, nuclear counterstaining was performed using a 4,6-diamidino-2-phenylindole (DAPI)-containing mounting medium (Vector Laboratories, Burlingame, Calif.) before examination. Images were observed using a Nikon microscope (Eclipse TE300).

Determination of Glycolytic Rate

Glycolytic rate was determined by measuring the conversion of [5-$^3$H]glucose (GE Healthcare, Piscataway, N.J.) to $^3$H$_2$O according to a published procedure (Ashcroft et al., Biochem J. 126, p. 525-532 (1972)). Briefly, LNCaP cells were seeded in six-well plates ($4\times10^5$ cells/well) and then treated 24 h later with 10 mM 2-DG or 10 µM OSU-CG12 for various intervals. After washing with PBS, cells were trypsinized and resuspended in 500 µL of Krebs buffer [25 mM NaHCO$_3$, 115 mM NaCl, 2 mM KCl, 2 mM CaCl$_2$, 1 mM MgCl$_2$ and 0.25% BSA (pH, 7.4)] containing 1 mM nonradioactive glucose and 5 µCi/mL [5-$^3$H]glucose for 1 h at 37° C. Aliquots from each treatment group were added to 0.2 N HCl in open tubes that were placed upright in scintillation vials containing 1 mL of H$_2$O. The vials were sealed and H$_2$O produced by glucose consumption was equilibrated with H$_2$O outside the tube for a minimum of 24 h at room temperature. The amount of $^3$H retained in the tube and the amount that had diffused into the surrounding H$_2$O by evaporation and condensation were determined separately by using a scintillation counter LS6500 (Beckman). [5-$^3$H]glucose-only and $^3$H$_2$O-only standards were included in each experiment for calculation of the rate of conversion of [5-$^3$H]glucose to H$_2$O using the following equation: glucose utilized (pmol)=[$^3$H] water formed (d.p.m)/[5-$^3$H]glucose (d.p.m/pmol)].

Glucose Uptake Assay

LNCaP cells in six-well plates ($4\times10^5$ cells/well) were exposed to different concentrations of resveratrol or OSU-CG12 and then incubated with Krebs-Ringer phosphate buffer (128 mM NaCl, 4.7 mM KCl, 2.5 mM MgSO$_4$, 5 mM Na$_2$HPO$_4$ and 1% BSA) for 30 min at 37° C. After washing cells with PBS, glucose uptake was initiated by addition of 1 mL of PBS containing 1 µCi/mL [$^3$H]-2-DG (Perkin Elmer, Waltham, Mass.) and 100 mM nonradioactive 2-DG. After 5 min, glucose uptake was terminated by extensive washing with PBS, and cells were solubilized in 0.1% SDS buffer. Aliquots were taken for measurements of radioactivity using a scintillation counter LS6500 (Beckman).

NADH Assay and Lactate Assay

Determinations of intracellular levels of NADH and lactate were performed using the EnzyChrom NAD$^+$/NADH Assay Kit and EnzyChrom L-Lactate Assay Kit, respectively (BioAssay Systems, Hayward, Calif.). Briefly, LNCaP cells were cultured in 24-well plates at the density of $2\times10^5$ cells/well for 24 h followed by treatments of 10 mM 2-DG or 10 µM OSU-CG12 for various time intervals. After cells were trypsinized and collected, intracellular levels of NADH and lactate were determined according to manufacturer's instructions.

Cell Viability Assay

Cell viability was determined using the 3-(4,5-dimethylthiazol-2-yl)-2,5-diphenyltetrazolium bromide) (MTT) assay. LNCaP and MCF-7 cells were seeded in 96-well plates (5000 cells/well) and incubated in their respective culture media supplemented with 10% FBS for 24 h. Cells were then treated with various concentrations of OSU-CG12, STG28, CG, TG, resveratrol, and 2-DG for 72 h. Drug-containing medium was then replaced with 1×MTT (0.5 mg/mL in RPMI 1640), followed by incubation at 37° C. for 2 h. After removal of medium, the reduced MTT dye was solubilized in 200 µL/well DMSO, and absorbances were measured at 570 nm. For the assessment of the effect of supplemental glucose, cells were treated with OSU-CG12 in the presence of 0.5, 2, 10 or 20 mg/mL glucose for 72 h prior to addition of MTT. In the β-TrCP overexpression experiments, cells transfected with WT- or ΔF-β-TrCP-Myc plasmids were exposed to various concentrations of OSU-CG12 for 72 h prior to addition of MTT.

Flow Cytometric Analysis

LNCaP cells transfected with WT-, or ΔF-β-TrCP were seeded in six-well plates ($4\times10^5$ cells/well), cultured for 24 h, and then treated with DMSO, 5 mM 2-DG or 5 µM OSU-CG12 for 48 h. After extensive washing with PBS, cells were fixed overnight in ice-cold 80% ethanol at 4° C., and then stained with propidium iodide (50 µg/mL in PBS containing 100 units/mL RNAase A). Cell cycle phase distributions were determined using a FACScort flow cytometer and analyzed by the ModFitLT V3.0 program.

Statistical Analysis

Each experiment was performed in triplicate. All experiments were performed at least two times on different occasions. Where appropriate, the data are presented as the mean±95% confidence interval.

Results

Figure 3:
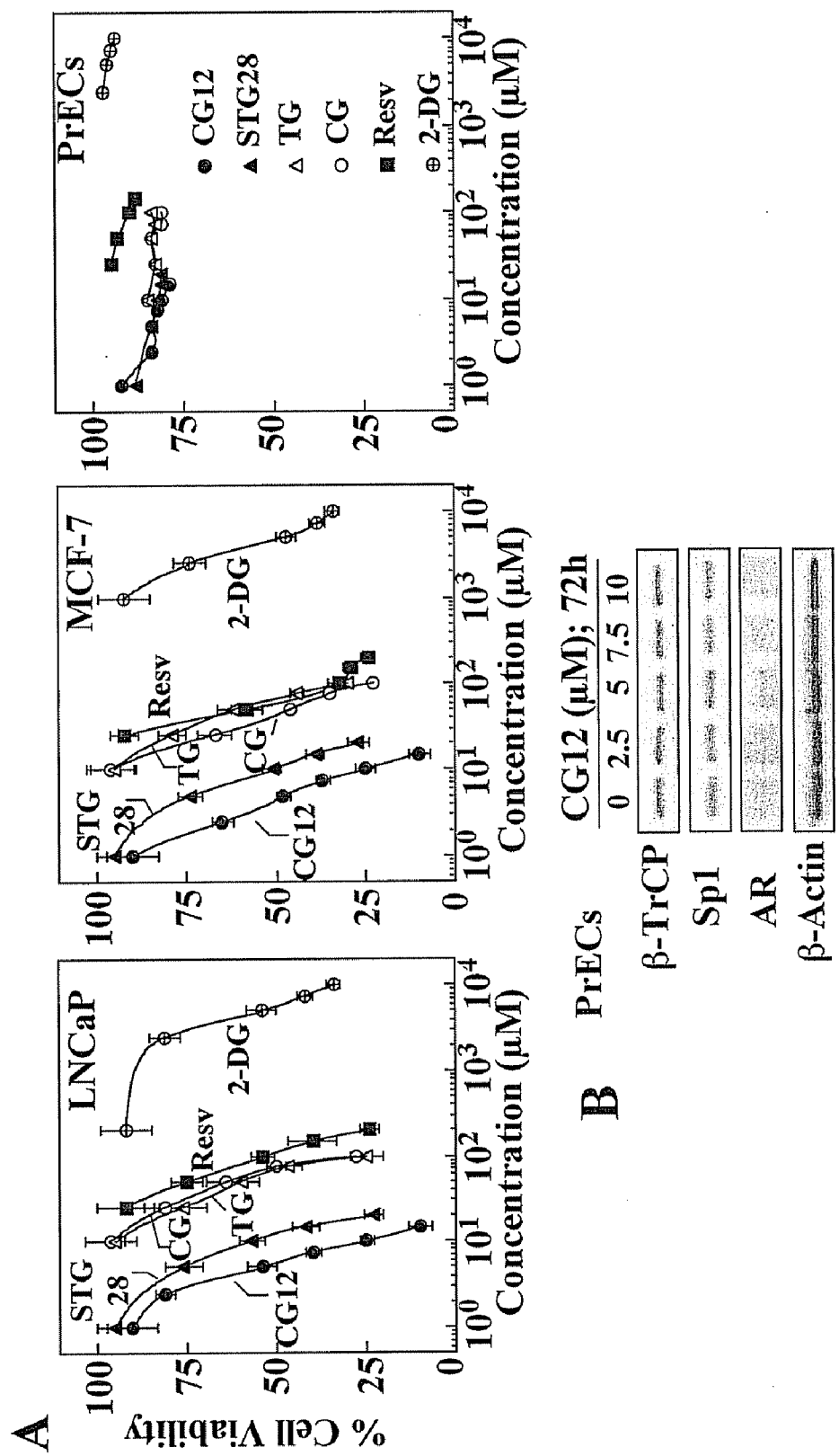
FIG. 3 provides graphs and an immunoblot showing the PPARγ-independent antiproliferative effects of TZDs. Section A) Shows the dose-dependent effects of troglitazone (TG), ciglitazone (CG), STG28 (STG), and OSU-CG12 (CG12) vis-à-vis the two energy restriction-mimetic agents, resveratrol (Resv) and 2-deoxyglucose (2-DG), on the viability of LNCaP prostate and MCF-7 breast cancer cells versus nonmalignant prostate epithelial cells (PrECs) in 10% FBS-supplemental medium for 72 h. MTT data are expressed as means±95% confidence intervals (error bars) (n=6). Section B) Shows the lack of effect of OSU-CG12 on the expression levels of β-TrCP, Sp1, and androgen receptor (AR) in PrECs, demonstrating the resistance of nonmalignant PrECs to OSU-CG12's antiproliferative activity. The Western blots are representative of three independent experiments, all with similar results.

TZDs exhibit the ability to induce autophagy in cancer cells. The inventors have shown that TZDs and glucose deprivation share the ability to induce β-TrCP-mediated proteasomal degradation, thereby demonstrating that TZDs can be used as energy restriction-mimetic agents. In the literature, many small-molecule agents have been reported to suppress cancer cell proliferation by selectively targeting tumor energy metabolism, among which 2-DG and resveratrol are especially noteworthy. However, these agents, in general, exhibit low antiproliferative potency, which becomes a limiting factor for their therapeutic applications. For example, the IC$_{50}$ values for 2-DG in inhibiting the viability of LNCaP prostate cancer and MCF-7 breast cancer cells were 5.5 mM and 4.2 mM, respectively, while those of resveratrol were 110 µM and 60 µM, respectively (FIG. 3A). In contrast, while the antiproliferative potencies of troglitazone (70 µM and 70 µM) and ciglitazone (70 µM and 42 µM) were comparable to that of resveratrol, their PPARγ-inactive, optimal derivatives, STG28 (12 µM and 11 µM) and OSU-CG12 (5.7 µM and 5.0 µM), showed one- and three-orders-of-magnitude higher potencies than resveratrol and 2-DG, respectively. Equally important, these TZDs as well as 2-DG and resveratrol displayed low cytotoxicity to normal prostate epithelial cells (PrECs). This differential antiproliferative effect between malignant and nonmalignant cells might be attributable to the inability of TZDs to induce β-TrCP-mediated proteasomal degradation in PrECs, as evidenced by the unaltered expression levels of β-TrCP, Sp1, and AR after treatment with escalating concentrations of OSU-CG12 for 48 h (FIG. 3B).

Figure 4:
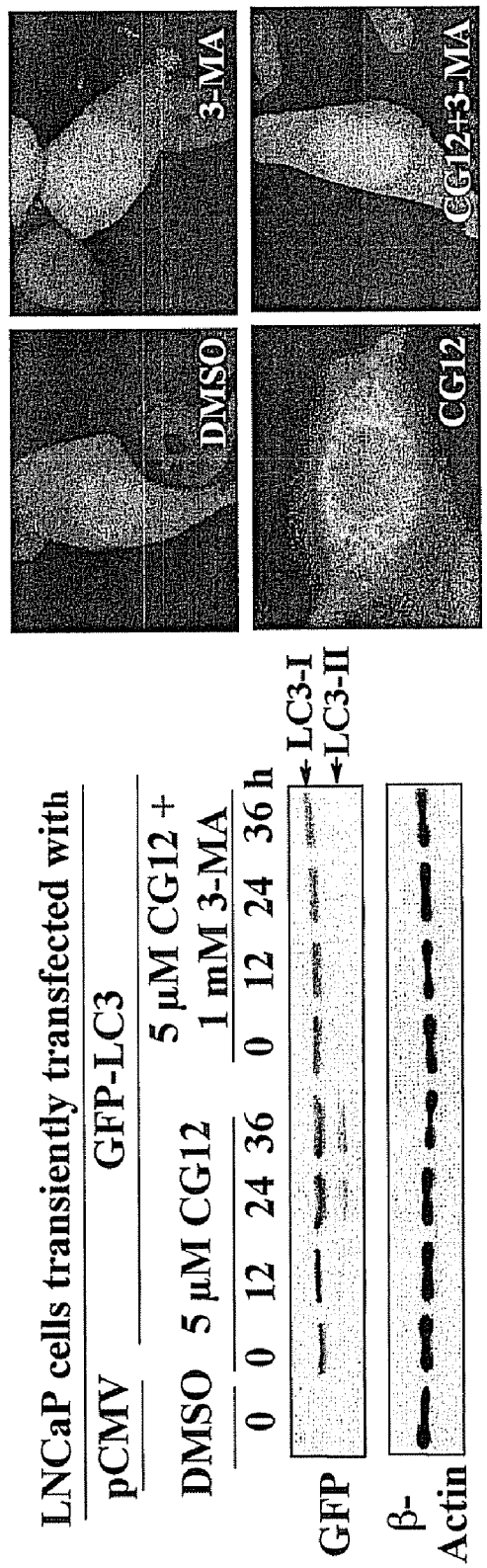
FIG. 4 provides evidence that TZDs induce autophagy. The left panel provides an immunoblot showing the time-dependent effect of 5 μM OSU-CG12 on the conversion of LC3-I to LC3-II, a marker for autophagy, which, however, could be blocked by the autophagy inhibitor 3-MA (1 mM). LNCaP cells were transiently transfected with GFP-LC3 plasmids, followed by exposure to 5 μM OSU-CG12 alone or in the presence of 3-MA for the indicated time intervals. Immunoblotting of GFP was performed to detect LC3-II formation. The right panel provides images from microscopic analysis of the effect of 5 μM OSU-CG12, alone or in the presence of 1 mM 3-methyladenine (3-MA), on the pattern of GFP-LC3 fluorescence. The punctate pattern evident in the CG12 group indicates its accumulation into autophagic vacuoles. GFP-LC3-expressing LNCaP cells cultured in six-well plates were subjected to different drug treatments for 36 h and then examined by fluorescence microscopy. The immunoblotting and microscopic data are representative of three experiments, all with similar results.
Figure 5:
FIG. 5 provides immunoblots showing that energy restriction and TZDs share the ability to facilitate β-TrCP-mediated proteolysis. LNCaP and MCF-7 cells were exposed as indicated to troglitazone (TG), STG28, ciglitazone (CG), OSU-CG12 (CG12), the two energy restriction-mimetic agents, 2-deoxyglucose (2-DG) and resveratrol, and glucose-free medium (glucose starvation), and the effects on components of β-TrCP-mediated proteolysis were assessed by western blotting. These endpoints included expression of β-TrCP, β-TrCP substrates, and Sp1 target gene products, and the phosphorylation status of kinases involved in facilitating β-TrCP-substrate recognition. Immunoblots are representative of three independent experiments.

Autophagy represents a characteristic cellular response to energy restriction in cancer cells, as well as healthy cells (Singletary et al., Cancer Epidemiol Biomarkers Prey. 17, p. 1596-1610 (2008)). 2-DG (DiPaola et al. Prostate. 68 p. 1743-1752 (2008)) and resveratrol (Kueck et al., Gynecol Oncol. 107 p. 450-457 (2007)) has been reported to induce autophagy in cancer cells at the dose ranges of 5-25 mM and 50-100 µM, respectively, in line with the respective concentrations needed to cause antiproliferative effect. The inventors therefore examined the ability of TZDs to mediate the conversion of microtubule-associated protein 1 light chain 3 (LC3)-II from LC3-I, an essential step for autophagosome formation. LNCaP cells were transiently transfected with a GFP-LC3 expression vector, and subjected to treatment with 5 µM OSU-CG12 with or without 1 mM 3-methyladenine (3-MA), a known inhibitor of autophagy. Western blotting with anti-GFP antibodies reveals a time-dependent accumulation of LC3-II in drug-treated cells, which, however, could be blocked by 3-MA (FIG. 4, left panel). Moreover, fluorescence microscopy shows that OSU-CG12 induced a punctate fluorescent pattern of fluorescence, indicative of GFP-LC3 accumulation into autophagic vacuoles (right panel). Again, this punctate pattern of GFP-LC3 fluorescence was prevented by 3-MA co-treatment. Similar results were also obtained with other TZDs as well as in MCF-7 cells (data not shown). These data provide further support for the contention that TZDs elicit responses in cancer cells that parallel those induced by energy restriction.

β-TrCP-mediated proteasomal degradation represents an energy restriction-elicited signaling event. Based on the inventors' previous finding that β-TrCP-dependent proteolysis of cyclin D1 and Sp1 occurs, not only after treatment with TZDs, but also in response to glucose deprivation, they hypothesized that this β-TrCP-mediated proteasomal degradation was consequent to the ability of TZDs to perturb energy metabolism. To address this hypothesis, they sought to establish β-TrCP-mediated proteolysis as an energy restriction-elicited signaling event. Consequently, the effects of glucose starvation were assessed using two known energy restriction-mimetic agents, 2-DG and resveratrol, and four different TZDs (troglitazone, ciglitazone, and their respective PPARγ-inactive analogues, STG28 and OSU-CG12) on the expression levels of a series of signaling proteins pertinent to β-TrCP-dependent proteolysis in LNCaP and MCF-7 cells. These proteins included β-TrCP, the β-TrCP substrates Sp1, β-catenin, cyclin D1, Wee1, NF-κB/p105, and the Sp1 target gene products AR, ERα, and EGFR. As shown in FIG. 5, the ability of TZDs to upregulate β-TrCP expression and to suppress the expression of the β-TrCP substrates and Sp1 target proteins was shared by glucose starvation and the two energy restriction-mimetic agents. It is noteworthy that the relative potencies with which these effects were induced paralleled those observed for growth inhibition by these agents.

Moreover, as phosphorylation of serine residues within the DSG motif of target proteins is a prerequisite for recognition by β-TrCP, the effects of TZDs vis-à-vis glucose starvation, 2-DG, and resveratrol on the activation status of a series of kinases potentially involved in the phosphorylation of β-TrCP substrates, including GSK3β (β-catenin and Sp1), ERKs (Sp1), IKKα (cyclin D1), Akt, and p38, were compared. Consistent with the shared ability of TZDs and energy restriction to promote β-TrCP-facilitated protein degradation, exposure of LNCaP cells to any of these agents or to glucose-free medium led to similar changes in the phosphorylation levels of these kinases (FIG. 5). Specifically, decreases in the phosphorylation of Akt were accompanied by increases in that of GSK3β, ERKs, p38, and IKKα. Similar effects on the expression/phosphorylation of these signaling biomarkers were also noted in MCF-7 cells treated with 5 µM OSU-CG12, 5 mM 2-DG or glucose starvation. Together, these correlative data suggest that β-TrCP-mediated protein degradation represents a downstream signaling event of energy restriction.

TZDs mimic energy restriction by induction of Sirt1 expression, AMPK activation, and ER stress response. To further evaluate the hypothesis that TZDs induce β-TrCP-mediated proteasomal degradation in cancer cells by disrupting energy metabolism, the ability of TZDs to elicit three well documented hallmarks cellular responses to energy restriction: Sirt1 gene expression (Cohen et al., Science 305 p. 390-392 (2004), AMPK activation (Jiang et al., Cancer Res. 68 p. 5492-5499 (2008)), and ER stress (Lin et al., Proc Natl Acad Sci USA. 81, p. 988-992 (1984)), were examined. Time course of changes in biomarkers representative of each of these energy restriction responses, i.e., induction of Sift1 expression and the consequent deacetylation of p53, phosphorylation of AMPK, and expression of glucose-regulated protein (GRP)78, an ER stress-response protein, were assessed in LNCaP cells treated with 10 µM OSU-CG12, in comparison with 10 mM 2-DG and glucose starvation, by Western blotting and/or RT-PCR.

Figure 6:
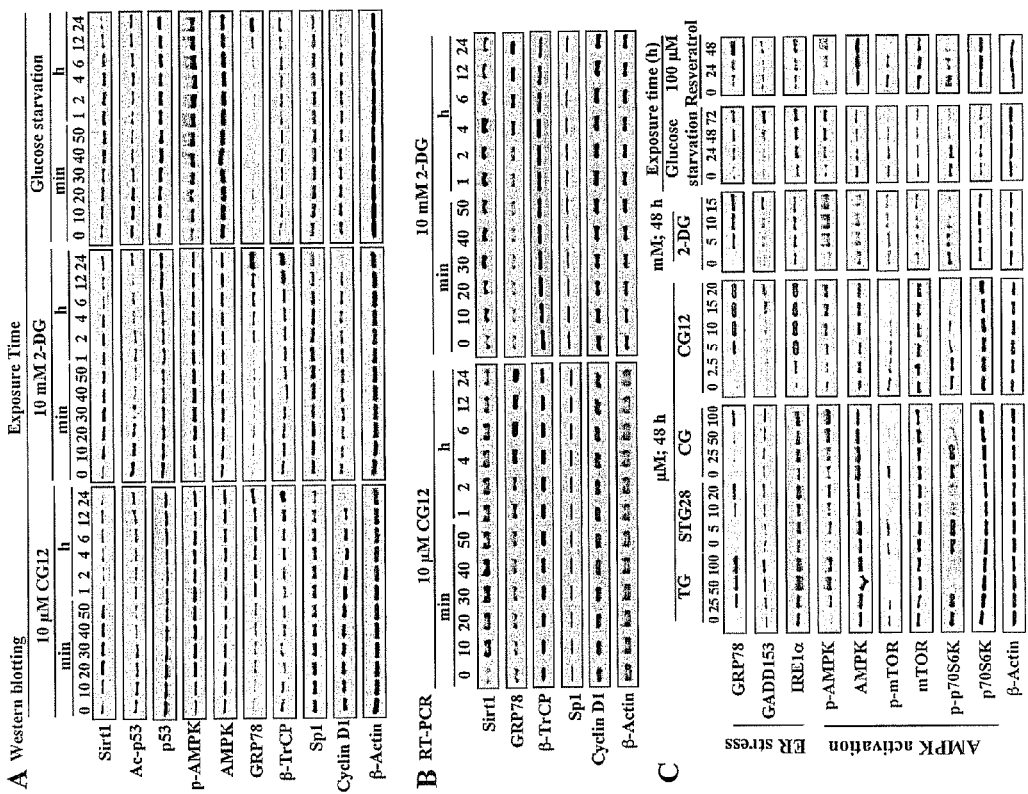
FIG. 6 provides immunoblots showing that TZDs share the ability of 2-deoxyglucose (2-DG) and glucose starvation to elicit energy restriction-associated cellular responses in LNCaP cells. Section A) shows a Western blot analysis of the time-dependent effects of 10 μM OSU-CG12 (CG12) vis-à-vis 10 mM 2-DG and glucose starvation on various markers associated with energy restriction (induction of Sirt1 expression, p53 deacetylation, AMP-activated protein kinase (AMPK) phosphorylation, and the expression of endoplasmic reticulum (ER) stress indicator GRP78 and with β-TrCP-dependent proteolysis (expression levels of β-TrCP, Sp1, and cyclin D1). Section B) shows the parallel analysis of the mRNA expression levels of Sirt1, GRP78, β-TrCP, Sp1, and cyclin D1 by RT-PCR in LNCaP cells treated with CG12 and 2-DG as in A. Section C) shows a Western blot analysis of the effect of TZDs at different doses, relative to 2-DG, resveratrol, and glucose starvation, on ER stress and AMPK/mTOR/p70S6K signaling in LNCaP cells. Indicators of ER stress included the expression levels of IRE1α, an ER stress sensor, GRP78 and GADD153. Immunoblots and PCR results are representative of three independent experiments.

As shown in FIG. 6A, OSU-CG12 exhibited a high degree of similarity relative to 2-DG and glucose starvation in mediating these cellular responses. For example, exposure of LNCaP cells to OSU-CG12, 2-DG, or glucose starvation for 10 min led to immediate, robust increases in Sirt1 expression and AMPK phosphorylation, followed by rises in the expression level of GRP78 at about 1 h post-treatment. In contrast, increases in the expression level of β-TrCP and the consequent degradation of Sp1 and cyclin D1 lagged behind these signature cellular responses by more than 10 h, suggesting that β-TrCP upregulation represents a downstream event of at least one of these energy restriction-induce pathways. Two important features were noteworthy regarding these findings. First, the transcriptional activation of Sirt1 gene expression was transient with a short duration ranging from 1 h for OSU-CG12 to 4 h for 2-DG and glucose deprivation, which was paralleled by changes in the acetylation level of p53, a Sirt1 deacetylase substrate. Second, RT-PCR analysis indicates that increases in the expression levels of Sirt1 and GRP78 in both TZD- and 2-DG-treated cells were mediated through changes in mRNA level, while that of β-TrCP was attributable to regulation at the protein level, as drug-treatments had no effect on abundance of β-TrCP mRNA (FIG. 6B).

Additional evidence for the targeting of energy restriction by TZDs is evident in the parallel effects of TZDs and energy restriction on ER stress and AMPK signaling. Treatment of LNCaP cells with troglitazone, STG28, ciglitazone, and OSU-CG12 induced ER stress as manifested by the dose-dependent upregulation of the expression levels of two ER stress-response proteins, GRP78 and growth-arrest and damage-inducible gene (GADD)153, and the ER-associated transducer inositol requiring 1α (IRE1α), which has been shown to upregulate GRP78 and GADD153 expression (FIG. 6C). Moreover, the ability of TZDs to activate AMPK signaling was corroborated by the concomitant dephosphorylation of mammalian target of rapamycin (mTOR) and p70S6K, both of which are major effectors of cell growth and proliferation via the regulation of protein synthesis (Hay et al., Genes Dev. 18, p. 1926-1945 (2004) and Martin et al., Curr Opin Cell Biol. 17 p. 158-166 (2005)). This modulation of markers of ER stress and activation of AMPK signaling were paralleled by those observed in cells treated with 2-DG, resveratrol and glucose starvation.

Figure 7:
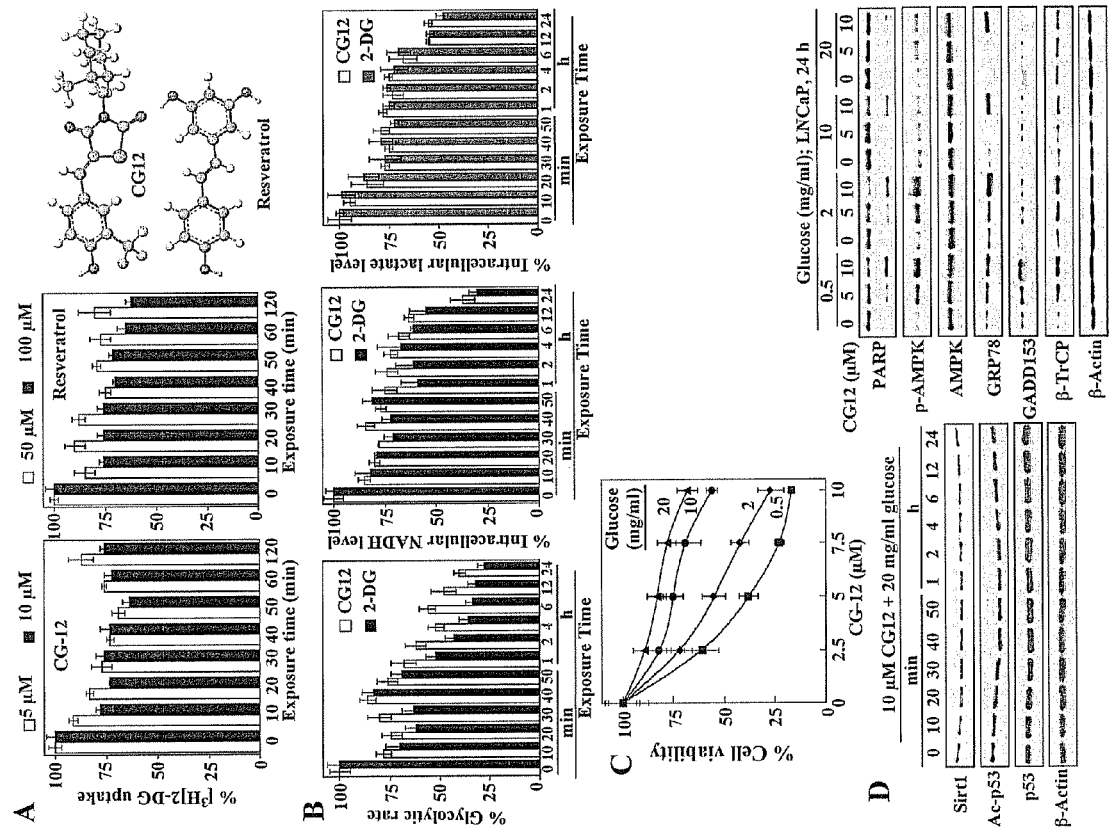
FIG. 7 provides graphs and immunoblots showing that TZDs target energy metabolism by blocking glucose uptake. Section A) shows the dose- and time-dependent effects of OSU-CG12 (CG12, left panel) and resveratrol (central panel) on [$^3$H]-2-deoxyglucose ([$^3$H]-2DG) uptake. Data are expressed as the means±95% confidence intervals (error bars) (n=3). Right panel, ball-and-stick structures of OSU-CG12 and resveratrol. Section B) shows the time-dependent effect of 10 μM OSU-CG12 vis-à-vis 10 mM 2-DG on glycolytic rate (left panel) and intracellular levels of NADH (central panel) and lactate (right panel) in LNCaP cells. Data are expressed as the means±95% confidence intervals (error bars) (n=3). Section C) demonstrates that supplemental glucose provides dose-dependent protection against OSU-CG12's antiproliferative activity in LNCaP cells. The viability of cells cultured in the presence of the indicated concentrations of glucose was determined by MTT assay after 72 h of drug treatment. Data are expressed as means±95% confidence intervals (error bars) (n=6). In section D) the left panel demonstrates that supplemental glucose (20 mg/ml) reversed the transient induction of Sirt1 and consequent deacetylation of p53 by OSU-CG12 in LNCaP cells over a 24-h time period. The right panel of D) demonstrates that supplemental glucose suppresses PARP cleavage, AMPK activation, and induction of the expression of GRP78, GADD153, and β-TrCP in LNCaP cells treated with different doses of OSU-CG12. The immunoblot results are representative of three independent experiments.

OSU-CG12 targets energy metabolism by blocking glucose uptake. The findings described above show that TZDs induce cellular signaling pathways characteristic of the cellular response to energy restriction. Pursuant to these findings, several lines of evidence were obtained showing that TZDs mimic energy restriction by blocking cellular uptake of glucose. First, the effect of OSU-CG12 versus resveratrol, a known inhibitor of glucose uptake (Kueck et al., Gynecol Oncol., 107 p. 450-457 (2007)), on the transport of [$^3$H]-2-DG into LNCaP cells was assessed. As shown, OSU-CG12 at 5 and 10 μM and resveratrol at 50 and 100 μM were able to significantly inhibit glucose uptake in a dose-dependent manner ($P<0.05$ for all time points) (FIG. 7A). From a structural perspective, OSU-CG12 and resveratrol exhibited some degree of similarity, especially with respect to the spatial arrangement of the hydrophilic functionalities, which might underlie the shared mode of action in inhibiting glucose uptake. Second, OSU-CG12 (10 μM) mediated time-dependent suppression of the glycolytic rate, NADH production and lactate formation in LNCaP cells in a manner similar to that of 2-DG (10 mM) (FIG. 7B). Treatment with either agent for 24 h reduced glucose consumption and intracellular NADH and lactate levels by 50% to 70%. Third, high levels of supplemental glucose could protect cells from OSU-CG12's antiproliferative effects. To examine the effect of glucose on the susceptibility of LNCaP cells to OSU-CG12, different amounts of glucose were added to glucose-deficient medium to achieve final concentrations ranging from 0.5 mg/ml to 20 mg/ml. Relative to 2 mg/ml, the glucose content in unmodified 10% FBS-containing RPMI 1640 medium, 10 and 20 mg/ml glucose provided significant protection against OSU-CG12-induced cell death ($P<0.05$ for all time points), while 0.5 mg/ml rendered LNCaP cells more susceptible to the drug's effect (FIG. 7C). This protective effect was further confirmed by the ability of supplemental glucose at 10 and/or 20 mg/ml to suppress OSU-CG12-induced PARP cleavage and energy restriction-associated cellular responses, including increases in the expression levels of Sirt1, β-TrCP, GRP78, and GADD153, and activation of AMPK (FIG. 7D).

Figure 8:
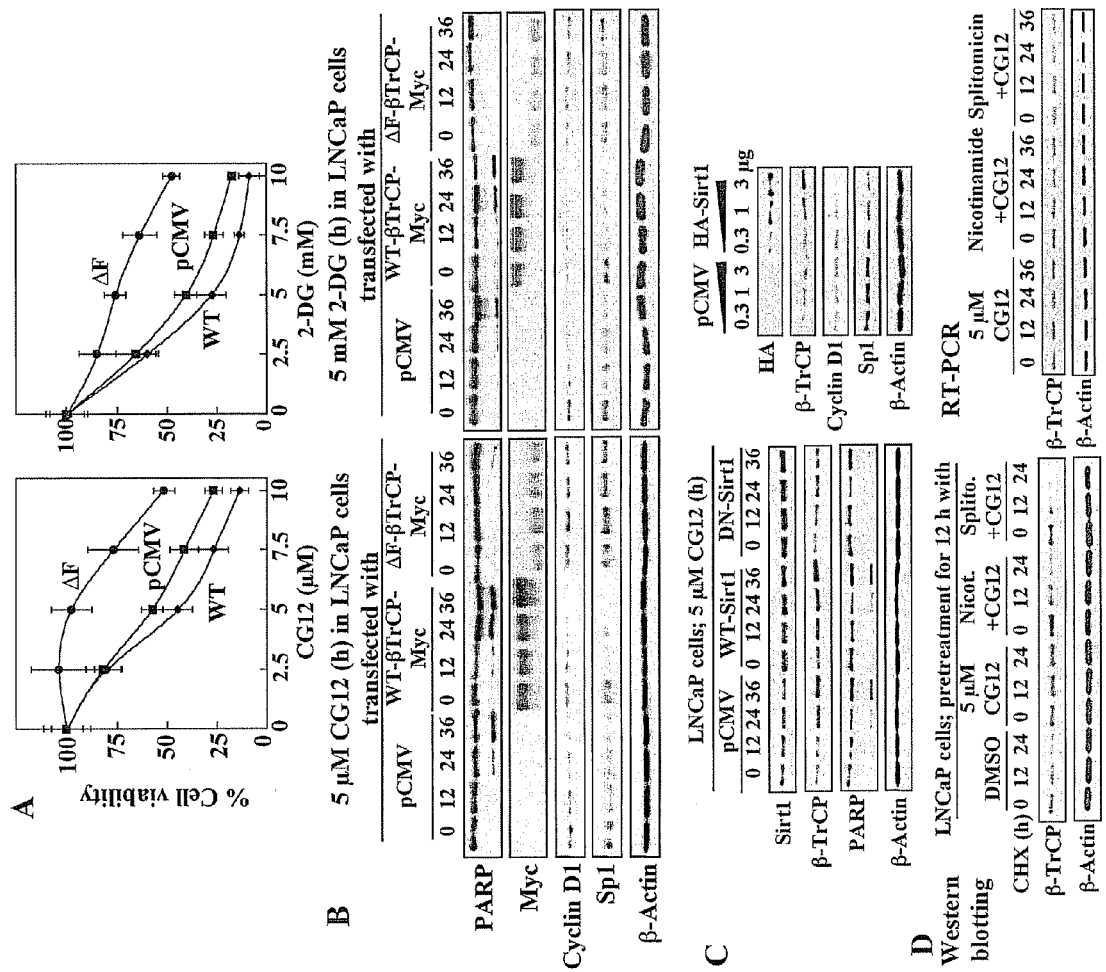
FIG. 8 provides graphs and immunoblots showing that β-TrCP expression is important for the antiproliferative effects of energy restriction mimetic agents and is upregulated by Sirt1-mediated stabilization of β-TrCP protein. Section A) shows the effects of ectopic expression of the wild type (WT) or dominant-negative (ΔF) form of β-TrCP on the dose-dependent inhibition of LNCaP cell viability by OSU-CG12 (CG12, left panel) and 2-deoxyglucose (2-DG, left panel). Cell viability was determined by MTT assays. Data are expressed as means±95% confidence intervals (error bars) (n=6). pCMV, cells transfected with the empty vector. Section B) shows the effects of ectopic expression of WT (WT-β-TrCP-Myc) and dominant-negative (ΔF-β-TrCP-Myc) β-TrCP on the ability of OSU-CG12 (5 μM) and 2-DG (5 mM) to facilitate PARP cleavage in LNCaP cells. Section C) shows that Sirt1 upregulation elevates β-TrCP expression levels in OSU-CG12-treated LNCaP cells. Left panel, ectopic expression of hemagglutinin-tagged Sirt1 (HA-Sirt1) increased β-TrCP expression in a dose-dependent manner with corresponding decreases in the expression of target proteins cyclin D1 and Sp1. Right panel, dominant-negative inhibition of Sirt1 blocked OSU-CG12-mediated β-TrCP induction and PARP cleavage. Section D) provides evidence that Sirt1 increased β-TrCP expression via protein stabilization. Left panel, Sirt1 deacetylase activity is essential for the stabilization of β-TrCP protein by OSU-CG12. Pharmacological inhibition of Sirt1 deacetylase activity by nicotinamide or splitomicin reversed the ability of OSU-CG12 to enhance β-TrCP protein stability. LNCaP cells were pretreated with 5 μM OSU-CG12 alone or in the presence of 50 mM nicotinamide or 200 μM splitomicin, for 12 h, followed by treatment with 100 μg/mL cycloheximide for an additional 12 or 24 h. Right panel, RT-PCR analysis showed that β-TrCP mRNA levels in LNCaP cells treated as described above remained unchanged. All immunoblots and PCR results are representative of three independent experiments.

Dominant-negative inhibition of β-TrCP protected cells from OSU-CG12 and 2-DG-induced apoptosis. The above findings suggest that upregulation of β-TrCP expression and consequent proteolysis of substrates represent a major cellular response to energy restriction. As β-TrCP facilitates the degradation of a series of cell cycle- and apoptosis-regulatory proteins, the inventors hypothesized that β-TrCP might play a crucial role in mediating the antiproliferative effects of energy restriction-mimetic agents. To corroborate this premise, the effect of ectopic expression of wild-type (WT) β-TrCP versus F-box-deleted β-TrCP (ΔF-β-TrCP), which acts as a dominant-negative mutant due to lack of the F-box motif, on OSU-CG12 and 2-DG-induced growth inhibition was examined. Relative to the pCMV control, enforced expression of β-TrCP enhanced the suppressive activities of OSU-CG12 and 2-DG to LNCaP cell viability, while the dominant-negative inhibition of β-TrCP function by ΔF-β-TrCP protected cells against the growth inhibitory effects of both agents (FIG. 8A). Western blot analysis indicates that these effects correlated with the abilities of ectopic WT β-TrCP and ΔF-β-TrCP to promote and suppress, respectively, OSU-CG12- and 2-DG-induced apoptosis, as evidenced by PARP cleavage and increased sub-G1 population, and proteasomal degradation of β-TrCP substrates including cyclin D1 and Sp1 (FIG. 8B).

Increased β-TrCP protein expression is consequent to Sirt1 upregulation. In light of the temporal relationship between the upregulation of β-TrCP protein expression and induction of energy restriction-associated cellular responses, i.e., Sirt1 upregulation, AMPK activation, and ER stress (FIG. 6), the inventors hypothesized that increases in β-TrCP expression might be consequent to one of these hallmark responses. To test this hypothesis, they examined the effects of inhibiting the function and/or expression of Sirt1, AMPK, and GADD153 on the ability of OSU-CG12 to upregulate β-TrCP expression.

The data obtained indicates that enforced expression of the dominant-negative form of Sirt1 (H363YSirt1) reversed the effect of OSU-CG12 on inducing β-TrCP expression and PARP cleavage, a biomarker for apoptosis (FIG. 8C, right panel). This mechanistic link was further corroborated by the finding that ectopic expression of WT Sirt1 led to increased β-TrCP levels in conjunction with reduced expression of its target proteins cyclin D1 and Sp1 in a dose-dependent manner (FIG. 8C, left panel). Furthermore, using nicotinamide and splitomicin, both pharmacological inhibitors of Sirt1 deacetylase activity, evidence was obtained that Sirt1-induced upregulation of β-TrCP expression in OSU-CG12-treated LNCaP cells was attributable to its ability to enhance the stability of β-TrCP protein via a deacetylase-dependent mechanism. First, using cycloheximide to assess protein stability, it was shown that, in vehicle-pretreated cells, β-TrCP exhibited a half-life of less than 12 h (FIG. 8D, left panel). In contrast, OSU-CG12 at 5 μM increased the stability of β-TrCP as the level of β-TrCP protein remained unaltered even in the presence of cyclohexamide for up to 24 h. This stabilizing effect of OSU-CG12 on β-TrCP protein, however, was reversed when cells were co-treated with nicotinamide or splitomicin. Second, RT-PCR analysis confirmed that the mRNA levels of β-TrCP remained unchanged after treatment with OSU-CG12 alone or in the presence of either Sirt1 inhibitor (FIG. 8D, right panel). In addition, pharmacological inhibition of Sirt1 activity could protect LNCaP cells from OSU-CG12-induced cell death in a manner similar to that of the dominant-negative inhibition by ΔF-β-TrCP (data not shown). Together, these findings suggest a causal relationship between the transient TZD- or energy restriction-induced upregulation in Sirt1 expression and the consequent elevation of β-TrCP expression through enhanced protein stabilization.

Figure 9:
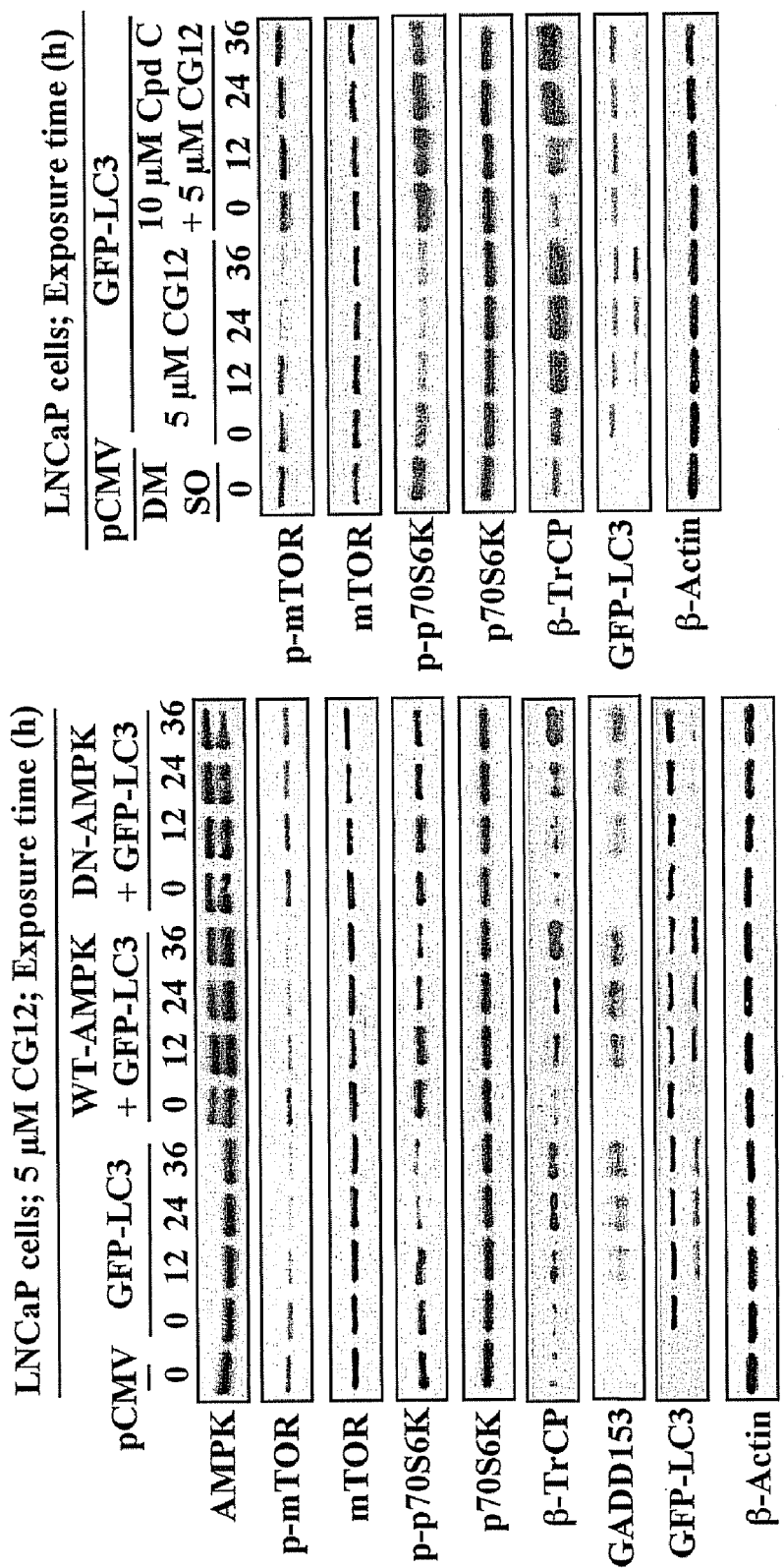
FIG. 9 provides immunoblots showing that the dominant-negative or pharmacological inhibition of AMPK blocked OSU-CG12-mediated autophagy, but had no effect on apoptosis or ER stress. Left panel, effects of the ectopic expression of the wild type (WT) versus the K45R kinase-dead, dominant-negative (DN) form of AMPK on the ability of OSU-CG12 (5 μM) to modulate the expression levels of p-mTOR, p-p70S6K, β-TrCP, and GADD153, the conversion of GFP-LC3, and PARP cleavage in GFP-LC3-expressing LNCaP cells. Right panel, parallel analysis of the effects of Compound C, a pharmacological inhibitor of AMPK.
Figure 11:
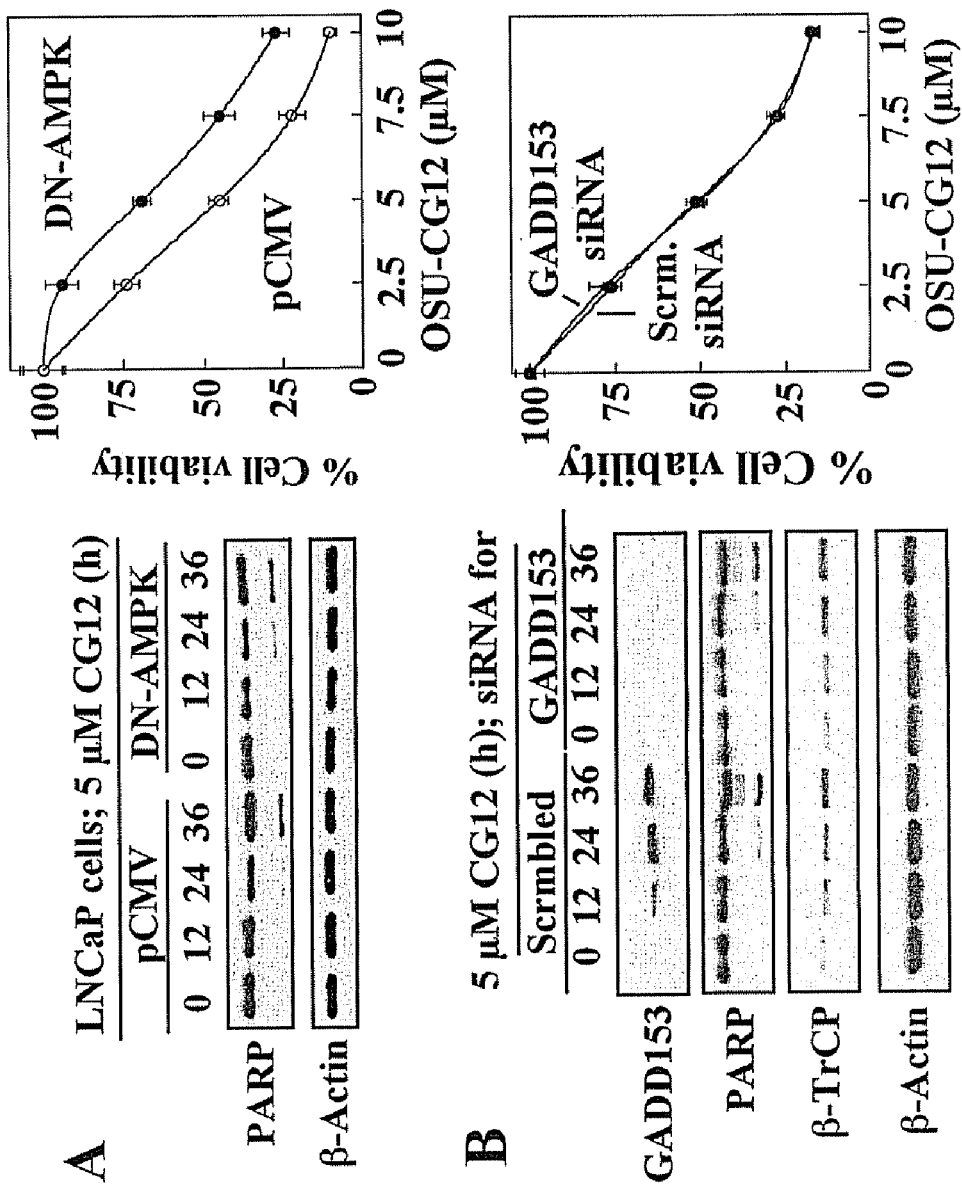
FIG. 11 provides graphs and immunoblots showing that OSU-CG12 induces autophagy by targeting the AMPK/TSC2/mTOR/p70S6K signaling pathway Section A) shows that dominant-negative inhibition of AMPK partially protected LNCaP cells from OSU-CG12-mediated antiproliferative effect. Data are expressed as means±95% confidence intervals (error bars) (n=6). Section B) shows that siRNA-mediated knockdown of GADD153 (DDIT3) did not affect PARP cleavage, β-TrCP induction or AMPK activation. All immunoblots and fluorescence microscopic data are representative of three independent experiments.

In contrast, the dominant-negative and pharmacological inhibition of OSU-CG12-induced AMPK activation failed to affect the upregulation of β-TrCP protein expression (FIG. 9). Similarly, siRNA-mediated silencing of GADD163 expression had no influence on OSU-CG12-induced β-TrCP protein expression (FIG. 11B). These data indicate that activation of AMPK and ER stress does not mediate the TZD- or energy restriction-induced upregulation of β-TrCP expression.

Autophagic cell death plays a role in the antiproliferative effects of energy restriction-mimetic agents.

The findings described above indicate an important role for the Sirt1-β-TrCP pathway in 2-DG and OSU-CG12-induced apoptosis. Subsequently, the inventors assessed the potential roles of AMPK and ER stress signaling in the antitumor effects of energy restriction-mimetic agents. It has been reported that energy restriction induces autophagy via the AMPK-tuberous sclerosis complex (TSC)1/2-mammalian target of rapamycin (mTOR) pathway (Singletary et al., Cancer Epidemiol Biomarkers Prev., 17 p. 1596-1610 (2008)). Thus, blocking AMPK function should prevent LNCaP cells from undergoing autophagy in response to energy restriction-mimetic agents. As shown in FIG. 9, dominant-negative (left panel) or pharmacological inhibition of OSU-CG12-induced AMPK activation, as evidenced by the unchanged phosphorylation level of its downstream targets mTOR and p70S6K, prevented the conversion of GFP-tagged LC3-I to LC3-II, an indicator of autophagosome formation. Moreover, this inhibition of autophagy was independent of drug-induced changes to β-TrCP and ER stress as no effect on the expression levels of β-TrCP or GADD153 were observed in OSU-CG12-treated LNCaP cells.

Figure 10:
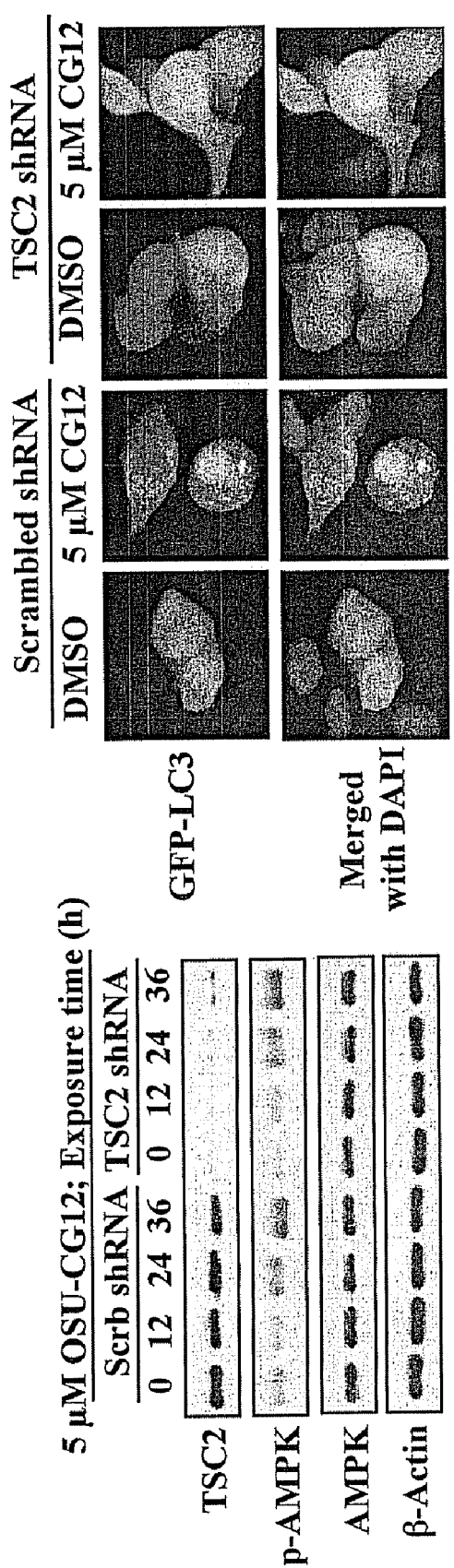
FIG. 10 provides an immunoblot and microscope image showing that shRNA-mediated knockdown of TSC2 protected cells from OSU-CG12-induced autophagy. Left panel, validation of the effectiveness of shRNA-mediated knockdown of TSC2 by western blot analysis of TSC2 and p-AMPK expression in OSU-CG12-treated cells. Right panel, GFP-LC3-expressing LNCaP cells transfected with scrambled or TSC2 shRNA were exposed to DMSO or 5 μM OSU-CG12 for 36 h, and then examined by fluorescence microscopy to assess patterns of GFP-LC3 fluorescence.

Pursuant to this finding, the effect of TSC2 knockdown on OSU-CG12-mediated autophagy was assessed by fluorescence microscopy. Stable transfection of LNCaP cells with TSC2 shRNA led to complete suppression of TSC2 expression, without affecting the ability of OSU-CG12 to activate AMPK (FIG. 10, left panel). Reminiscent of the effect of inhibition of AMPK activation, silencing of TSC2 expression prevented the formation of GFP-LC3-positive puncta by OSU-CG12 (FIG. 10, right panel), confirming the pivotal role of the AMPK/TSC1/2 pathway in OSU-CG12-induced autophagy. Although it is recognized that autophagy parallels apoptosis in governing cancer cell homeostasis in response to therapy, its function in modulating drug-induced cell death by either promoting or inhibiting it varies in different cellular contexts (Tsuchihara et al., Cancer Lett. 278 p. 130-138 (2009)).

To assess the role of autophagy in energy restriction-induced cell death, the effect of inhibiting autophagy by ectopic expression of dominant-negative AMPK on OSU-CG12-mediated apoptosis and suppression of cell viability was examined. Although inhibition of the AMPK-autophagy pathway could not protect cells from OSU-CG12-induced apoptosis, as indicated by PARP cleavage (FIG. 9), MTT data indicate that blocking autophagy substantially reduced OSU-CG12-induced cell death relative to the pCMV control (P<0.01 for all data point) (FIG. 11A), which was also noted in 2-DG and resveratrol-treated cells (data not shown). In contrast, inhibition of ER stress signaling by siRNA-mediated silencing of GADD153 had no effect on PARP cleavage in OSU-CG12-treated LNCaP cells (FIG. 11B); nor did it affect the susceptibility of LNCaP cells to OSU-CG12's antiproliferative activity (data not shown). Together, these findings reveal that, in addition to the Sirt1-β-TrCP pathway, AMPK activation-induced autophagy plays an important role in mediating the antiproliferative effects of energy restriction-mimetic agents in cancer cells.

Discussion

It has long been recognized that cancer cells gain growth advantages in the tumor microenvironment by shifting cellular energy metabolism to aerobic glycolysis, the so-called Warburg effect. See Gatenby et al., Nat. Rev. Cancer, 4 p. 891-899 (2004); Kim et al., Cancer Res., 66 p. 8927-8930 (2006); and Samudio et al., Cancer Res., 69 p. 2163-2166 (2009). This malignancy-associated glycolytic shift constitutes the basis for the molecular imaging of cancer by tracing [$^{18}$F]-fluorodeoxyglucose uptake in positron emission tomography. More recently, there has been a growing interest in targeting aerobic glycolysis for cancer therapy by exploiting the differential susceptibility of malignant versus normal cells to glycolytic inhibition (Chen et al., J Bioenerg Biomembr., 39 p. 267-274 (2007)), as demonstrated by the in vivo efficacy of dietary caloric restriction (Hursting et al., Annu Rev Med., 54 p. 131-152 (2003)), resveratrol (Cucciolla et al., Cell Cycle., 6 p. 2495-2510 (2007)), and 2-DG (Zhu et al., Cancer Res., 65 p. 7023-7030 (2005)) in suppressing carcinogenesis in various spontaneous or chemical-induced tumor animal models. As chronic energy restriction is difficult to implement as a chemopreventive strategy by the general population, 2-DG and resveratrol have received wide attention because of their abilities to mimic the beneficial effects of energy restriction by inhibiting glucose metabolism and uptake, respectively. However, resveratrol and 2-DG exhibit relatively weak in vitro potencies, with $IC_{50}$ values of at least 50 μM and 4 mM, respectively, in blocking glucose metabolism, thereby limiting their therapeutic applications.

The experiments demonstrate that TZDs represent a novel class of energy restriction-mimetic agents considering their ability to elicit hallmark cellular responses characteristic of energy restriction in a manner reminiscent of that of resveratrol and 2-DG. These energy restriction-associated responses included the transient induction of Sirt1 gene expression, and activation of the intracellular fuel sensor AMPK and ER stress (FIG. 11B), culminating in autophagy and apoptosis. These responses, however, could be reversed by the presence of supplemental glucose in the culture medium. Moreover, the TZDs, 2-DG, resveratrol, and glucose deprivation all shared the ability to modulate the phosphorylation states of the signaling kinases examined, including Akt, GSK3β, MAP kinases, and IKKα, which further supports the proposed activity of TZDs as energy restriction-mimetic agents.

Like resveratrol, OSU-CG12 mimicked the effect of energy restriction by blocking glucose uptake, as manifested by a reduced glycolytic rate and decreased production of NADH and lactate. This drug-induced metabolic deficiency signaled the induction of the aforementioned starvation-associated cellular responses, including transient Sirt1 gene expression, AMPK activation, and ER stress, in cancer cells. From a mechanistic perspective, each of these cellular responses mediates a distinct downstream signaling pathway, the interplay among which culminates in OSU-CG12's antiproliferative effects. For example, the data indicate that OSU-CG12-induced AMPK activation led to autophagy via the TSC1/2-mTOR-p70S6K pathway, while that of ER stress signaled the transcriptional activation of the ER chaperones GRP78 and GADD153 via the upregulation of IRE1α, an important mediator of the ER stress response in mammalian cells.

Previous studies have implicated AMPK activation and ER stress as targets for selective cancer cell killing during calorie restriction (Saito et al., Cancer Res., 69 p. 4225-4234 (2009)). However, the role of Sirt1, an $NAD^+$-dependent histone deacetylase in regulating cell death response is less well defined in light of its controversial role as a tumor promoter or tumor suppressor (Deng et al., Int J Biol Sci., 5 p. 147-152 (2009)). Sirt1 exhibits the ability to regulate epigenetic changes as well as the functions of a broad spectrum of nonhistone signaling proteins via deacetylation, including p53, the retinoblastoma protein, NF-κB, several forkhead family transcription factors (FOXOs), MyoD, the DNA repair protein Ku70, and the transcriptional co-activators PCG-1α and p300. While Sirt1 has been shown to enhance cell death or cell cycle arrest through the deacetylating inactivation of NF-κB/RelA (Yeung et al., EMBO J. 23 p. 2369-2380 (2004)), it also inactivates several target proteins involved in tumor suppression and DNA damage repair such as p53, FOXOs and Ku70.

The inventors work provides the first evidence that the transient induction of Sirt1 expression, even with a very short duration, plays an important role in mediating the effect of induction of apoptosis by energy restriction-mimetic agents in cancer cells through the activation of β-TrCP-facilitated proteasomal degradation. This mechanistic link was demonstrated by the ability of the dominant-negative and/or pharmacological inhibition of β-TrCP or Sirt1 to block OSU-CG12- or 2-DG-induced apoptotic death. It is noteworthy that the Sirt1-mediated upregulation of β-TrCP expression was achieved through protein stabilization, for which Sirt1's deacetylase activity was critical. It is plausible that this stabilization of β-TrCP protein is attributable to the ability of Sirt1 to suppress the expression/activity of a specific E3 ligase that targets β-TrCP for proteasome-mediated proteolysis. This potential mechanism is currently under investigation. In addition, although AMPK has been reported to enhance Sirt1 activity by increasing intracellular $NAD^+$ levels, the present data indicate neither genetic nor pharmacological inhibition of AMPK had an effect on β-TrCP expression in TZD-treated cancer cells, suggesting that AMPK activation did not play a major role in upregulating β-TrCP protein stability.

Although substantial evidence has indicated the importance of autophagy in cancer, its role in modulating therapeutic response, by either enhancing or protecting cells from drug-induced cell death, remains unclear. It is plausible that its function varies in response to different death signaling pathways and/or at different stages of tumorigenesis. In the case of energy restriction-mimetic agents, the data provided suggest that the interplay between autophagy and apoptosis plays an important role in mediating their antiproliferative activities.

In conclusion, the findings presented here are noteworthy in three ways. First, the novel function of troglitazone and ciglitazone in targeting energy restriction provides a mechanistic basis to account for their PPARγ-independent effects on a broad spectrum of signaling targets. Second, the inventors have demonstrated for the first time that Sirt1-mediated upregulation of β-TrCP-facilitated proteasomal degradation is an energy restriction-elicited signaling event and is important for the antitumor effects of energy restriction-mimetic agents. Third, the evidence indicates that TZDs mediate antitumor effects by eliciting glucose starvation-associated cellular responses. This finding provides a molecular basis to use these TZDs as scaffolds to develop potent energy restriction-mimetic agents. OSU-CG12 exhibits one- and three-orders-of-magnitude higher potency in eliciting starvation-like cellular responses relative to resveratrol and 2-DG, respectively. The translational value of OSU-CG12 as a chemotherapeutic agent is underscored by its oral bioavailability and effectiveness in suppressing tumor xenograft growth without incurring acute toxicity.

Example II

Ability of Thiazolidinedione Derivatives OSU-CG5 and OSU-CG12 to Suppress Cancer Cell Growth Per the NCI 60 Cell Line Screening Analysis The National Cancer Institute carried out experiments to evaluate the anticancer activity of OSU-CG5 and OSU-CG12 against a variety of different cancers using various different cell lines. For a review of the NCI60 screening method, see Shoemaker, R. H., Nature Reviews, 6: p. 813-823 (2006). More specifically, OSU-CG5 and OSU-CG12 were tested for their ability to inhibit the growth of prostate cancer, breast cancer, leukemia, non-small cell lung cancer, colon cancer, CNS cancer, melanoma, ovarian cancer, and renal cancer cell lines. A variety of different cell lines were used to evaluate the inhibition of each type of cancer. For example, CCFR-CEM, HL-60, K-562, MOLT-4, RPMI-8226, and SR cell lines were used to evaluate the effect of OSU-A9M on leukemia. The data from these experiments demonstrated that both OSU-CG5 and OSU-CG12 exhibited significantly antitumor potency in a variety of different types of cancer cells.

The NCI60 screening method was carried out using the following methodology. The human tumor cell lines of the cancer screening panel were grown in RPMI 1640 medium containing 5% fetal bovine serum and 2 mM L-glutamine. The cells were then inoculated into 96 well microtiter plates in 100 μL at plating densities ranging from 5,000 to 40,000 cells/well depending on the doubling time of individual cell lines. After cell inoculation, the microtiter plates are incubated at 37° C., 5% $CO_2$, 95% air and 100% relative humidity for 24 h prior to addition of the thiazolidinedione derivatives.

After 24 h, two plates of each cell line were fixed in situ with TCA, to represent a measurement of the cell population for each cell line at the time of drug addition (Tz). The thiazolidinedione derivatives were then solubilized in dimethyl sulfoxide at 400-fold the desired final maximum test concentration and stored frozen prior to use. At the time of drug addition, an aliquot of frozen concentrate was thawed and diluted to twice the desired final maximum test concentration with complete medium containing 50 μg/ml gentamicin. Additional four, 10-fold or ½ log serial dilutions were made to provide a total of five drug concentrations plus control. Aliquots of 100 μl of these different drug dilutions are added to the appropriate microtiter wells already containing 100 μl of medium, resulting in the required final drug concentrations.

Following drug addition, the plates were incubated for an additional 48 h at 37° C., 5% $CO_2$, 95% air, and 100% relative humidity. For adherent cells, the assay was terminated by the addition of cold TCA. Cells were fixed in situ by the gentle addition of 50 μl of cold 50% (w/v) TCA (final concentration, 10% TCA) and incubated for 60 minutes at 4° C. The supernatant is discarded, and the plates are washed five times with tap water and air dried. Sulforhodamine B (SRB) solution (100 μl) at 0.4% (w/v) in 1% acetic acid is added to each well, and plates are incubated for 10 minutes at room temperature. After staining, unbound dye is removed by washing five times with 1% acetic acid and the plates are air dried. Bound stain is subsequently solubilized with 10 mM trizma base, and the absorbance was read on an automated plate reader at a wavelength of 515 nm. For suspension cells, the methodology is the same except that the assay is terminated by fixing settled cells at the bottom of the wells by gently adding 50 μl of 80% TCA (final concentration, 16% TCA). Using the seven absorbance measurements [time zero, (Tz), control growth, (C), and test growth in the presence of drug at the five concentration levels (Ti)], the percentage growth is calculated at each of the drug concentrations levels. Percentage growth inhibition is calculated as:

[(Ti−Tz)/(C−Tz)]×100 for concentrations for which Ti>/=Tz

[(Ti−Tz)/Tz]×100 for concentrations for which Ti<Tz.

Three dose response parameters were calculated for each experimental agent. Growth inhibition of 50% (GI50) was calculated from [(Ti−Tz)/(C−Tz)]×100=50, which is the drug concentration resulting in a 50% reduction in the net protein increase (as measured by SRB staining) in control cells during the drug incubation. The drug concentration resulting in total growth inhibition (TGI) was calculated from Ti=Tz. The LC50 (concentration of drug resulting in a 50% reduction in the measured protein at the end of the drug treatment as compared to that at the beginning) indicating a net loss of cells following treatment is calculated from $[(Ti-Tz)/Tz] \times 100 = -50$. Values were calculated for each of these three parameters if the level of activity was reached; however, if the effect is not reached or is exceeded, the value for that parameter is expressed as greater or less than the maximum or minimum concentration tested.

Example III

Development of Novel Adenosine Monophosphate-Activated Protein Kinase Activators In light of the unique ability of the thiazolidinedione family of PPARγ agonists to mediate PPARγ-independent activation of AMPK, the inventors hypothesized that these agents could be pharmacologically exploited to develop potent AMPK activators by dissociating these two pharmacological activities. A two-tiered screening of an in-house, thiazolidinedione-based focused compound library was carried out to identify novel agents that, at low µM concentrations, exhibited the ability to activate AMPK and to inhibit IL-6 production independently of PPARγ in human THP-1 macrophages.

Figure 14:
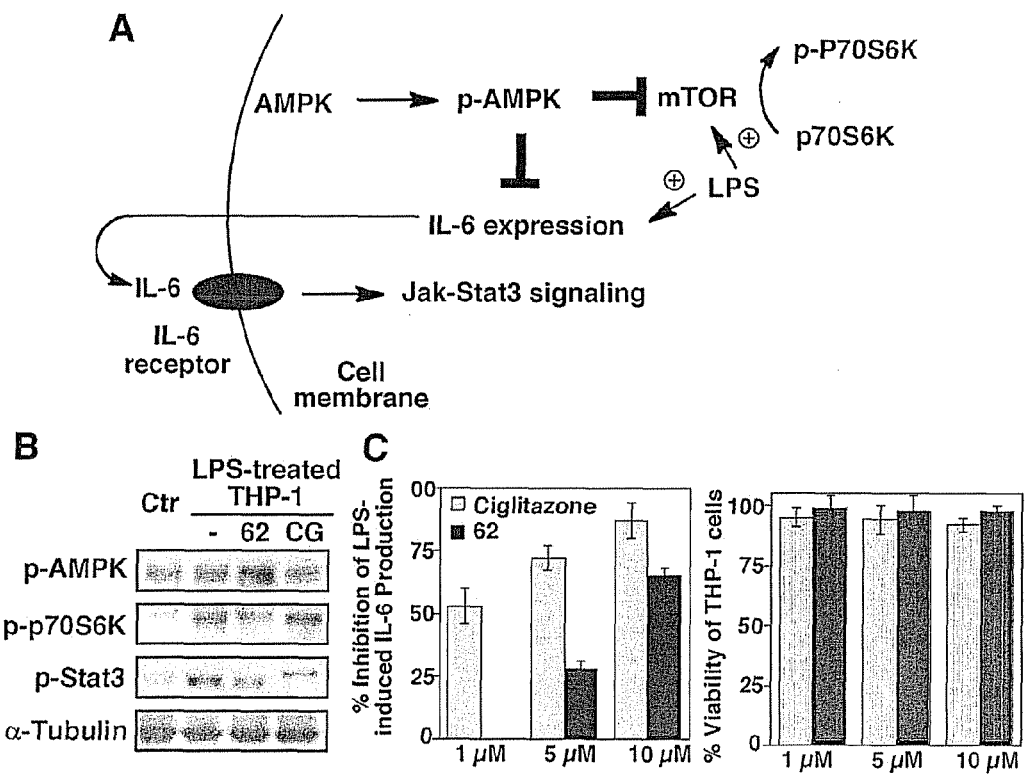
FIG. 14; section (A) provides a schematic representation of the role of AMPK as a negative regulator of mTOR- and IL-6/IL-6 receptor-mediated signaling pathways. Section (B) provides Western blot analysis of the effects of ciglitazone and 62, each at 10 μM, on the phosphorylation of AMPK, p70S6K, and Stat3 in LPS-treated THP-1 cells relative to that on LPS-treated and untreated (Ctr) THP-1 macrophages in 10% FBS-containing medium after 6 h of treatment. (C) Left panel, ELISA analysis of the inhibitory effects of ciglitazone (CG) and 62 at the indicated concentrations on LPS-stimulated IL-6 production in THP-1 macrophages in 10% FBS-containing medium after 6 h of treatment. Columns, mean; bars, SD (N=3). Right panel, the corresponding effects on the viability of THP-1 cells by MTT assays (N=6).

To abolish the PPARγ activity of the thiazolidinediones, the inventors used the unsaturated derivatives of troglitazone and ciglitazone 61 (Δ2TG) and 62 (Δ2CG) as scaffolds to develop a focused compound library consisting of 60 compounds (1-60; FIG. 13). Cell-based assays pertinent to the activation status of AMPK and mTOR [i.e., phosphorylation levels of AMPK and p70 ribosomal protein S6 kinase (p70S6K), respectively] and IL-6/IL-6 receptor signaling [i.e., IL-6 production and Signal transducer and activator of transcription 3 (Stat3) phosphorylation, respectively] in lipopolysaccharide (LPS)-stimulated THP-1 macrophages were used to screen this compound library via Western blotting and enzyme-linked immunosorbent assay (ELISA) (FIG. 14A). The first-tier screening of individual compounds at 10 µM netted eight active agents (8, 12, 21, 31, 42, 49, 53, and 54), which were classified into three structural series (FIG. 12A). A further examination of the ability of these agents at 1 µM to block the LPS-stimulated production of IL-6 identified compound 53 as the optimal agent. General procedures for the synthesis of series A-C compounds are depicted in FIG. 12B.

Methods

Cells and cell culture. THP-1 monocytic cells were purchased from the American Type Culture Collection (Rockville, Md.), and maintained with L-glutamine-containing RPMI 1640 supplemented with 10% fetal bovine serum (FBS), 0.25% glucose, 0.01% sodium pyruvate, 50 µM 2-mercaptoethanol, and 0.1 ml/ml penicillin/streptomycin/L-glutamine. Differentiation of THP-1 monocytes into macrophages was carried out by exposure to PMA (50 nM) in the aforementioned RPMI 1640 medium for 24 h. Colon-26 (C-26) adenocarcinoma cells were provided by a researcher at The Ohio State University. The C-26 cells were maintained in RPMI 1640 medium supplemented with 5% FBS and 1% penicillin/streptomycin. All cell types were cultured at 37° C. in a humidified incubator containing 5% $CO_2$.

ELISA. IL-6 release by differentiated THP-1 macrophages in response to 10 ng/ml of LPS was analyzed by using the IL-6 ELISA kit (Cayman Chemical Co.; Ann Arbor, Mich.) according to the manufacturer's instruction in triplicate. The effect of each test compound on LPS-stimulated IL-6 release is presented as percent inhibition and was calculated using the following formula: percentage inhibition=100%×{1−[(O.D. of sample−O.D. of control)/(O.D. of LPS−O.D. of control)]}.

Western blotting. THP-1 cells were lysed in SDS-sample buffer after washing with iced-PBS buffer, and then heated at 95° C. for 20 minutes. Protein extracts were prepared using M-PER mammalian protein extraction reagent (Pierce, Rockford, Ill.), containing freshly added 1% phosphatase and protease inhibitor cocktails (Calbiochem). After centrifugation of lysates at 13000 g for 10 min, supernatants were collected, and the protein concentration in each sample was determined by protein assay (Bio-Rad). Protein extracts were then suspended in 2×SDS sample buffer, separated by electrophoresis in 10% SDS-polyacrylamide gels, and transferred to nitrocellulose membranes using a semidry transfer cell. The transblotted membrane was washed twice with Tris-buffered saline containing 0.1% Tween-20 (TBST). After blocking with TBST containing 5% nonfat milk for 1 h, the membrane was incubated with primary antibodies: p172Thr-AMPK, AMPK, p705Tyr-STAT3 and STAT3 (Cell Signaling Technology; Beverly, Mass.); p389Thr-p70S6K and p70S6K (Santa Cruz Biotechnology; Santa Cruz, Calif.), each at 1:1,000 dilution in 1% TBST-nonfat milk at 4° C. overnight. After incubation with the primary antibody, the membrane was washed three times with TBST for a total of 30 min, followed by incubation with horseradish peroxidase-conjugated goat anti-mouse IgG (diluted 1:2500) for 1 h at room temperature. After three thorough washes with TBST for a total of 30 min, the immunoblots were visualized by enhanced chemiluminescence Transient transfection. Transfection of THP-1 cells with the K45R kinase-dead, dominant-negative AMPK plasmid (Addgene, Cambridge, Mass.) or empty vector was performed by electroporation using the Human Monocyte Nucleofector Kit of the Amaxa Nucleofector System (Amaxa Biosystems, Cologne, Germany) according to Schnoor et al., J Immunol Methods, 344, 109-115 (2009).

Analysis of PPARγ Activation. The PPRE-x3-TK-Luc reporter vector containing three copies of the PPAR response elements preceding the thymidine kinase promoter-luciferase construct was used for detection of PPARγ activation. Differentiated THP-1 macrophages were plated at the density of $1 \times 10^5$ cells/per well in 24-well plates and then transiently transfected by nucleofection with the PPRE-x3-TK-Luc reporter plasmid followed by exposure to 10 µM ciglitazone or its derivatives in triplicate in the presence of LPS for 48 h. Cells were lysed with passive lysis buffer (Promega), and aliquots of the lysates (50 µL) were transferred to 96-well plates and mixed with 100 µL of luciferase substrate (Promega). Luciferase activity was determined by using the MicroLumatPlus LB96V luminometer (Berthold Technologies, Oak Ridge, Tenn.) with the WinGlow software package.

Total RNA isolation and RT-PCR analysis of IL-6 expression. Total RNA was extracted from drug- or vehicle-treated THP-1 macrophages with TRIzol (Invitrogen; Carlsbad, Calif.), and then reverse-transcribed to cDNA using the Omniscript RT Kit (Qiagen, Valencia, Calif.). Suitable IL-6: forward and reverse; and β-actin: forward and reverse primers were used. The PCR products were separated by electrophoresis on 1% agarose gels and visualized by ethidium bromide staining.

Molecular model experiment. Molecular structures of compound 53, A-769662, and PT1 were initially subjected to 1000 steps of Monte Carlo simulation using Merck Molecular Force Field program available in Spartan '08 (Wavefuction, Inc., Irvine, Calif.). The minimum conformation reached by the simulation was then fully optimized at a density function theory level of B3LYP/6-31G* with Gaussian 03 (Gaussian, Inc., Wallingford, Conn.). All the fully optimized structures were confirmed by normal mode analysis; no negative frequencies were found. Computations for electrostatic potential and density were carried out for each optimal structure by potential population analysis under Hartree-Fock/6-31G* function theory by using Gaussian 03. The electrostatic potential map for each compound was generated by Molecular Operation Environment 2008 (Chemical Computing Group, Montreal, Canada) and are presented with the electrostatic potential mapped onto the electron density.

Results

Proof-of-concept that thiazolidinediones can be structurally optimized to develop potent AMPK activators.

The inventors used phorbol 12-myristate 12-acetate (PMA)-differentiated THP-1 cells, a cell line model mimicking many characteristic features of primary macrophages, to examine the effect of thiazolidinedione derivatives on AMPK activation and LPS-induced mTOR activation and IL-6 secretion into the medium. In addition, the phosphorylation of p70S6K and Stat3 were monitored as markers for the activation status of mTOR and IL-6 receptor signaling pathways, respectively, in drug-treated cells (FIG. 14A). Consistent with a recent report that high doses of ciglitazone ($\geqq 100$ μM) were required to activate AMPK (Wang et al., Cancer Res., 68, 4640-4648 (2008)) the data indicate that ciglitazone at 10 μM exhibited no appreciable effect on the levels of p-AMPK or p-p70S6K relative to the LPS-treated control after 6 h of treatment (FIG. 14B). In contrast, its PPARγ-inactive counterpart 62 at the same concentration was effective in elevating the level of p-AMPK, accompanied by a parallel decrease in p70S6K phosphorylation. Nevertheless, ciglitazone displayed a several-fold higher potency than 62 in inhibiting LPS-stimulated IL-6 production (FIG. 14C), suggesting that the anti-IL-6 activity of ciglitazone was primarily attributable to a PPARγ-dependent mechanism. This reduction in IL-6 production was not due to drug-induced cell death as neither agent inhibited the viability of THP-1 cells within the dose range examined. Moreover, the ability of ciglitazone and 62, at 10 μM, to suppress LPS-activated IL-6 receptor signaling was evident by reduced Stat3 phosphorylation relative to the control (FIG. 13B).

Screening of an in-house, benzylidene-thiazolidinedione-based focused compound library to identify effective AMPK activators with high potency in suppressing IL-6 production.

Figure 15:
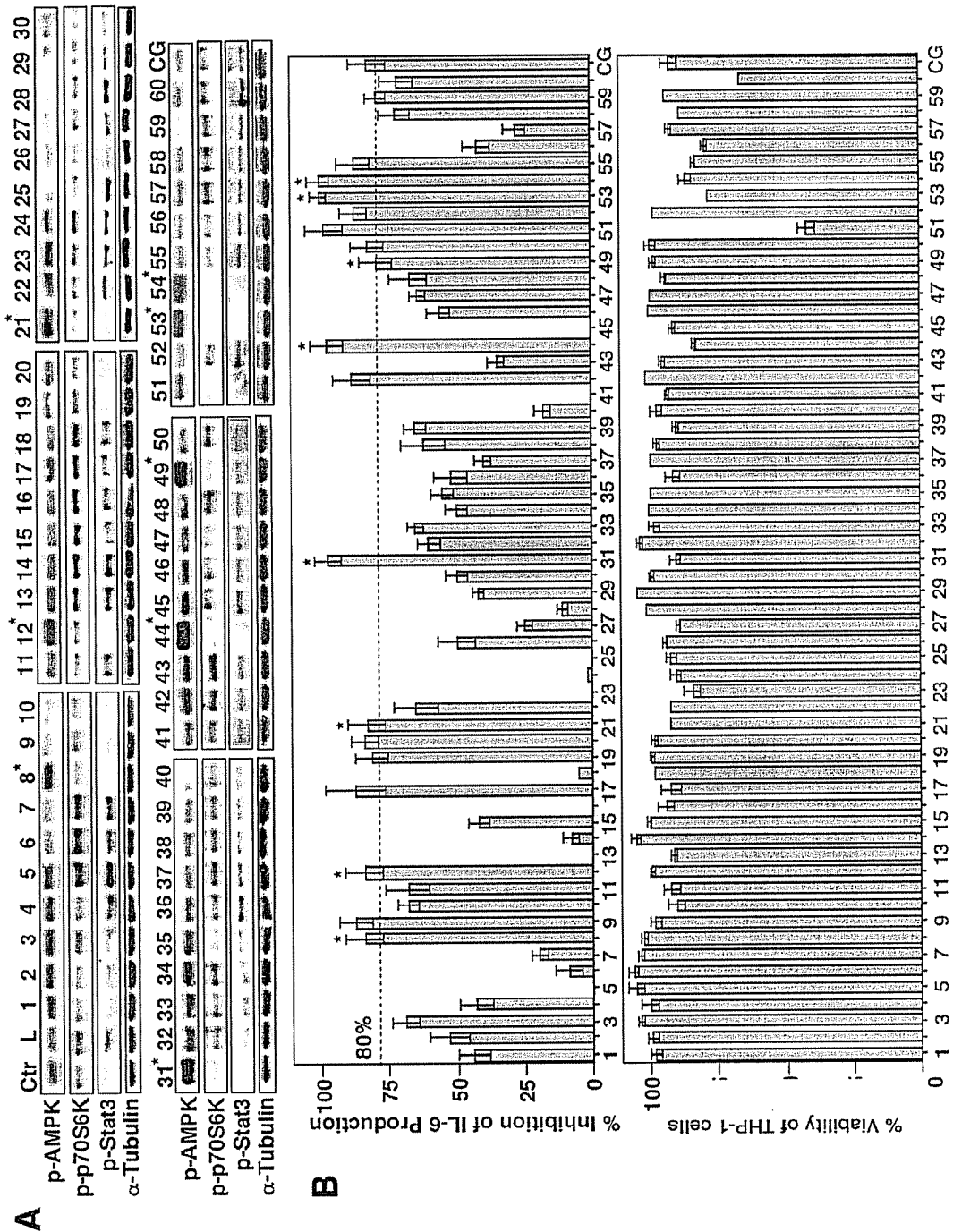
FIG. 15; section (A) provides a Western blot analysis of the effects of compounds 1-60 vis-à-vis ciglitazone (CG), each at 10 μM, on the phosphorylation of AMPK, p70S6K, and Stat3 in LPS-treated THP-1 cells relative to that in LPS only-treated (L) and untreated (Ctr) THP-1 macrophages in 10% FBS-containing medium after 6 h of treatment. Section (B) Upper panel, provides an ELISA analysis of the inhibitory effects of compounds 1-60 vis-à-vis ciglitazone (CG), each at 10 μM, on LPS-stimulated IL-6 production in THP-1 macrophages in 10% FBS-containing medium after 6 h of treatment. Columns, mean; bars, SD (N=3). In the lower panel, the corresponding effects on the viability of THP-1 cells by MTT assays (N=6) is shown.

Based on the above finding, 61 and 62 were used as scaffolds to generate a focused compound library consisting of 60 derivatives with diverse structures, in which 62 was blindly embedded as a control (compound 33) during the screening process (FIG. 13). These compounds along with ciglitazone, each at 10 μM, were assessed for their abilities to activate AMPK and to inhibit IL-6 production in LPS-stimulated THP-1 cells (FIG. 15). Consistent with the earlier finding, 10 μM 62 exhibited modest activities in AMPK activation and against IL-6 secretion, in conjunction with the inhibition of the phosphorylation of p70S6K and Stat3, while ciglitazone was effective in inhibiting IL-6 production without affecting AMPK phosphorylation status. Of the other compounds examined, eight derivatives (8, 12, 21, 31, 44, 49, 53, 54) exhibited substantially higher potencies relative to 62 in the overall assessment of all of these markers (FIG. 15; only those with greater than 80% inhibition of IL-6 production were selected). Again, none of these agents caused significant suppression of THP-1 cell viability (FIG. 15B, lower panel), indicating that the inhibition of IL-6 production was not due to cell death. It is interesting to note that some of the agents in the library showed activities in AMPK activation, but lacked effects on suppressing IL-6 production (e.g., compounds 4 and 5), or vice versa (e.g., compounds 9, 19, 51, 52, 55 and 59), suggesting the involvement of alternative mechanisms in their modes of action.

Figure 16:
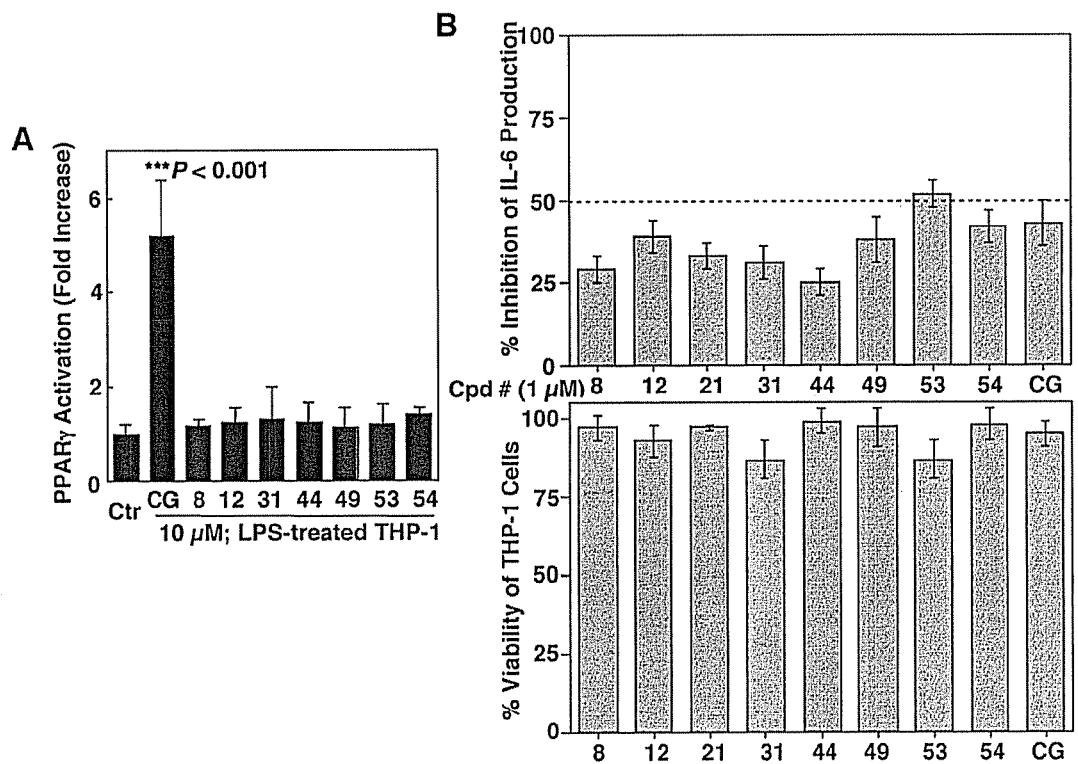
FIG. 16; section (A) shows the effects of compounds 8, 12, 31, 44, 49, 53 and 54 vis-à-vis ciglitazone (CG), each at 10 μM, on PPARγ activation in differentiated THP-1 cells. THP-1 cells were transiently transfected with the PPRE-x3-TK-Luc reporter vector and then exposed to individual agents or DMSO vehicle in 10% FBS-supplemented RPMI 1640 medium for 48 h. Columns, mean; bars, SD (N=6). Section (B) The upper panel, provides an ELISA analysis of the inhibitory effects of compounds 8, 12, 21, 31, 44, 49, 53 and 54 vis-à-vis ciglitazone (CG), each at 1 μM, on LPS-stimulated IL-6 production in THP-1 macrophages in 10% FBS-containing medium after 6 h of treatment. Columns, mean; bars, SD (N=3). The lower panel shows the corresponding effects on the viability of THP-1 cells by MTT assays (N=6).

To demonstrate that the drug-induced inhibition of IL-6 production was independent of PPARγ, the ability of these eight agents versus ciglitazone to transactivate PPARγ was examined by using the PPAR response element (PPRE) luciferase reporter assay. In THP-1 cells transiently transfected with a reporter construct (PPRE-x3-TK-Luc), ciglitazone at 10 μM significantly increased luciferase activity (P<0.001) (FIG. 16A). In contrast, none of the eight agents examined showed appreciable activity in PPARγ activation.

Compound 53 represents the lead agent in AMPK activation and IL-6 repression.

The activities of these candidate agents vis-à-vis ciglitazone in blocking IL-6 release were further assessed at 1 μM. As shown, compound 53 showed the highest potency, exceeding that of ciglitazone, followed by 54 and 49 (FIG. 16B, upper panel), all three of which possess largely shared structural motifs with variations in substituents. Again, this inhibition of IL-6 production was not due to cell death as none of these agents exhibited a significant effect on THP-1 cell viability (lower panel).

Compound 53 inhibited LPS-stimulated IL-6 production in a dose-dependent manner, with an $IC_{50}$ of approximately 1 μM (FIG. 17A), paralleling its effect on the intracellular IL-6 mRNA expression (FIG. 17B) and the phosphorylation levels of AMPK and p70S6K (FIG. 17C). Moreover, the potency of compound 53 in activating AMPK is about two-orders-of-magnitude higher than that of AICAR (FIG. 17C).

To establish the mechanistic link between AMPK activation and anti-IL-6 activity, the effect of the dominant-negative (DN) inhibition of AMPK via the ectopic expression of the K45R kinase-dead mutant (FIG. 18A) was examined. Relative to the pCMV control, transient transfection of differentiated THP-1 cells with the DN-AMPK mutant significantly enhanced LPS-induced IL-6 production and reversed the inhibitory effect of compound 53 (10 μM) (FIG. 18B). This finding suggests that AMPK activation is essential to the ability of compound 53 to suppress LPS-stimulated IL-6 production.

The effect of compound 53 on the phosphorylation of AMPK and p70S6K was further assessed in C-26 colon adenocarcinoma cells, a cell model commonly used for studying cancer cachexia. Similar to that observed in THP-1 cells, compound 53 mediated robust increases in the p-AMPK level in dose- and time-dependent manners, accompanied by parallel decreases in p-p70S6K (FIG. 18C). It is noteworthy that this AMPK activation occurred almost immediately following drug treatment. Together, these findings confirmed that this drug effect was not a cell line-specific event.

Compounds 53 and 54 were also tested for their ability to inhibit the growth of various different cancer cell lines. The cancer cell lines used were PC-3, LNCap, MCF-7, and MDA-MB-231. The amount of inhibition at 24 hours, 48 hours, and 72 hours is shown in FIG. 19.

Discussion

Recent evidence suggests that AMPK serves as a metabolic checkpoint by integrating growth factor signaling with cellular metabolism through the negative regulation of mTOR. Carling, D., Trends Biochem Sci, 29, 18-24 (2004) This functional role underscores the therapeutic value of targeting AMPK activation in different diseases ranging from insulin resistance to cancer through the regulation of energy metabolism. For example, a recent study demonstrates that AICAR was effective in suppressing the growth of EGFR-activated glioblastoma cells by inhibiting cholesterol and fatty acid biosynthesis. Guo et al., Proc Natl Acad Sci USA, 106, 12932-12937 (2009).

Thus, this example was aimed at the pharmacological exploitation of thiazolidinediones to develop novel AMPK activators. Although AMPK is a highly conserved sensor of cellular energy status, its functional role varies in a cell context- and cell type-specific manner. Here, differentiated THP-1 macrophages were used as a cellular platform to conduct drug screening in light of the pivotal role of AMPK, as a negative regulator of mTOR, in promoting the anti-inflammatory phenotype of macrophages by suppressing the production of inflammatory cytokines such as IL-6. By screening an in-house, thiazolidinedione-based focused compound library, this cell-based assay identified compound 53 as the lead agent with low μM potency in activating AMPK and inhibiting LPS-induced IL-6 secretion in THP-1 cells. It was further demonstrated that this drug-induced suppression of LPS-stimulated IL-6 production was attributable to AMPK activation, which contrasts with the PPARγ-dependent mechanism of ciglitazone. Nevertheless, it was found that a number of the agents examined, though inactive in AMPK activation, exhibited significant effect on IL-6 production (compounds 9, 19, 51, 52, 55 and 59). From a mechanistic perspective, separation of these two pharmacological activities suggests diversity in the mode of action among these pharmacological agents. The premise is manifest by the ability of a number of small-molecule agents to modulate IL-6 production through distinct mechanisms. For example, luteolin, a flavonoid, reduced LPS-induced IL-6 production by inhibiting the Jun N-terminal kinase (JNK)-activator protein (AP)-1 pathway, (Jang et al., Proc Natl Acad Sci USA, 105, 7534-7539 (2008)) while chloroquine-mediated inhibition of IL-6 expression was associated with reduced mRNA stability and mRNA levels. Jang et al., Rheumatology (Oxford), 45, 703-710 (2006). In addition, the bisphosphonate zoledronic acid was also reported to downregulate IL-6 gene expression in prostate cancer cells though the underlying mechanism is unclear. Asbagh et al., Int Braz J Urol, 34, 355-363 (2008). In contrast, many therapeutic agents are associated with the upregulation of IL-6 expression, including paclitaxel through the activation of the JNK and Toll-like receptor 4 signaling pathways and the multi-kinase inhibitor sunitinib through a yet-to-be-identified mechanism. Consequently, understanding the mechanism of this AMPK-independent induction will shed light onto the regulation of IL-6 production.

Recently, two direct, small-molecule activators of AMPK, A-769662 and PT1, were discovered, each of which exhibits a unique mode of activation. Cool et al., Cell Metab, 3, 403-416 (2006) Evidence suggests that allosteric binding of A-769662 to the AMPK γ subunit stabilizes a conformation of AMPK that inhibits dephosphorylation at the Thr-172, while PT1 antagonizes AMPK auto-inhibition by binding to the α subunit near the auto-inhibitory domain. Pang et al., J Biol Chem, 283, 16051-16060 (2008). Although the mode of protein-ligand recognition remains unclear, molecular docking of PT1 into AMPK α1 suggests that the binding is mainly attributable to electrostatic interactions. As compound 53 contains many electron-rich moieties as A-769662 and PT1 do, molecular modeling analysis was carried out to compare the electrostatic potential of these compounds (FIG. 18D). As shown, the electrostatic potential map of compound 53 exhibited some degree of similarity to that of PT1, and, to a lesser extent, A-769662. This finding suggests that compound 53 might mediate AMPK activation through an allosteric binding mechanism similar to that of PT1 or A-769662, which constitutes the current focus of this investigation.

As AMPK represents a therapeutically relevant target for the treatment of the metabolic syndrome and cancer, (Luo, et al., Trends Pharmacol Sci, 26, 69-76 (2005); Zhang et al., Cell Metab, 9, 407-416 (2009)) there is a growing interest in the development of novel pharmacological activators for this fuel-sensing enzyme. However, questions remain regarding the potential adverse effects of sustained pharmacological activation of AMPK, especially in the liver and skeletal muscle. In the face of this challenge, understanding the functional role of AMPK isozymes in different tissues as a prelude to designing isozyme-specific activators and/or tissue-selective delivery represents an urgent issue.

Conclusion

In light of the high potency of compound 53 in activating AMPK and inhibiting IL-6 production, it serves as a useful agent to investigate the effects of modulating these two signaling effectors in the therapeutic intervention of different diseases in cell and animal models. In addition, characterization of its mechanism in AMPK activation will shed light onto the functional regulation of AMPK, which might lead to the identification of additional AMPK activators.

Example IV

Preparation of Adenosine Monophosphate-Activated Protein Activators

Chemical reagents and organic solvents were purchased from Sigma-Aldrich (St. Louis; MO) unless otherwise mentioned. Nuclear magnetic resonance spectra ($^1$H NMR) were measured on a Bruker DPX 300 model spectrometer. Chemical shifts (δ) were reported in parts per million (ppm) relative to the TMS peak. Electrospray ionization mass spectrometry analyses were performed with a Micromass Q-T of II high-resolution electrospray mass spectrometer. The purities of all tested compounds are higher than 95% by elemental analyses, which were performed by Atlantic Microlab, Inc. (Norcross, Ga.), and were reported to be within 0.4% of calculated values. Flash column chromatography was performed using silica gel (230-400 mesh). The structures of the eight lead candidates could be divided into three series, i.e., A (8, 12, and 21), B (31 and 44), and C (49, 53, and 54) (FIG. 12A). The general procedures for the synthesis of series A-C compounds are described in FIG. 12B. Compounds of series A and B were synthesized according to slight modifications of previously reported procedures. Huang et al., J Med Chem, 49, 4684-4689 (2006); Yang et al., J Med Chem, 51, 2100-2107 (2008). The synthesis of the series C active compounds (49, 53, and 54) is illustrated by the synthesis of compound 53 as an example.

5-[3-Bromo-4-(6-ethoxy-2,5,7,8-tetramethyl-chroman-2-ylmethoxy)-benzylidene]-thiazolidine-2,4-dione (8). $^1$H NMR (300 MHz, CDCl$_3$), δ 1.42 (t, J=7.2 Hz, 3H), 1.51(s, 3H), 1.92-2.03(m, 1H), 2.05-2.23 (m, 10H), 2.58-2.72 (m, 2H), 3.74 (q, J=7.2 Hz, 2H), 4.14 (q, J=9.3 Hz, 2H), 7.00 (d, J=8.4 Hz, 1H), 7.41 (dd, J=2.4, 8.4 Hz, 1H), 7.71 (d, J=2.4 Hz, 1H), 7.75 (s, 1H), 8.65 (s, 1H). HRMS exact mass of C$_{26}$H$_{28}$BrNO$_5$S (M+Na)+, 568.0769 amu; observed mass of (M+Na)+, 568.0786 amu. Anal. calcd C, 57.14; H, 5.16; O, 14.64. found C, 57.23; H, 5.26; O, 14.66.

5-[4-(6-Butoxy-2,5,7,8-tetramethyl-chroman-2-ylmethoxy)-3-methoxy-benzylidene]-thiazolidine-2,4-dione (12). $^1$H NMR (300 MHz, CDCl$_3$), δ 0.99 (t, J=7.2 Hz, 3H), 1.45 (s, 3H), 1.52-1.66 (m, 2H), 1.73-1.85(m, 2H), 1.89-1.99 (m, 1H), 2.02-2.23 (m, 10H), 2.60-2.69 (m, 2H), 3.63 (t, J=6.6 Hz, 2H), 3.90 (s, 3H), 4.04 (d, J=9.3 Hz, 1H), 4.12 (d, J=9.3 Hz, 1H), 6.96-7.10 (m, 3H), 7.80 (s, 1H), 8.58 (br, 1H). HRMS exact mass of C$_{29}$H$_{35}$NO$_6$S (M+Na)+, 548.2083 amu; observed mass of (M+Na)+, 548.2095 amu. Anal. calcd C, 66.26; H, 6.71; O, 18.26. found C, 66.32; H, 6.80; O, 18.29.

4-{2-[2-Bromo-4-(2,4-dioxo-thiazolidin-5-ylidenemethyl)-phenoxymethyl]-2,5,7,8-tetramethyl-chroman-6-yloxy}-butyronitrile (21). $^1$H NMR (300 MHz, CDCl$_3$), δ 1.49 (s, 3H), 1.94-2.23 (m, 13H), 2.58-2.74 (m, 4H), 3.76 (t, J=5.7 Hz, 2H), 4.00-4.16 (m, 2H), 6.97 (d, J=8.7 Hz, 1H), 7.40 (dd, J=2.1, 8.7 Hz, 1H), 7.70 (d, J=2.1 Hz, 1H), 7.74 (s, 1H), 8.36 (br, 1H). HRMS exact mass of C$_{28}$H$_{29}$BrN$_2$O$_5$S (M+Na)+, 607.0878 amu; observed mass of (M+Na)+, 607.0882 amu. Anal. calcd C, 57.44; H, 4.99; O, 13.66. found C, 57.54; H, 5.04; O, 13.72.

5-(4-Hydroxy-3-trifluoromethyl-benzylidene)-3-(1-methyl-cyclohexylmethyl)-thiazolidine-2,4-dione (31). $^1$H NMR (300 MHz, CDCl$_3$) 0.95 (s, 3H), 1.46-1.56 (m, 10H), 3.64 (s, 2H), 6.08-6.38 (br, 1H), 7.09 (d, J=8.4 Hz, 1H), 7.59 (d, J=8.4 Hz, 1H), 7.69 (s, 1H), 7.83 (s, 1H). HRMS exact mass of C$_{19}$H$_{20}$F$_3$NO$_3$S, (M$^+$Na)$^+$, 422.1014 amu; found: 422.1012 amu. Anal. calcd C, 57.13; H, 5.05; O, 12.02. found C, 57.38; H, 5.04; O, 12.16.

5-(4-Hydroxy-3-trifluoromethyl-benzylidene)-3-propyl-thiazolidine-2,4-dione (44). $^1$H NMR (300 MHz, CDCl$_3$) 0.97 (t, J=7.5 Hz, 3H), 1.60-1.78 (m, 2H), 3.74 (t, J=7.5 Hz, 2H), 6.19 (br, 1H), 7.09 (d, J=8.4 Hz, 1H), 7.59 (d, J=8.4 Hz, 1H), 7.69 (s, 1H), 7.83 (s, 1H). HRMS exact mass of C$_{14}$H$_{12}$F$_3$NO$_3$S, (M$^+$Na)$^+$, 331.3112 amu; found: 331.3124 amu. Anal. calcd C, 50.75; H, 3.65; O, 14.49. found C, 50.84; H, 3.68; O, 14.54.

N-{4-[3-(1-Methyl-cyclohexylmethyl)-2,4-dioxo-thiazolidin-5-ylidene-methyl]-phenyl}-4-nitro-3-trifluoromethyl-benzenesulfonamide (53) Step a. Trifluoro-methanesulfonic acid 1-methyl-cyclohexylmethyl ester (i) was prepared from 1-methylcyclohexanecarboxylic acid as previously described. Yang et al., J Med Chem, 51, 2100-2107 (2008). A mixture of i (0.5 mmol), 2,4-thiazolidinedione (0.6 mmol) and K$_2$CO$_3$ (0.7 mmol) were dissolved in DMF (3 mL), heated to 80° C. with stirring for 4 hr, poured into water, extracted with ethyl acetate (10 mL) three times, and concentrated. The residue was purified by flash column chromatography to afford 3-(1-methyl-cyclohexylmethyl)-thiazolidine-2,4-dione (ii) in 50% yield.

Step b. To a mixture of methyl 4-aminobenzoate (1.51 g, 10 mmol) and pyridine (0.97 mL) in dry methylene chloride (100 mL), 4-nitro-3-trifluoromethylbenzenesulfonyl chloride (2.89 g, 10 nmol) in dry methylene chloride (20 mL) was added slowly, and washed, in tandem, with 1N HCl, water, 10% Na$_2$CO$_3$ aqueous solution, and brine. The organic layer was dried, filtered, and concentrated. The residue was purified by chromatography (EtOAc-hexane, 1:5) to give 4-(4-nitro-3-trifluoromethyl-phenyl-sulfamoyl)-benzoic acid methyl ester (iii) as colorless crystal with 86% yield. $^1$H NMR (300 MHz, CDCl$_3$) δ 3.79 (s, 3H), 7.25 (d, J=5.58 Hz, 2H), 7.85 (d, J=6.72 Hz, 2H), 7.94 (d, J=8.43 Hz, 1H), 8.16 (d, J=8.64 Hz, 1H), 8.30 (s, 1H).

Step c. To a solution of compound iii (3.26 g, 8.06 mmol) in dry THF (50 mL), LAH pallet (0.46 g, 12.10 mmol) was added at 0° C. The resulting reaction mixture was stirred for 4 h, quenched by the addition of water (5 mL), concentrated, diluted with ethyl acetate (50 mL), and washed, in tandem, with 1N HCl, water, 10% Na$_2$CO$_3$ aqueous solution, and brine. The organic layer was dried, filtered, and concentrated. The residue was purified by silica gel chromatography (ethyl acetate-hexane, 3:7) to afford 4-hydroxymethyl-N-(4-nitro-3-trifluoromethyl-phenyl)-benzenesulfonamide (iv) as light yellow solid with 71% yield. $^1$H NMR (300 MHz, CDCl$_3$) δ 2.06 (br, 1H), 4.75 (s, 2H), 6.96 (br, 1H), 7.59 (d, J=10.17 Hz, 2H), 7.84 (d, J=8.19 Hz, 2H), 7.88 (d, J=8.43 Hz, 1H), 8.03 (d, J=8.43 Hz, 1H), 8.16 (s, 1H).

Step d. A reaction mixture of compound Iv (2.00 g, 5.31 mmol) and MnO$_2$ (2.34 g, 26.57 mmol) in chloroform (100 mL) was refluxed overnight, concentrated, diluted with ethyl acetate, filtered, and concentrated. The residue was purified by silica gel chromatography (ethyl acetate-hexane, 1:7) to yield N-(4-formyl-phenyl)-4-nitro-3-trifluoromethyl-benzenesulfonamide (v) as light yellow solid in 88% yield. $^1$H NMR (300 MHz, CDCl$_3$) δ 7.28 (d, J=6.76 Hz, 2H), 7.88 (d, J=6.72 Hz, 2H), 7.97 (d, J=8.43 Hz, 1H), 8.17 (d, J=8.64 Hz, 1H), 8.31 (s, 1H).

Step e. A reaction mixture of compound ii (0.73 g, 3.21 mmol), compound vi (1.25 g, 3.21 mmol), and catalytic amount of piperidine in ethyl alcohol (50 mL) was refluxed overnight, concentrated, dissolved in ethyl acetate (50 mL), neutralized with acetic acid, washed with water and brine, dried, and concentrated. The residue was purified by silica gel chromatography (ethyl acetate-hexane, 1:7) to give afforded compound 53 as yellow solid in 72% yield. $^1$H NMR (300 MHz, d-DMSO) δ 0.80 (s, 3H), 1.20-1.43 (m, 10H), 3.47 (s, 2H), 7.24 (d, J=7.65 Hz. 2H), 7.52 (d, J=8.28 Hz, 2H), 7.78 (s, 1H), 8.26 (s, 1H), 8.31 (s, 1H), 11.12 (br, 1H). HRMS exact mass of C$_{25}$H$_{24}$F$_3$N$_3$O$_6$S$_2$, (M$^+$Na)$^+$, 606.0956 amu; found: 606.0974 amu. Anal. calcd C, 51.45; H, 4.15; O, 16.45. found C, 51.72; H, 4.20; O, 16.54.

4-Methoxy-N-{4-[3-(1-methyl-cyclohexylmethyl)-2,4-dioxo-thiazolidin-5-yli-denemethyl]-phenyl}-benzenesulfonamide (49). $^1$H NMR (300 MHz, CDCl$_3$/MeOD-D$^4$) 0.96 (s, 3H), 1.22-1.62 (m, 10H), 3.66 (s, 2H), 3.91 (s, 3H), 7.02 (d, J=8.7 Hz, 2H), 7.55 (d, J=8.7 Hz, 2H), 7.79 (d, J=8.1 Hz, 2H), 7.87 (d, J=8.1 Hz, 2H), 7.88 (s, 1H). HRMS exact mass of C$_{26}$H$_{28}$N$_2$O$_5$S$_2$, (M$^+$Na)$^+$, 535.1337 amu; found: 535.1352 amu. Anal. calcd C, 60.92; H, 5.51; O, 15.60. found C, 60.72; H, 5.60; O, 15.54.

N-{4-[3-(1-Methyl-cyclohexylmethyl)-2,4-dioxo-thiazolidin-5-ylidenemethyl]-phenyl}-4-nitro-benzenesulfonamide (54). $^1$H NMR (300 MHz, d-DMSO), δ 0.82 (s, 3H), 1.21-1.45 (m, 10H), 3.51 (s, 2H), 7.24 (d, J=8.55 Hz, 2H), 7.51 (d, J=8.55 Hz, 2H), 7.78 (s, 1H), 8.04 (d, J=9.00 Hz, 2H), 8.36 (d, J=8.97 Hz, 2H), 11.12 (br, 1H). HRMS exact mass of C$_{24}$H$_{25}$N$_3$O$_6$S$_2$, (M$^+$Na)$^+$, 538.1083 amu; found: 538.1092 amu. Anal. calcd C, 55.91; H, 4.89; O, 18.62. found C, 55.98; H, 4.98; O, 18.76.

The complete disclosure of all patents, patent applications, and publications, and electronically available materials cited herein are incorporated by reference. The foregoing detailed description and examples have been given for clarity of understanding only. No unnecessary limitations are to be understood therefrom. In particular, while various theories are presented describing possible mechanisms through with the thiazolidinedione derivatives are effective, the thiazolidinedione derivatives are effective regardless of the particular mechanism employed and the inventors are therefore not bound by theories described herein. The invention is not limited to the exact details shown and described, for variations obvious to one skilled in the art will be included within the invention defined by the claims.

What is claimed is:

1. A method of inhibiting glycolysis in a subject, comprising administering to the subject a pharmaceutical composition including a compound of formula IV:

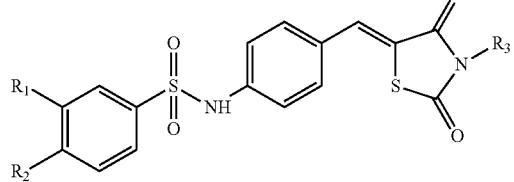

IV wherein $R_1$ is a hydrogen, methyl, or trifluormethyl moiety; $R_2$ is a methoxy or nitro moiety, and $R_3$ is an alkyl or cycloalkyl group.

2. The method of claim 1, wherein the compound is selected from the group consisting of 4-Methoxy-N-{4-[3-(1-methyl-cyclohexylmethyl)-2,4-dioxo-thiazolidin-5-ylidenemethyl]-phenyl}-benzenesulfonamide, N-{4-[3-(1-Methyl-cyclohexylmethyl)-2,4-dioxo-thiazolidin-5-ylidenemethyl]-phenyl}-4-nitro-3-trifluoromethyl-benzenesulfonamide, and N-{4-[3-(1-Methyl-cyclohexylmethyl)-2,4-dioxo-thiazolidin-5-ylidenemethyl]-phenyl}-4-nitro-benzenesulfonamide.

* * * * *